US012308116B2

(12) United States Patent
Kadri et al.

(10) Patent No.: US 12,308,116 B2
(45) Date of Patent: *May 20, 2025

(54) MULTI-SPECIALTY INTEGRATED CARE SCHEDULING SYSTEM

(71) Applicant: Kadri Medical Ltd., Windsor (CA)

(72) Inventors: Albert Kadri, Windsor (CA); Mohammed Ibrahim, Windsor (CA)

(73) Assignee: Kadri Medical Ltd., Windsor (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/417,657

(22) Filed: Jan. 19, 2024

(65) Prior Publication Data

US 2024/0170136 A1     May 23, 2024

Related U.S. Application Data

(63) Continuation-in-part of application No. 17/988,444, filed on Dec. 12, 2022, which is a
(Continued)

(51) Int. Cl.
    *G16H 40/20*      (2018.01)
    *G16H 50/30*      (2018.01)

(52) U.S. Cl.
    CPC ............. *G16H 40/20* (2018.01); *G16H 50/30* (2018.01)

(58) Field of Classification Search
    CPC ........ G16H 40/20; G16H 50/30; G16H 50/20; G16H 40/67; G16H 10/20; Y02A 90/10
See application file for complete search history.

(56) References Cited

U.S. PATENT DOCUMENTS

| | | | |
|---|---|---|---|
| 11,222,718 B2 * | 1/2022 | Kadri | ..................... G16H 10/60 |
| 11,345,370 B2 | 5/2022 | Lacaze | |
| 2016/0307145 A1 | 10/2016 | Banerjee | |

FOREIGN PATENT DOCUMENTS

WO      9407210 A1      3/1994

OTHER PUBLICATIONS

Non-Final Office Action dated Jan. 31, 2024, U.S. Appl. No. 17/988,444.

(Continued)

*Primary Examiner* — Matthew Mikels
(74) *Attorney, Agent, or Firm* — The Dobrusin Law Firm, PC

(57) ABSTRACT

A method of determining practitioner service intensity required per patient for automated medical appointments, data being a plurality of predetermined physical conditions of a patient, each of the plurality of predetermined physical conditions having a predetermined assigned weight based on level of severity, generating a summation of the total weight for each predetermined physical condition, generating a predetermined specialty acuity score by comparing the corresponding range of the total weight and generating a report to output of the specialty acuity score, the specialty acuity score used to determine priority of scheduling patients in a system. Specialty acuity score may be generated for each system affected, the systems each assigned a value of 1. Determining a modified TOR ("mTOR") wherein the mTOR is the TOR divided by the summation of the SPA score and the PTI and using the mTOR is used to schedule appointments for patients in a system schedule.

6 Claims, 57 Drawing Sheets

Related U.S. Application Data continuation-in-part of application No. 17/539,899, filed on Dec. 1, 2021, application No. 18/417,657 is a continuation-in-part of application No. 16/939,203, filed on Jul. 27, 2020, now Pat. No. 11,227,077, and a continuation-in-part of application No. 16/939,216, filed on Jul. 27, 2020, now Pat. No. 11,222,718, and a continuation-in-part of application No. 16/751,832, filed on Jan. 24, 2020, now Pat. No. 11,138,347, said application No. 16/939,216 is a continuation-in-part of application No. 16/112,835, filed on Aug. 27, 2018, now Pat. No. 11,127,496, said application No. 16/751,832 is a continuation-in-part of application No. 16/112,835, filed on Aug. 27, 2018, now Pat. No. 11,127,496, application No. 18/417,657 is a continuation-in-part of application No. 16/112,835, filed on Aug. 27, 2018, now Pat. No. 11,127,496.

(60) Provisional application No. 63/440,755, filed on Jan. 24, 2023, provisional application No. 63/120,369, filed on Dec. 2, 2020, provisional application No. 63/018,830, filed on May 1, 2020, provisional application No. 62/878,788, filed on Jul. 26, 2019, provisional application No. 62/878,793, filed on Jul. 26, 2019, provisional application No. 62/878,830, filed on Jul. 26, 2019, provisional application No. 62/796,347, filed on Jan. 24, 2019, provisional application No. 62/569,737, filed on Oct. 9, 2017.

(56) References Cited

OTHER PUBLICATIONS

Final Office Action dated Sep. 22, 2023, U.S. Appl. No. 17/539,899.
Non-Final Office Action dated Jun. 13, 2023, U.S. Appl. No. 17/539,899.

* cited by examiner

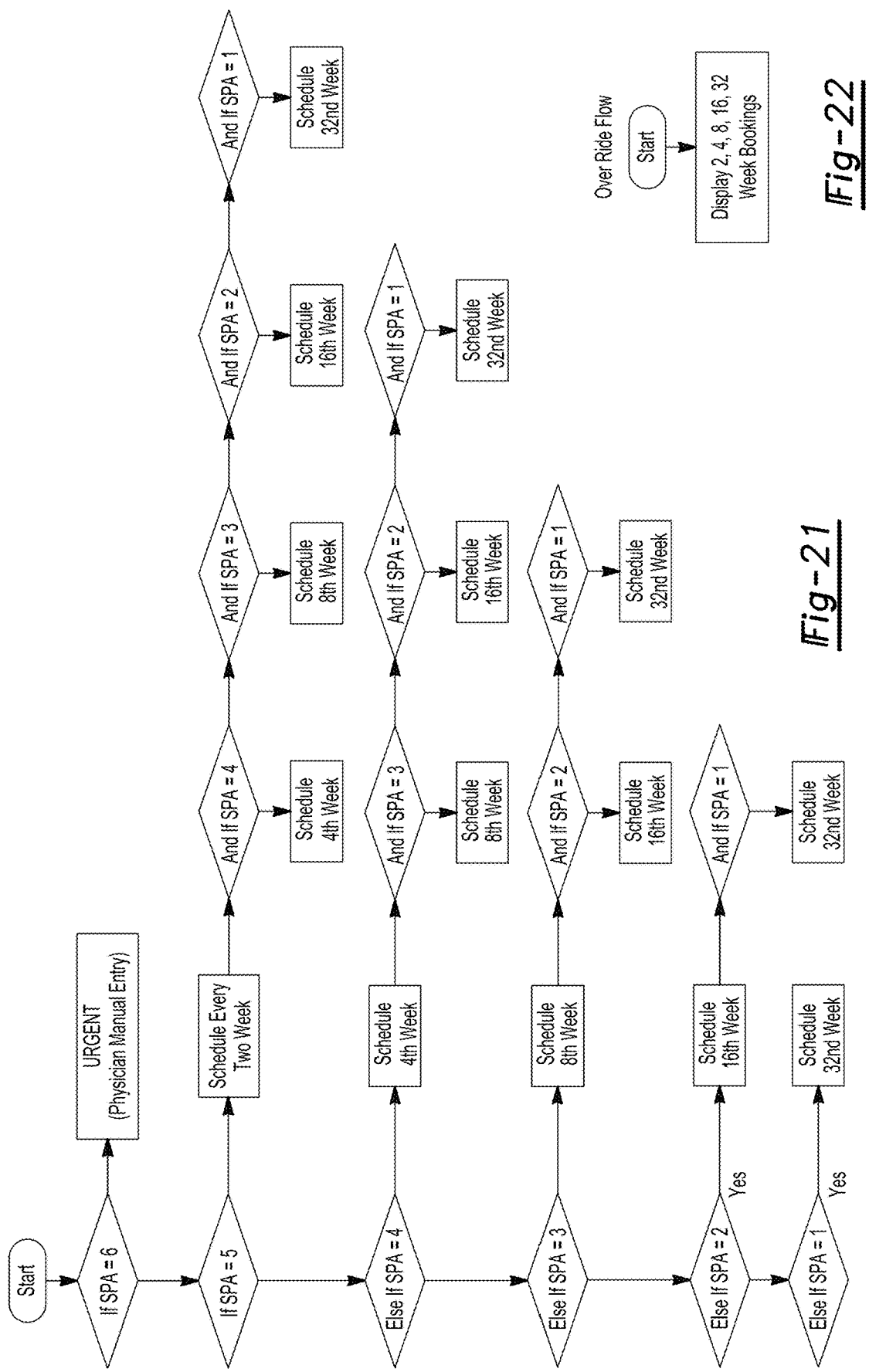

User Management

- User Management
- SPA Scores
- Specialty Categories
- TOR
- Lab Requisition
- Block Times

Physicians | Allied Assistants

Search [          ]    [Add User]

| Name | Category | |
|---|---|---|
| Physician Name | Cardiologists | View Details |
| Physician Name | Obstetrician | View Details |
| Physician Name | Gynecologists | View Details |
| Physician Name | Cardiologists | View Details |
| Physician Name | Endocrinologists | View Details |
| Physician Name | Gastroenterologists | View Details |
| Physician Name | Gynecologists | View Details |
| Physician Name | Endocrinologists | View Details |
| Physician Name | Cardiologists | View Details |

*Fig-38*

| User Management |
| --- |
| SPA Scores |
| Specialty Categories |
| TOR |
| Lab Requisition |
| Block Times |

Physician Details

Physician Name

Dr. Kadri

Address

Dr. Kadri

Email

Dr.Kadri@gmail.com

Category

Cardiologist ▷

Hours of Operation

| Days | Capacity |
| --- | --- |
| Saturday | 03:00 PM - 08:00 PM |
| Sunday | 03:00 PM - 08:00 PM |
| Monday | 03:00 PM - 08:00 PM |
| Tuesday | 03:00 PM - 08:00 PM |
| Wednesday | 03:00 PM - 08:00 PM |
| Thursday | 03:00 PM - 08:00 PM |
| Friday | 03:00 PM - 08:00 PM |

*Fig-39*

SPA Scores

| Score | Weight | Duration (Weeks) | |
|---|---|---|---|
| 1 | 1 - 3 | 32 | Edit |
| 2 | 4 - 6 | 16 | Edit |
| 3 | 7 - 9 | 8 | Edit |
| 4 | 10 - 12 | 4 | Edit |
| 5 | 12 - 14 | 2 | Edit |
| 6 | -> 15 | < 1 | Edit |

Add Item

User Management
SPA Scores
Specialty Categories
TOR
Lab Requisition
Block Times

*Fig-40*

Categories

User Management
SPA Scores
Specialty Categories
TOR
Lab Requisition
Block Times Add Item

| Category Title | |
|---|---|
| Physicians | Edit |
| Allied Assistants | Edit |

*Fig-41*

Categories - Physicians

Cardiologists | Obstetricians | Gynecologists | Endocrinologists | Gastroenterologists

[ Lab Requisition Checklist ] [ Symptoms Checklist ]

Add Item

| Checklist Item | Weight | |
|---|---|---|
| Previous Heart Attack | 1 | Edit |
| Previous Coronary Stent or Bypass Surgery | 1 | Edit |
| Chest Pain with Moderate Exertion | 2 | Edit |
| Chest Pain with Minimal Exertion | 4 | Edit |
| Shortness of Breath with Minimal Exertion | 2 | Edit |
| Shortness of Breath with Moderate Exertion | 3 | Edit |
| Minimal Edema | 1 | Edit |
| Moderate Edema | 2 | Edit |
| Severe Edema | 3 | Edit |
| Echocardiogram Showing Ejection Fraction less then 30% | 2 | Edit |
| Echocardiogram Showing Ejection Fraction less then 15% | 3 | Edit |
| Moderate Valvular Heart Disease | 1 | Edit |

Sidebar:
- User Management
- SPA Scores
- Specialty Categories
- TOR
- Lab Requisition
- Block Times

*Fig-42*

Categories - Physicians

Cardiologists    Obstetricians    Gynecologists    Endocrinologists    Gastroenterologists

| Lab Requisition Checklist | Symptoms Checklist | | Add Item |
|---|---|---|---|

| Checklist Item | |
|---|---|
| ☑ | Complete Blood Count |
| ☐ | Random Blood Sugar |
| ☐ | Fasting Blood Sugar |
| ☐ | Calcium Level |
| ☐ | Liver Profile |
| ☐ | Thyroid Function Testing |
| ☐ | Urine Analysis |
| ☐ | Urine Albumin/Creatinine Ration |
| ☐ | Chest X-Ray |
| ☐ | EKG |
| ☐ | Abdominal Ultrasound |
| ☐ | Echocardiogram |

Save

Sidebar:
- User Management
- SPA Scores
- Specialty Categories
  - TOR
  - Lab Requisition
  - Block Times

*Fig-43*

| User Management |
| SPA Scores |
| Specialty Categories |

TOR

| Lab Requisition |
| Block Times |

TOR

| TOR Score | Impact on Highest SPA Score | |
|---|---|---|
| 0 - 9 | 0 | Edit |
| 10 - 19 | [SPA Score + 1] =< 6 | Edit |
| > 19 | [SPA Score + 2] =< 6 | Edit |

Add Item

Fig-44

Change Time Period for Combining Requisitions

Duration (Weeks)

Save

User Management
SPA Scores
Specialty Categories
TOR
Lab Requisition
Block Times

*Fig-45*

Block Times

Duration (Weeks)

Save

User Management
SPA Scores
Specialty Categories
TOR
Lab Requisition
Block Times

Appointment View

Patient History | Quick Consult

Patient Name

[Patient Name]

Cardiology

- ☐ Previous heart attack
- ☑ Previous coronary stent or bypass surgery
- ☐ Chest pain with moderate exertion
- ☐ Chest pain with minimal exertion
- ☑ Chest pain at rest
- ☐ Shortness of breath with minimal exertion
- ☐ Shortness of breath with moderate exertion
- ☐ Minimal Edema
- ☑ Moderate Edema
- ☐ Severe Edema
- ☐ Echocardiogram showing ejection fraction less than 30%
- ☑ Echocardiogram showing ejection fraction less than 15%
- ☐ Moderate valvular heart disease
- ☐ Severe valvular heart disease
- ☐ Requiring high-dose diuretic therapy
- ☑ Previous hospital admission for congestive heart failure within the last 12 months
- ☐ Hypertension controlled on medication
- ☐ Hypertension - uncontrolled
- ☐ Hypotension
- ☑ Cardiorenal syndrome Sample checklist for lab work

- ☐ Complete blood count
- ☑ Random blood sugar
- ☐ Fasting blood sugar
- ☐ Electrolyte panel
- ☑ Calcium level
- ☐ Liver profile
- ☐ Thyroid function testing
- ☐ Urine analysis
- ☑ Urine albumin/creatinine ratio
- ☐ Chest X-ray
- ☐ EKG
- ☑ Abdominal ultrasound
- ☐ Echocardiogram
- ☐ Renal ultrasound
- ☐ Serum protein electrophoresis
- ☑ Albumin level
- ☐ Total protein level
- ☐ Glycated hemoglobin level
- ☐ INR level Notes

[                    ]

Schedule Follow Up

*Fig-49*

Appointment View - Follow Up

Appointment Date & Time

20/Jul/2020 - 03:30 PM

23/Jul/2020 - 01:00 PM

25/Jul/2020 - 01:00 PM

Confirm  Override

Fig-50

Appointment View - Override

BE AWARE!
You are about to override the appointment date

Appointment Date

20/Jul/2020

Appointment Time

03:30 PM

Override

Fig-51

Quick Consultation

Quick Consultation

Consultation Subject

| Consultation Subject |

User List

| Muhammed, Zaid, Ahmed + 12  ▽ |

Consultation Notes

| Notes |

[ Send ]

Fig-52

| Level or grade | Criteria |
| --- | --- |
| Evidence | |
| 1+ | Systematic overview or meta-analysis of randomized controlled trials |
| 1 | Randomized controlled trial with adequate power |
| 2+ | Randomized controlled trial that does not meet level 1 criteria |
| 3 | Nonrandomized clinical trial or cohort study |
| 4 | Before–after study, cohort study with noncontemporaneous controls, case–control study |
| 5 | Case series with controls |
| 6 | Case series without controls |
| Recommendation | |
| A | Supported by level 1 or 1+ evidence plus consensus |
| B | Supported by level 2 or 2+ evidence plus consensus |
| C | Supported by level 3 evidence plus consensus |
| D | Any lower level of evidence supported by consensus |

*Identified articles were reviewed, and the summary statements developed from these articles were assigned a level of evidence (from 1 = highest to 4 = lowest). Recommendations were assigned a grade, according to a system that incorporated both level of evidence and expert consensus (from A = highest to D = lowest).

*Fig. 61*

MULTI-SPECIALTY INTEGRATED CARE SCHEDULING SYSTEM

CROSS REFERENCE TO RELATED APPLICATIONS

Technical Field

The present specification generally relates to a schedule and record keeping system and, more specifically, a multi-specialty integrated care clinic and laboratory scheduling system using risk and benefit-based calculations to prioritize uptake of therapy.

BACKGROUND

Scheduling patients for follow up visits at their primary care physician or specialist office is traditionally random and done in a non-standardized and oftentimes isolated manner. This leads to multiple uncoordinated, with multiple different sets of lab work and investigations at different times and segregated that can be very duplicative. With an aging population, with multiple medical problems present in each patient, there is an increasing desire from clinicians, funding agencies, etc., to coordinate care health care in a cost-effective manner, for a more holistic and effective approach to patient centered care. However, a solution has not yet been effectively implemented.

There are numerous factors to be considered when scheduling a patient's follow up visit such as patient load in a physician's practice, their waiting list, as well as individual physician and patient availability based on other commitments. The patient's clinical status certainly factors in, but not in a standardized fashion. This can lead to a lack of timely follow up for patients and has the potential to the increase utilization of emergency rooms and a higher need for hospitalization.

In addition, individual physicians (involved in any given patient's care) office scheduling systems, assessments, and laboratory and investigation requisitions are not coordinated and care is not integrated optimally as a result. Alert notification systems for review of pertinent lab work is isolated and not coordinated among care providers.

Accordingly, there exists a need in the art to provide a system and method to overcome the aforementioned disadvantages.

The frequency and priority of scheduling of visits and lab/investigations across multiple specialties needs to mirror the clinical needs of the patient. Due to the traditional physician clinic setup being individualized and not integrated across different specialists' and primary care offices, each most often having different physical locations, electronic medical record (EMR) systems, and scheduling systems that are individual provider based, the coordination of visits of more than one specialist is nearly impossible for same day or even the same physical building. This leads to many patient's only interacting with their primary care physician or specialist on as needed basis, rather than in accordance with their medical needs. In addition, prior to each individual appointment with primary care physicians and specialists, laboratory and other investigations are often necessary and done in significant duplication prior to each individual clinic visit with different physicians.

Duplication of lab investigations comes at great cost, inconvenience, as well as time away from productive activity for patients. Often the results of these investigations are not specifically copied to all physicians in the circle of care, and very specific tests needed by any individual physician are often repeated even if results from another physician are available. There is currently no system to coordinate efficient same day and/or same site follow up visits between different specialties to allow multi-specialty intervention that meets the priority needs of any individual patient, while making sure the care remains comprehensive as well. This is a significant problem within the healthcare system and contributes to a lack of access to timely intervention. The lack of timely access is known to influence outcomes for patients. It also leads to inefficient duplication of services and laboratory/investigations and increased health care costs as well as a loss of time and inconvenience to patients within the system due to multiple visits to the laboratory as well as to different specialty and primary care clinics.

Accordingly, there exists a need in the art to provide a system and method to overcome the aforementioned disadvantages. The system provided herein provides for multi-specialty scheduling and laboratory/investigation scheduling seeks to provide a solution to this problem, to allow access to the right care at the right time in a standardized and efficient fashion.

In the medical field, it is standard to have a primary care physician office fully separate and spaced apart from any specialist physician. As is standard, a patient will first visit a primary care physician and then, if required, be referred to a specialist. The patient must then make an appointment with that specific specialist, often many months later. If desired, the patient must then make a separate appointment with another specialist for a second opinion.

As a background in one application of medicine, vascular healthcare is examined. Cardiovascular disease is a leading cause of death in North America and has become a public health epidemic. Cardiovascular disease and the associated risk factors are linked to an increased risk of morbidity and mortality and are also responsible for escalating healthcare costs. Traditionally, if a primary care physician thinks that a patient should be examined by a cardiologist, the patient is referred to a cardiologist and must make an appointment with the cardiologist's office, often at an entirely different location. When a second opinion is desired, as is often the case, the patient is again responsible for making an appointment. This system delays healthcare delivery to the patient, is time consuming, inconvenient and very costly. Separate EMRs (electronic medical records), and poor information sharing adds to the dysfunctional delivery of care. The current system is highly disjointed and inefficient for practitioners and patients alike.

Typically, a high risk vascular patient must visit several different specialist physicians (cardiologist, endocrinologist, nephrologist, etc.), medical laboratories, imaging facilities, a pharmacy, and their primary care physician. Usually, each of these encounters occurs at different locations and together comprise basic healthcare. The clinical information from each of these separate encounters is not readily available to the individual healthcare providers and is almost always not available to the patient. This process results in the patient being less involved in their healthcare decisions. The patient is further burdened with the responsibility of coordinating multiple appointments (and time away from work) to manage their health.

Accordingly, improved approaches are needed within healthcare systems to address this epidemic and improve patient education, attendance, and adherence to strategies known to improve health outcomes while limiting financial burden. As such, a need exists in an improved medical clinic design, enhanced by an improved clinic layout and multispecialty care and integrated technologies suited to optimize the patient's time in clinic, healthcare involvement and overall health outcomes.

Typically, community-based laboratories are separate operational entities and often in separate locations from medical clinics, typically being in separate building and owned by separate entities. In some scenarios, bloodletting is often done within a clinic but is then shipped to a centralized laboratory for processing. In a community-based setting patients typically visit a laboratory approximately 1-2 weeks prior to a clinic appointment in order to allow time for processing and information to be sent to their practitioners to be reviewed at their clinic appointments. This creates the need for two separate visits for laboratory investigations and then subsequent clinical assessment by practitioners. This aforementioned process is inefficient for the patients and does not allow for immediate same-day results to be used in clinical decision-making Typically decisions are made based on lab work obtained 1 to 2 weeks prior to the clinic visit. In addition, if the patient forgets to do their lab work, it is often a less impactful clinic visit, with the need to subsequently do the lab work after the clinic visit and follow up on the results without the patient present to be fully informed of their status.

Barriers to having laboratory investigations done on the same visit to the clinical practitioner are multiple. These barriers include the efficiency and processing of bloodletting from patients, remote locations of the central laboratory from clinical practices with bloodletting done and samples being shipped to the central location.

Accordingly, a need exists for an improved laboratory physical layout and process to allow bloodletting to occur within a clinic setting on the same floor to allow for convenience, efficiency and coordination with clinic visits with a separate yet physically connected full laboratory outside of the clinic setting in view of the aforementioned disadvantages.

In the medical field, it is standard to have a primary care physician office fully separate and spaced apart from any specialist physician. As is standard, a patient will first visit a primary care physician and then, if required, be referred to a specialist. The patient must then make an appointment with that specific specialist, often many months later. If desired, the patient must then make a separate appointment with another specialist for a second opinion.

As a background in one application of medicine, vascular healthcare is examined. Cardiovascular disease is a leading cause of death in North America and has become a public health epidemic. Cardiovascular disease and the associated risk factors are linked to an increased risk of morbidity and mortality and are also responsible for escalating healthcare costs. Traditionally, if a primary care physician thinks that a patient should be examined by a cardiologist, the patient is referred to a cardiologist and must make an appointment with the cardiologist's office, often at an entirely different location. When a second opinion is desired, as is often the case, the patient is again responsible for making an appointment. This system delays healthcare delivery to the patient, is time consuming, inconvenient and very costly. Separate EMRs (electronic medical records), and poor information sharing adds to the dysfunctional delivery of care. The current system is highly disjointed and inefficient for practitioners and patients alike.

Typically, a high-risk vascular patient must visit several different specialist physicians (cardiologist, endocrinologist, nephrologist, etc.), medical laboratories, imaging facilities, a pharmacy, and their primary care physician. Usually, each of these encounters occurs at different locations and together comprise basic healthcare. The clinical information from each of these separate encounters is not readily available to the individual healthcare providers and is almost always not available to the patient. This process results in the patient being less involved in their healthcare decisions. The patient is further burdened with the responsibility of coordinating multiple appointments (and time away from work) to manage their health.

Accordingly, improved approaches are needed within healthcare systems to address this epidemic and improve patient education, attendance, and adherence to strategies known to improve health outcomes while limiting financial burden. As such, a need exists in an improved medical clinic design, enhanced by an improved clinic layout and multi-specialty care and integrated technologies suited to optimize the patient's time in clinic, healthcare involvement and overall health outcomes.

In the midst of a pandemic, what has been lost is the appropriate practice of medicine. There has been a move to phone assessments or telemedicine-based assessments. There has been a reluctance to send people to offices are laboratories with busy waiting rooms. It was unclear how viruses spread initially and any pandemic and the degree of contagiousness etc. there is a need to protect both patients and healthcare staff yet continue to provide appropriate care to patients to avoid complications, emergency room visits and hospitalizations.

Drawbacks of virtual visits including no lab, no imaging and no physical examination. Accordingly, a need exists for an improved means for patient transport, diagnosis and data collection.

The uptake of proven therapies to reduce an individual patient's risk of adverse events remains poor, and in some studies as low as 40-50% of therapies or actually prescribed and consistently taken by patients. This leads to elevated risk profiles for patients for adverse outcomes, as well as having impacts on community public health measures and hospital based services. Strategies are needed to optimize uptake and compliance to medical therapies proven to improve outcomes. (1,2). There is often therapeutic inertia on the part of the patient and the physician as well as health equity factors that prevent the optimal uptake of proven therapies and these strategies are designed to address this phenomenon. Accordingly, there exists a need in the art to provide an improved scheduling system. See European Heart Journal, Volume 34, Issue 17, 1 May 2013, Pages 1262-1269, https://doi.org/10.1093/eurheartj/ehs481, 2/1/2013 and ADHERENCE TO LONG-TERM THERAPIES Evidence for action, World Health Organization 2003).

SUMMARY

A method of determining practitioner service intensity required per patient. A method of automated medical scheduling including the steps of receiving user specified data on a processor via a checklist, said data being a plurality of predetermined physical conditions of a patient, each of the plurality of predetermined physical conditions having a predetermined assigned weight based on level of severity, generating a summation of the total weight for each predetermined physical condition, generating a predetermined specialty acuity ("SPA") score by comparing the corresponding range of the total weight, and using the SPA score used to schedule appointments for patients in a system schedule and to schedule sending of an autonomous vehicle sent to the patient for pickup. In some embodiments, a SPA score is generated for each system affected, the systems including Cardiac, Renal, Neurological, Vascular, Medical/Metabolic and Pulmonary, each assigned a value of 1 wherein a comorbidity score is generated by the summation of each system. Further, a Total Overall Risk ("TOR") score is generated by multiplying the summation of each system by the total SPA scores, generating a report of the TOR score, may be provided. The method may further determine frequency of appointment scheduling, comparing the TOR score to a set of predetermined ranges, assigning an appointment interval corresponding with the TOR score value. Further, an appointment interval is assigned for ancillary care assessments corresponding to the TOR score value. In some embodiments, the TOR score is used to determine visit frequency as an amplifier for SPA score passed on physician visits.

In another aspect, an autonomous vehicle for transporting a patient to at least one medical appointment, the autonomous vehicle include a plurality of sensors, the plurality of sensors selected from a group of: cameras, blood pressure sensor, ultrasound, x-ray, EKG sensor, heart sensor, blood sugar sensor, and/or perspiration sensor, and a display within the vehicle, the display providing for virtual communication with a remotely located health care professional. In some embodiments, a robotic arm is positioned within the vehicle, the robotic arm configured assist in testing the patient. The display may be voice activated. The display may be configured to accept voice recognition.

The system and apparatus of the present includes an autonomous vehicle specifically for medical applications and a corresponding system for coordinating vehicle dispatch and vehicle control. Referring to prior filed application, the automobile is the inspiration for the unilateral flow design and physical set up upon specific north/south entrances and east/west exits with clockwise flows through clinic for infection control. With the inclusion of electric autonomous vehicle, the goal of a carbon free medical clinic can be achieved.

As discussed in prior applications herein incorporated by reference, solar paneling on roof of copyrighted building plans and use of electric autonomous vehicles for pick up and drop off of patients, controlled by the electronic operating system. Drop off circle on the outside lane around building for transportation of patients. Pick up circle on the inside lane around building. Further, both lanes can be clockwise or counterclockwise or in opposite directions depending on optimal configuration for local traffic flow. Drop off at North entrance under main floor and drop off South entrance through parking garage and can access any floor level.

Physical plant will have negative pressure system for the clinic rooms and also for the Electric autonomous vehicles. The scheduling system previously disclosed and claimed and is herein incorporated by reference explains how multidisciplinary care can be coordinated either physically or virtually.

The present apparatus and system provided the virtual component to the physical plant and software systems. This is the virtual component but it will provide a level of care superior to historical and standard in person visits, using a novel design of an electric autonomous vehicle for the purpose of providing robotic assisted remote physical examination, imaging and laboratory sampling with the goal of transitioning to completely virtual assessment (i.e. no need for a medical professional to be present in the vehicle).

Camera systems and EOS technology connected through the car cab has the ability to use an autoscope, tongue depressor, swabs etc.

Further, as a transitional phase, these vehicles will pick up patients and bring them to the clinic for in person assessment. In the absence of a pandemic, this system still increases efficiency through:
Preassessment
increases time effectiveness for a patient for a visit
Increases attendance to clinics
Avoids transportation issues and expense and inconvenience related to such
Environmentally friendly and promotes a carbon free environment and is more inexpensive A method of automated medical scheduling including the steps of receiving user specified data on a processor via a checklist, said data being a plurality of predetermined physical conditions of a patient, each of the plurality of predetermined physical conditions having a predetermined assigned weight based on level of severity, generating a summation of the total weight for each predetermined physical condition, generating a predetermined specialty acuity ("SPA") score by comparing the corresponding range of the total weight, an untreated Total Overall Risk ("TOR") score is generated by multiplying the summation of each system by the total SPA scores, generating a report of the TOR score, if the TOR is greater than 10, a Priority Treatment Index (PTI) is generated wherein the PTI, determining a modified TOR ("mTOR") wherein the mTOR is the TOR divided by the summation of the SPA score and multiplied by the PTI, and using the mTOR is used to schedule appointments for patients in a system schedule and is used to adjust scheduling to reduce frequency of visits inversely proportional to the value of the mTOR score A SPA score may be generated for each system affected, the systems including Cardiac, Renal, Neurological, Vascular, Medical/Metabolic and Pulmonary, each assigned a value of 1. A comorbidity score may be generated by the summation of each system. The method further comprising the step of to determine frequency of appointment scheduling, comparing the TOR score to a set of predetermined ranges, assigning an appointment interval corresponding with the TOR score value. In some embodiments, an appointment interval is assigned for ancillary care assessments corresponding to the TOR score value. In other embodiments, the TOR score is used to determine visit frequency as an amplifier for SPA score passed on physician visits.

A method of automated medical scheduling including
receiving user specified data on a processor via a checklist, said data being a plurality of predetermined physical conditions of a patient, each of the plurality of predetermined physical conditions having a predetermined assigned weight based on level of severity;
generating a summation of the total weight for each predetermined physical condition;
generating a predetermined specialty acuity ("SPA") score by comparing the corresponding range of the total weight;
an Total Overall Risk ("TOR") score is generated by multiplying the summation of each system by the total SPA scores, generating a report of the TOR score;
if the TOR is greater than 10, a Priority Treatment Index ("PTI") is generated;
assigning a Treatment Priority Acuity ("TPA") score, the TPS score calculating a Practitioner Service Intensity ("PSI") by multiplying the TOR by the summation of the TPA;

using the PSI is used to predict required practitioner service intensity; and using the above PSI to schedule at least one appointment for said patient in a system schedule.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 21 depicts a flow diagram depicting the process of scheduling appointments to determining the best week according to a multiple of weeks according to one or more embodiments shown and described herein;

FIG. 22 depicts a flow diagram illustrating the option to override according to one or more embodiments shown and described herein;

FIG. 38 depicts an exemplary screen shot of the user management of the system according to one or more embodiments shown and described herein;

FIG. 39 depicts an exemplary screen shot of the user management (physician details) of the system according to one or more embodiments shown and described herein;

FIG. 40 depicts an exemplary screen shot defining SPA scores of the system according to one or more embodiments shown and described herein;

FIG. 41 depicts an exemplary screen shot defining categories of the system according to one or more embodiments shown and described herein;

FIG. 42 depicts an exemplary screen shot defining categories of the system according to one or more embodiments shown and described herein;

FIG. 43 depicts an exemplary screen shot illustrating a checklist of the system according to one or more embodiments shown and described herein;

FIG. 44 depicts an exemplary screen shot illustrating the TOR score of the system according to one or more embodiments shown and described herein;

FIG. 45 depicts an exemplary screen shot defining duration of the system according to one or more embodiments shown and described herein;

FIG. 46 depicts an exemplary screen shot defining block times of the system according to one or more embodiments shown and described herein;

Figure 47:
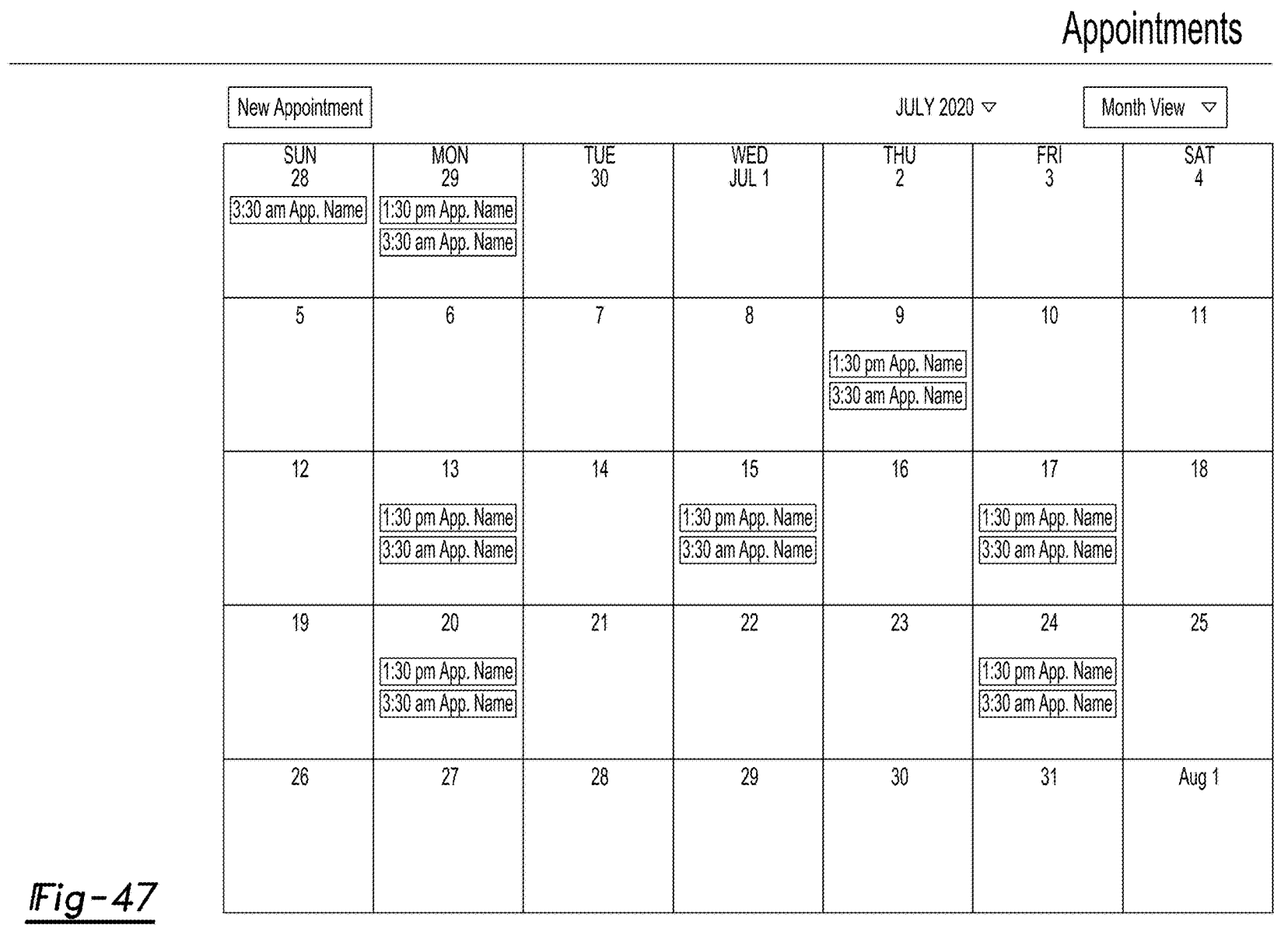

FIG. 47 depicts an exemplary screen shot defining a calendar of the system according to one or more embodiments shown and described herein;

Figure 48:
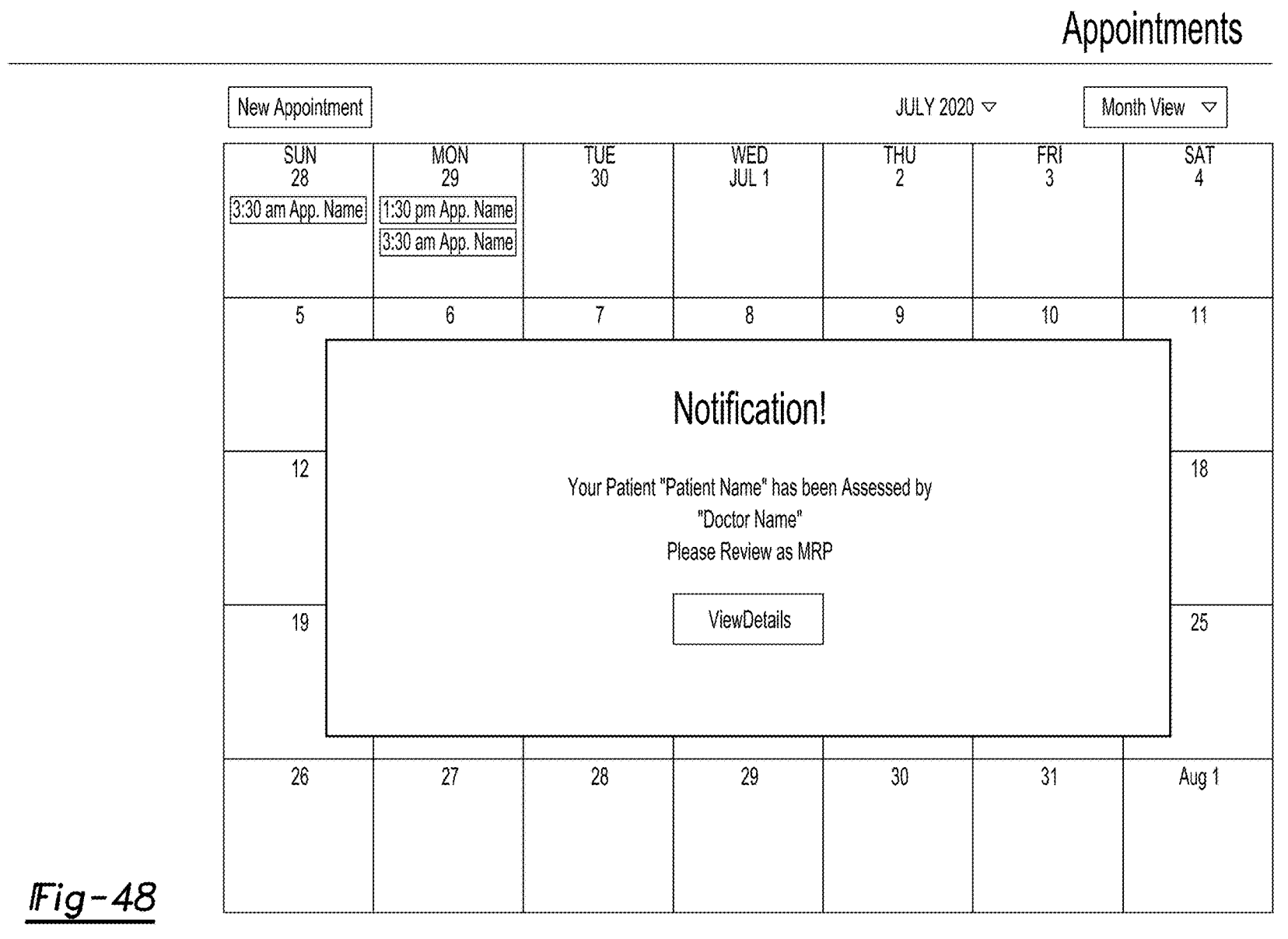

FIG. 48 depicts an exemplary screen shot defining notification of the system according to one or more embodiments shown and described herein;

FIG. 49 depicts an exemplary screen shot defining a checklist of conditions and/or occurrences of the system according to one or more embodiments shown and described herein;

FIG. 50 depicts an exemplary screen shot illustrating appointment confirmation of the system according to one or more embodiments shown and described herein;

FIG. 51 depicts an exemplary screen shot illustrating appointment override of the system according to one or more embodiments shown and described herein;

FIG. 52 depicts an exemplary screen shot illustrating quick consultation of the system according to one or more embodiments shown and described herein;

FIG. 61 depicts a graphical depiction the criteria according to one or more embodiments shown and described herein.

DETAILED DESCRIPTION

The present disclosure relates to a system and method of determining a score for the purposes of objectively scheduling patients. The present disclosure discloses a multi-specialty clinic, wherein each patient has a most responsible practitioner health professional involved in their care. This includes medical specialists (cardiologist, nephrologist, endocrinologist, internist, vascular specialist), primary care family physicians, as well as allied health care professionals such as nurse practitioners, pharmacists, dieticians, social workers etc.). A plurality of factors are considered and scores are determined to calculate, from a objective standpoint, which patients to give priority to, and standardized scheduling frequency according to overall risk status across multiple specialties.

The present specification discloses a medical clinic layout including a waiting room, reception area, modular clinic pods, patient exam rooms, physician workspace and collaboration area, pharmacy, laboratory, urgent care, imaging . . . etc. along with corresponding flow arrows to illustrate the optimization of the medical clinic layout's efficiency. The present application includes a unique physical and operational design for a vascular health clinic, by way of example. It should be understood that the present clinic layout can apply to various different health specialties and practices and is not limited to vascular health. These components are specifically fashioned to work synergistically to increase the efficiency of healthcare delivery and improve health outcomes, while also moving away from provider-centered care to patient-centered care. The design also minimizes the area required to provide multidisciplinary and multispecialty healthcare.

The design of the present specification is configured to eliminate the fundamental problems, as previously described, with the current healthcare model. Patients will have access to their primary care physician, a select group of vascular health specialists, including cardiology, nephrology, endocrinology, neurology, and vascular surgery (available on-demand for 'quick' problem specific consultation), a medical laboratory, imaging, diagnostics, and pharmacy services, all at the same location, and in the same visit. A corresponding computer application and companion mobile device application are also provided.

By implementing the below described design and utilizing the corresponding computer program and companion mobile device application (as described in the parent), healthcare providers will be able to increase the efficiency and quality of healthcare delivery, facilitate and simplify coordination of care, enhance patient involvement in healthcare and measure and improve health outcomes in patients with vascular disease through clinical evidence-based strategies. By implementing this complete design, a new gold standard of healthcare will be achieved.

Figure 1:
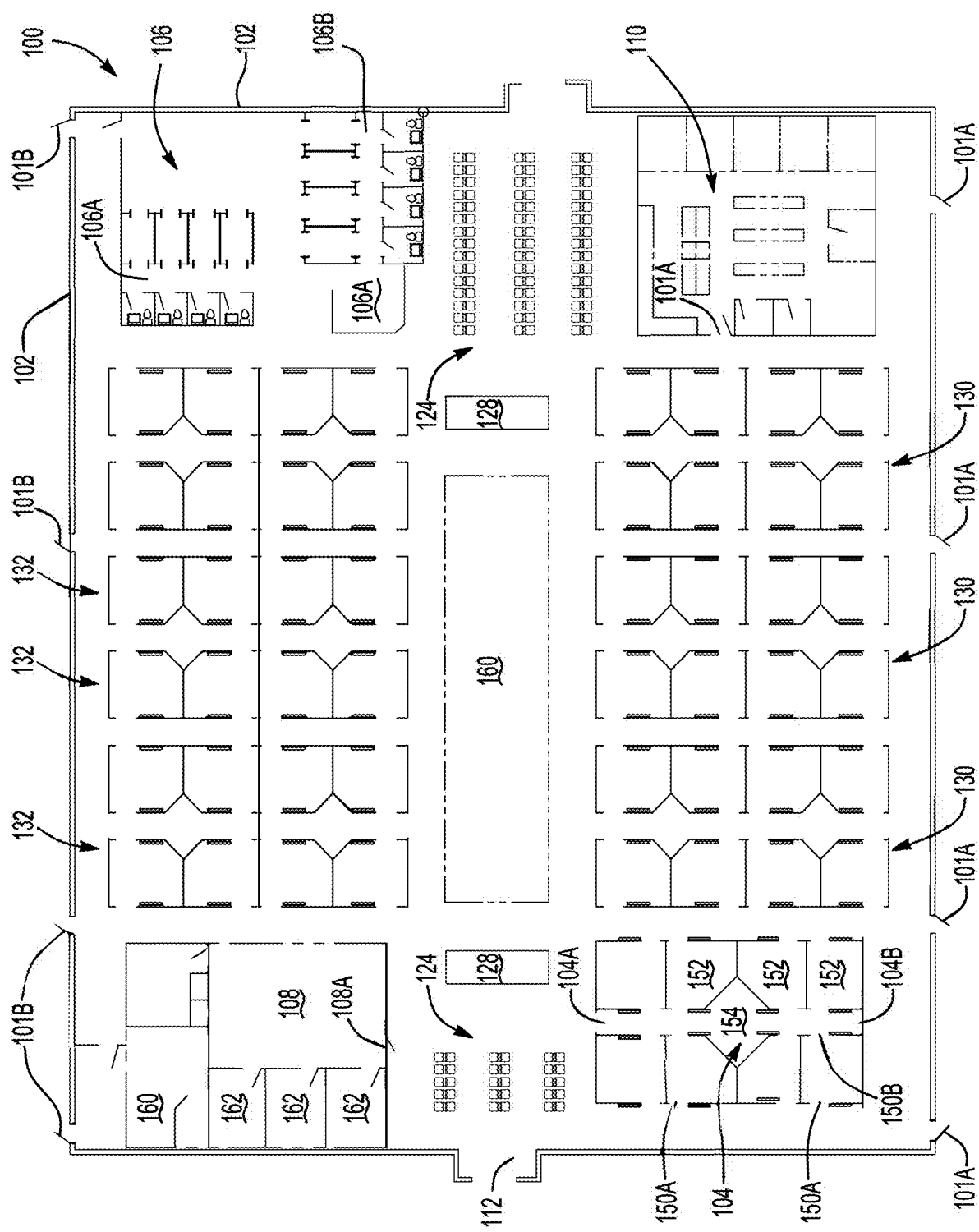
FIG. 1 depicts an exemplary first floor medical clinic layout having waiting rooms, a lab, reception, primary care pods, specialist pods, pharmacy, urgent care, and imaging . . . etc. according to one or more embodiments shown and described herein.

Referring now to FIG. 1, the exemplary clinic layout 100 is generally rectangular or square in shape, having a main outer perimeter 102. The layout 100 includes a four corners design for ancillary components of this unique clinic design, with clinic space centralized between these components. This allows for more efficient coordination of multidisciplinary and multispecialty services and allows these services to be provided in one location, within a smaller footprint. The four corners include an urgent care space 104, a lab 106, an imaging center 108, and a pharmacy 110. The layout further includes two main entrances 112 and 114. The main entrances 112 and 114 include a waiting areas 124 and reception desks 128. Both main entrances 112 and 114 allow patients access to their desired service, either main clinic or ancillary services. This design provides patients with isolated and integrated care and utilizes unidirectional patient flow to increase healthcare delivery efficiency. The outer perimeter 102 of the layout 100 further includes exits 101A and 101B, which are configured to be exits only. In the present embodiment, the entrances 112, 114, are configured to be entrances only. The entrances and exits are stationed to be polar opposite sides of the structure, as located at 101A, 101B.

A medical clinic 100 is provided having a waiting room 102, reception 112, a lab 104, a plurality of primary care modular pods 106 (a pod is comprised of 4 exam rooms, a central workspace and collaboration station and access hallways), practitioner modular pods 108 (a pod is comprised of 4 exam rooms, a central workspace and access hallways), a pharmacy 110, entrance 120 and exit 122.

The urgent care space 104 includes an enclosed space set up similar to the primary care and specialty care pods. The urgent care space includes a center hallway 154 where care providers work. Patients are not permitted in the center hallway 154. A plurality of exam rooms 152 are positioned adjacent to the hallway 154. Each of the exam rooms 152 include two doors. One of the doors 150A is a dedicated door for patients. The other door 150B is a dedicated care provider door. Patients are not permitted to pass through the door 150B.

The lab 106 includes a lab reception area 106A where patients check in. The lab is an area where care provides can collect and test samples from patients including urine, blood . . . etc. Areas 106A, 106B includes exam rooms and bathrooms for sample collection spaced apart by a hallway.

The imaging center 108 includes a plurality of rooms for x-ray and ultrasound as shown at 160, 162. The imaging center includes two doors, both near reference numeral 108A to facilitate patient flow through the imaging center.

The pharmacy 110 includes a door 110A located near both a side exit and a main entrance so as to facility patient flow through the pharmacy.

Figure 2:
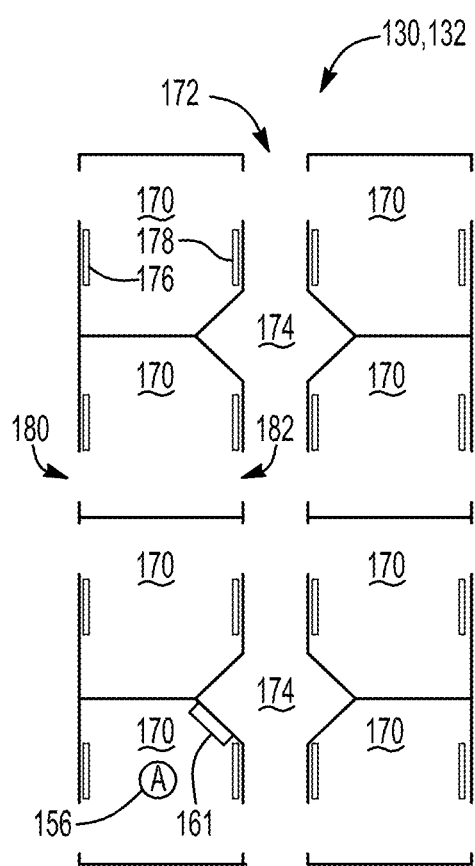
FIG. 2 depicts an exemplary pod (either primary care or specialist) according to one or more embodiments shown and described herein.

The layout 100 further includes a plurality of primary care pods 130 and specialist pods 132. Each of the pods 130, 132, as illustrated in FIG. 2, include a plurality of 8 exam rooms 170 each having a patient entrance/exit 180 and a care provider entrances/exit 182. The hallway 172 and the care provider space 174 is only accessible by the care providers, doctors, nurses . . . etc. The hallway 172 and the care provider space 174 shall not be accessible by any patients. The specific layout prevents unwanted interaction between care providers and patients by keeping the spaces that each party walks and moves separate. The patients go in and out of one door (180) and the care providers only go in and out of the other door (182). This specific layout prevents patients from overhearing care providers discussing the files and confidential information of other patients since only care providers are permitted in the hallway 172 and the care provider space 174. Each of the exam rooms 170 may further includes screen 161 and exam table/reclining chair 156.

It should be noted the layout 100 is nearly exemplary and not intended to limit the scope of the present invention. The layout 100 must comprise four corners and a plurality of pods, although the exact configuration, such as shown in FIG. 1, is not required and the specifics of each area may be adjusted in accordance with community needs.

Figure 3:
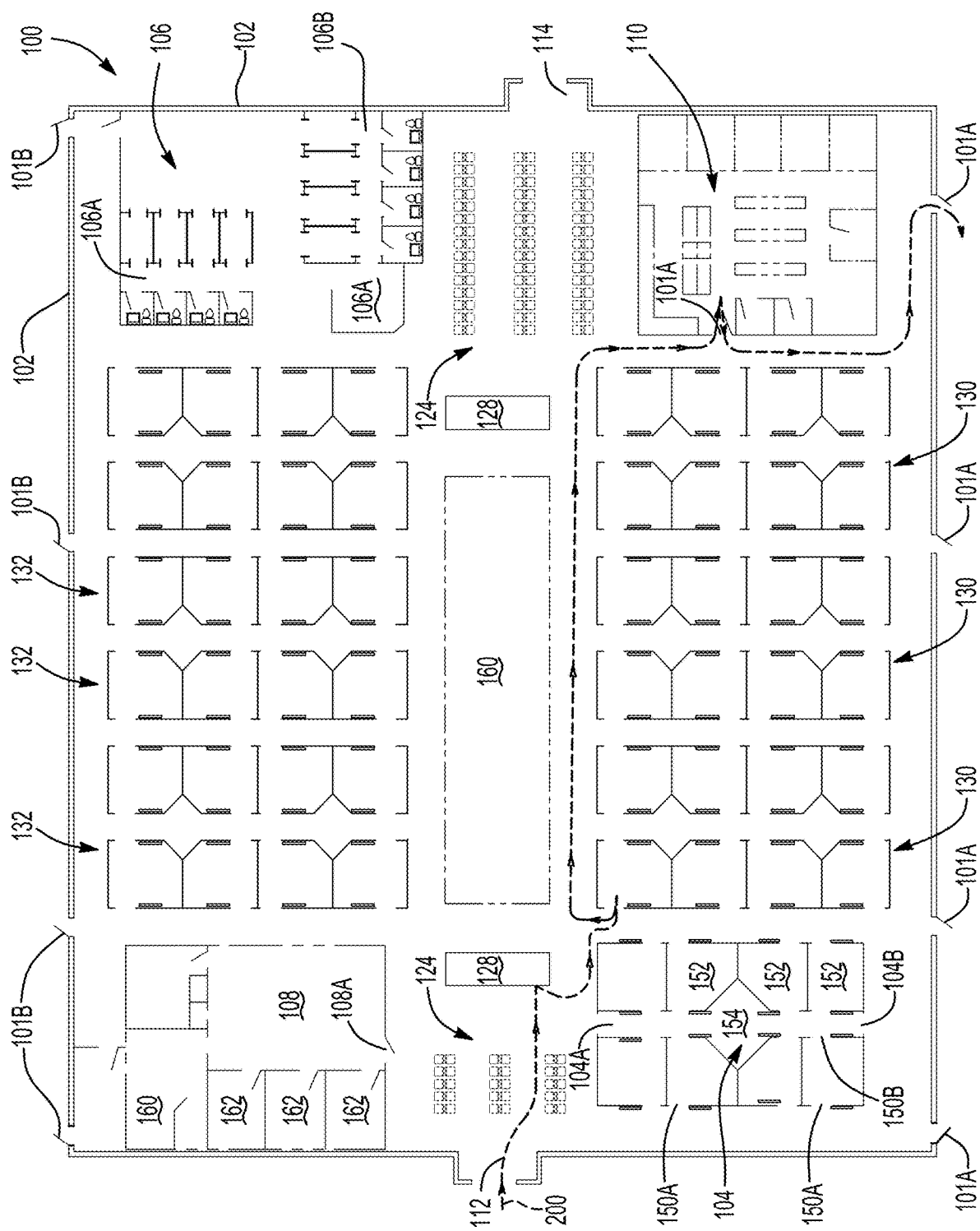
FIG. 3 depicts an exemplary building structure with illustrative flow arrows extending therethrough according to one or more embodiments shown and described herein.

FIGS. 3 through 7 illustrate exemplary paths taken by a patient when visiting the clinic 100. FIG. 3 depicts a patient path 200 wherein the patient enters the main entrance 112 and continues through the waiting area 124. After visiting reception 128 the patient moves to their designated primary care pod 130. The patient may then utilize the pharmacy 110 before exiting 122. Movement of the patient along the patient path 200 facilitates unidirectional patient flow through the clinic—in many variations this flow is clockwise throughout the clinic. The patient path 200 facilitates patient movement from the entrance 112 to one of the dedicated exits, in this embodiment, exit 101A, so as to increase clinic operational efficiency. This is further facilitated by the electronic standard adopted by the clinic, ensuring there is no need for patients to backtrack at any time, facilitated by a 3D rendering of the path to take through the clinic by the companion phone application.

Figure 4:
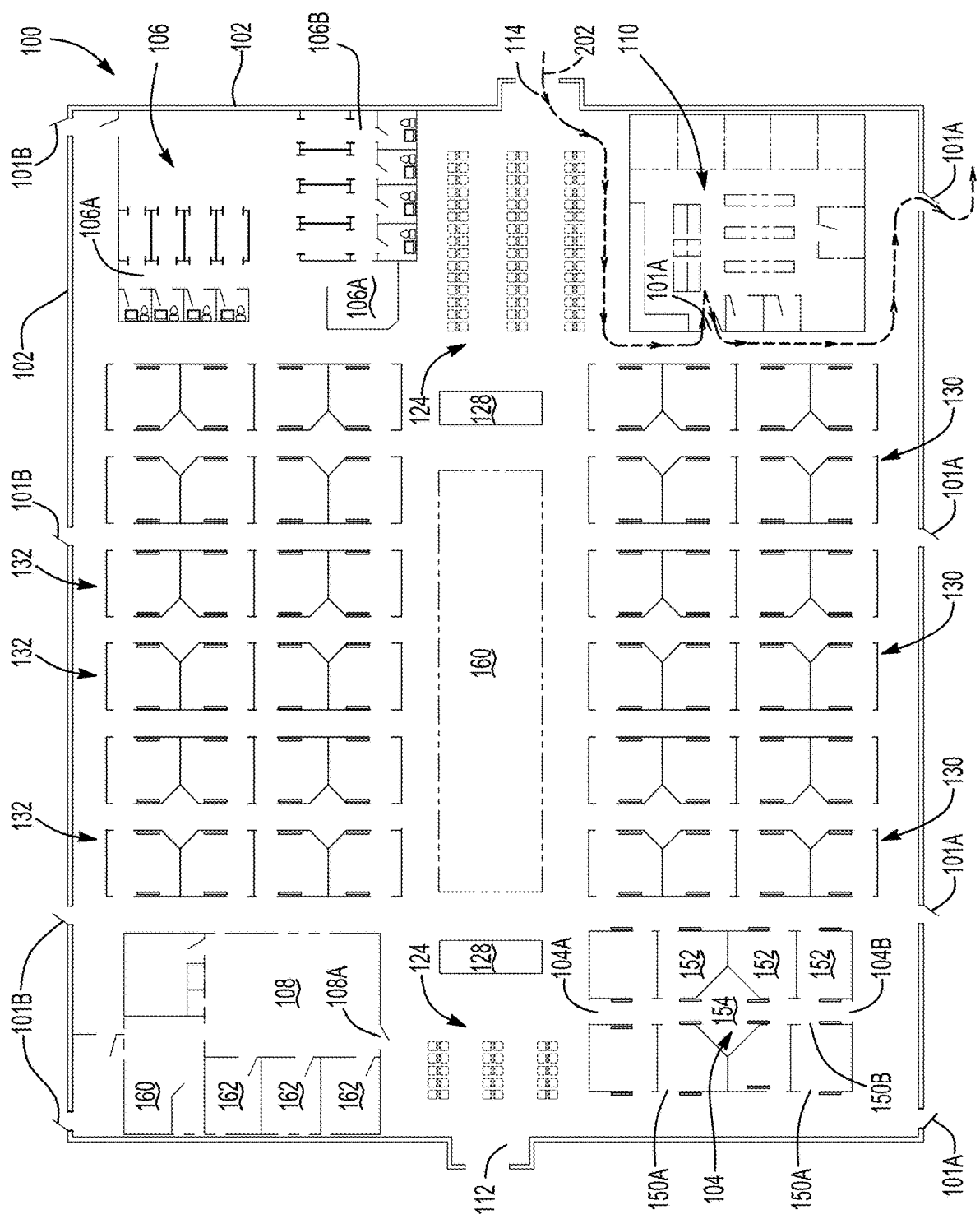
FIG. 4 depicts an exemplary building structure with illustrative flow arrows extending therethrough according to one or more embodiments shown and described herein.

FIG. 4 depicts an exemplary patient path 202 wherein the patient is only visiting the clinic to visit the pharmacy 110. In this embodiment, the patient enters the main entrance 114 and visits the pharmacy 110 before exiting the dedicated exit 101A.

Figure 5:
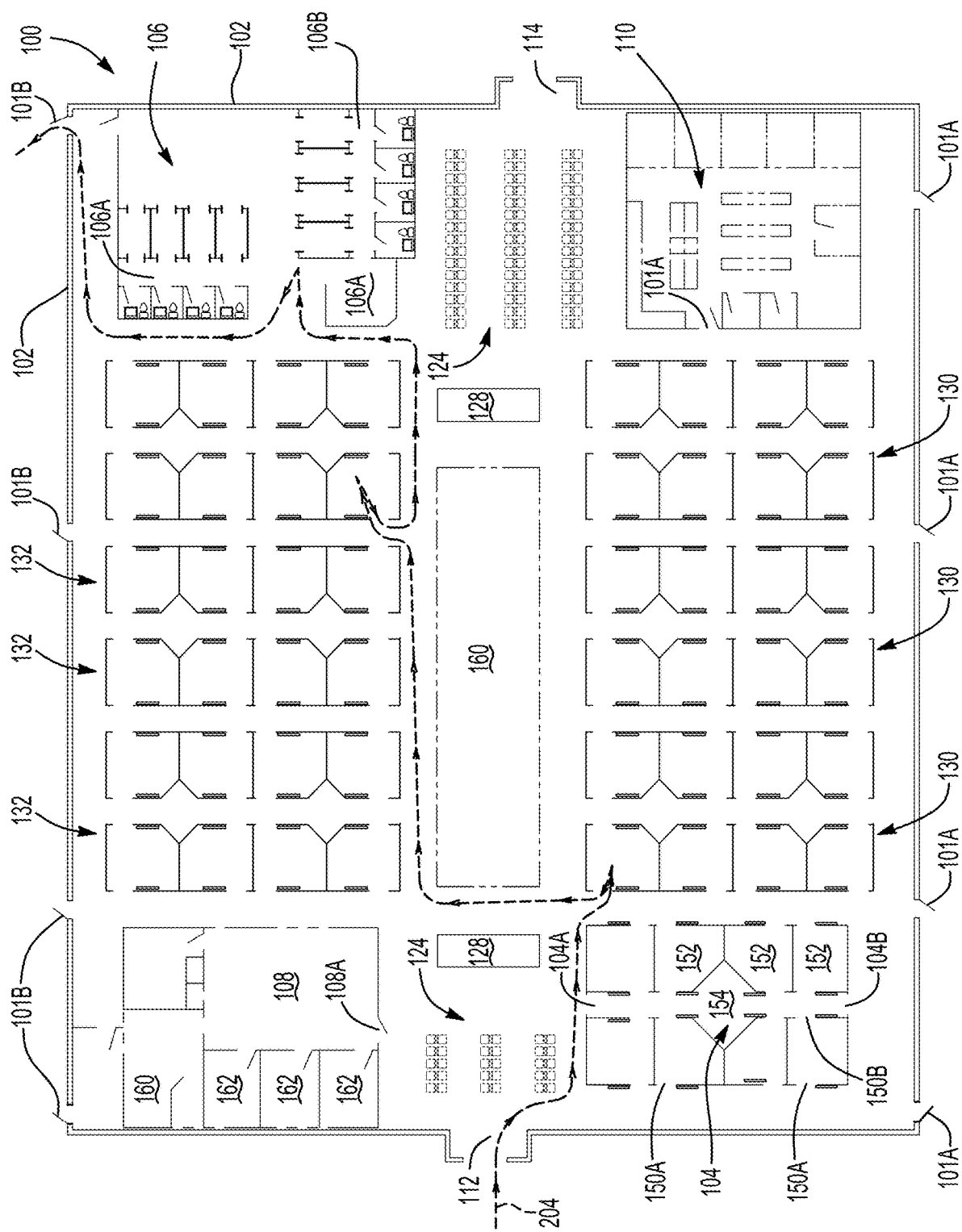
FIG. 5 depicts an exemplary building structure with illustrative flow arrows extending therethrough according to one or more embodiments shown and described herein.

Referring now to FIG. 5, a patient path 204 is provided wherein the patient enters the main entrance 112 into the waiting room 124. After visiting reception 128, the patient proceeds to a primary care pod 130. If needed, a specialist can be 'quick' consulted, and will come to the physician workspace using the clinic flow pattern and 3D rendered path to the desired consulting practitioner's pod entrance and workspace. Here the case can be discussed confidentially and if needed the consulted practitioner can enter the patient's exam room, providing patient-centered care. In the route as shown in 204, the patient then visits the specialist 132 in the same visit, or the specialist comes to the patient. The patient may then proceed to the lab 106 before exiting the building 101B.

Figure 6:
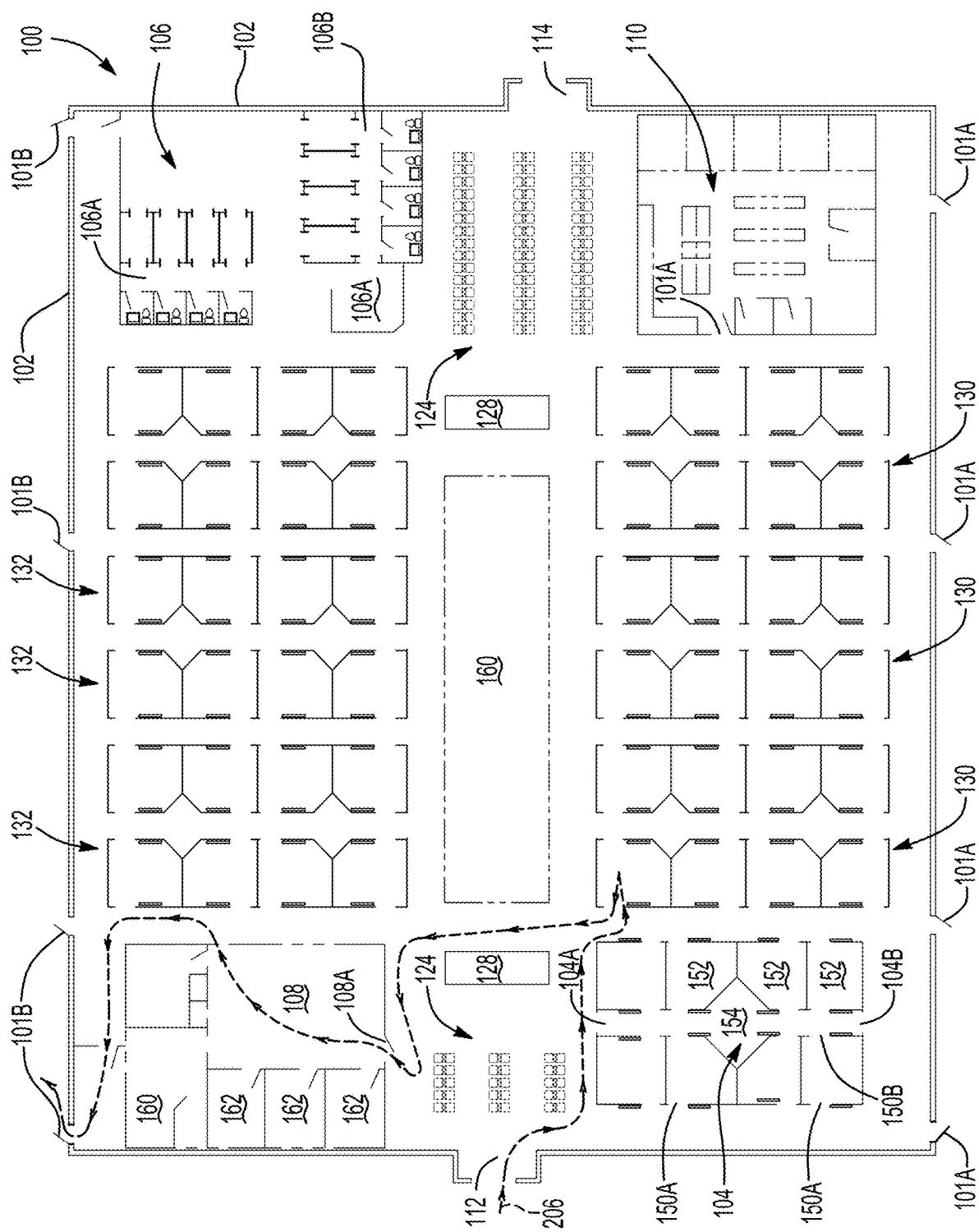
FIG. 6 depicts an exemplary building structure with illustrative flow arrows extending therethrough according to one or more embodiments shown and described herein.

FIG. 6 depicts a patient flow path 206 wherein the patient enters the clinic at the main entrance 112 and proceeds through the waiting room 124. After visiting reception 128 the patient proceeds to a primary care pod 130. The patient then visits the imaging center 108, and if needed, a specialist can be 'quick' consulted to see the patient in the imaging center, which will house additional pods, and patient exam rooms. The patient then exits the clinic at the dedicated exit 101B.

FIG. 6 further depicts a path at route 206. This route show the path of a person moving between exam rooms and through the hallway. The hallway extending between 104A and 104B is created to provide a path for physicians (and other staff) only and is intended to be a private and confidential area.

Figure 7:
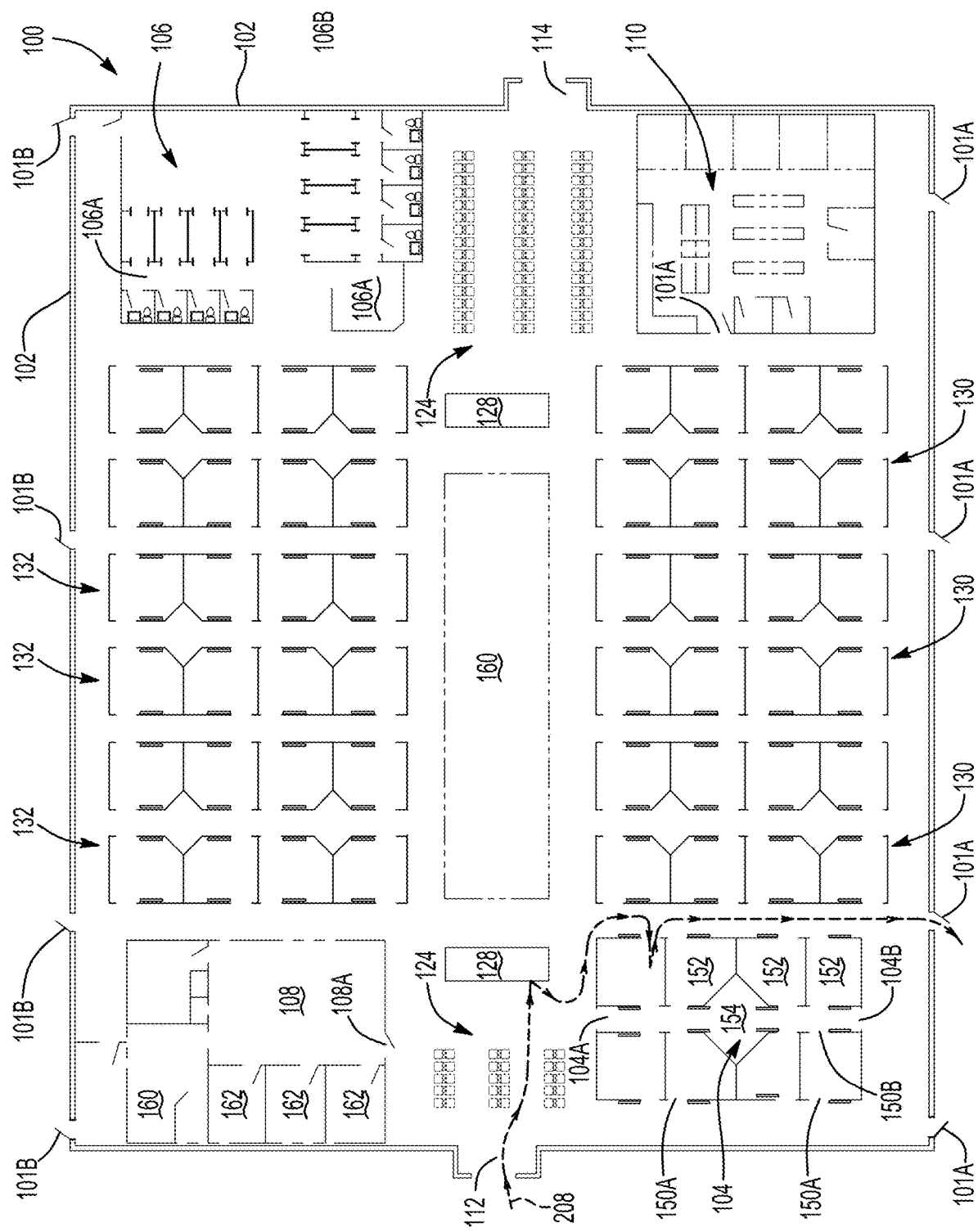
FIG. 7 depicts an exemplary building structure with illustrative flow arrows extending therethrough according to one or more embodiments shown and described herein.

Referring now to FIG. 7, a patient flow path 208 depicts wherein a patient enters the building through a main entrance 112 into the waiting room 124. After visiting reception 128, the patient may visit the urgent care 104 and exits the building through the dedicated exit 101A.

In some embodiments, a second and third floor may be provided on top of the first floor as illustrated in FIGS. 1 through 7. These additions can be added or omitted in a modular nature to suit geographical community needs. Similarly, a modular floor may be added for teaching, conference and private office use as needed. In order to provide adequate parking, while minimizing the facility's overall footprint, a parking garage will be available adjacent and connected to the main facility. The parking garage and elevators will provide multi-floor access to the main facility. The additional floors may include offices and a renal program/dialysis center accessible via the parking garage and elevators.

The clinic's lab will be available for immediate blood drawing prior to the patient's appointment. Analysis of the blood sample will take approximately 10-15 minutes and results will be electronically inputted into the clinic's EMR (electronic medical record). The results will be available to the healthcare provider that same day for assessment. This saves the patient a visit to separate medical laboratory, which is common practice, usually done one week prior to their clinic appointment.

Figure 8:
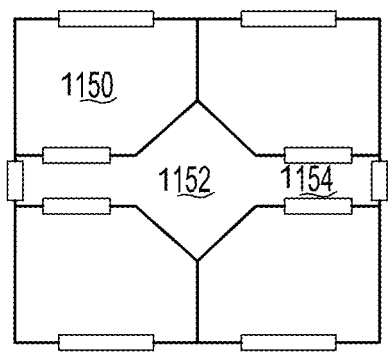
FIG. 8 depicts an exemplary exploded view of a single modular pod (comprised of 4 patient exam rooms and a dedicated work space) according to one or more embodiments shown and described herein.
Figure 9:
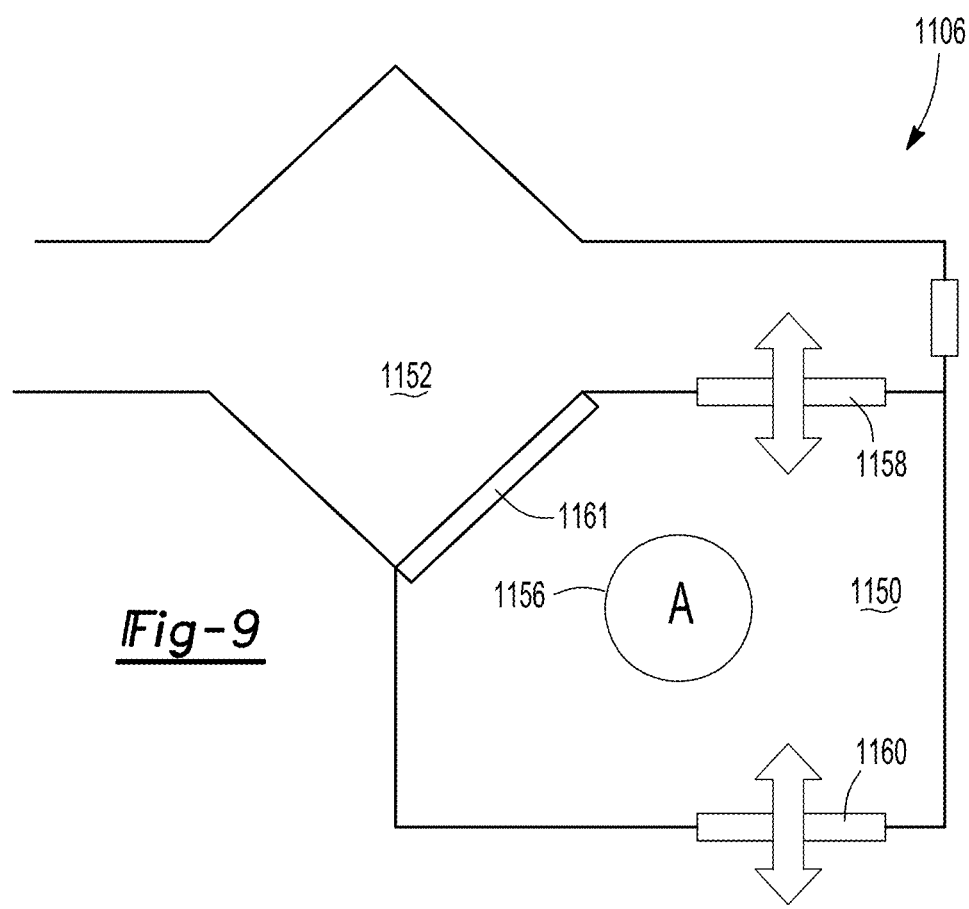
FIG. 9 depicts an exemplary exploded patient exam room and dedicated work space with access corridors designed according to one or more embodiments shown and described herein.

Now referring to FIGS. 8 and 9, each of primary care modular pods and the specialist modular pods include a centralized work area surrounded by four exam rooms, giving the provider(s) easy access to each exam room through the access hallways. Each of the exam rooms 1150 has a separate entrance/exit for the provider 1158 and a separate entrance/exit for the patient 1160. The provider also has a separate entrance/exit 1154 to the work area 1152. The plurality of entrances and exits (as shown by the plurality of doors in FIGS. 8 and 9) for the patients and physicians optimizes efficiency of the modular pods, and therefore the entire medical clinic. Each of the exam rooms in the clinic are compartmentalized, patient-centered, and facilitate a collaboration between healthcare providers and patients. Each exam room will have a unique and uniform design.

The pods are positioned adjacent to one another. Each of the pods has a hallway extending therethrough to optimize movement of healthcare providers between exam rooms, and to enable specialist physicians from other pods to easily access the pods 1106 for 'quick' consultation.

The joint specialist pods contain at least two work spaces for physicians. The dual workspace configuration allows two specialists to work directly adjacent to one another, allowing optimization of patient care. If, for example, the patient or physician wants a second opinion, a similarly specialized physician is available to immediately provide a second opinion. This method of providing second opinions can be applied to the primary care physicians as well. All physicians, both primary care and specialist, can utilize the centralized hallways connecting the work spaces and enter through the physician entrances, to increase efficiency of movement throughout the clinic.

Each exam room will have a dedicated area for the use of audio/visual presentation 1161 (FIG. 9), which allows the patient to see their laboratory values, imaging results, and question their healthcare provider with any concerns. This design allows the patient to be more involved in their healthcare decisions, and more informed about their condition. The audio/visual presentation 1161 (FIG. 9) will display educational material while the patient waits for the physician in the exam room. The use of audio/visual technology 1161 (FIG. 9) is also integrated with the use of the novel computer program and companion mobile device application. When a healthcare provider generates a QR code using the computer program, it will be displayed on the projection area for the patient to scan using the companion mobile device application.

The patient will scan the QR code giving them access to their problem list and educational materials, such as outlined and described in the forgoing description of the computer program and companion mobile device application. The QR code may also open a link to download/view additional information critical to the patient and patient care. The exam room will contain a single swivel, reclining examination chair in the center of the room, as well as a rolling chair for the attending physician. Other components standard and necessary in typical exam rooms may also be provided.

The medical clinic may also be equipped with a paging system as a backup system, to facilitate the 'quick' consult model, however this will routinely be done through the clinic software and phone application. In each exam room audio/visual educational material will be displayed on the screen 161 until the physician arrives. In this embodiment, the screen 161 is contained within the exam room. The screen may be any display screen, such as a monitor, projector or television, suitable to provide the relevant information to the patient.

In one aspect of the present specification, a means for enabling communication within the medical clinic regarding the occupancy of exam rooms is provided. The computer program will have a secure login for all clinic personnel (both support staff and healthcare providers). This function of the computer program can be described as a flow manager and will also facilitate the novel 'quick' consult model. This function will be available from the computer program home screen and when accessed can project to the screen. This screen will be accessible to all clinic members (both support staff and healthcare providers). By clicking the pictorial representation of an exam room, a clinic member will have the option to change the occupancy status of that exam room. The status options are: empty, filled-ready for nurse, filled-ready for doctor, filled-patient and doctor. The exam room statuses are color coordinated to make the status of the exam room visually detectable by clinic personnel. When an exam room's status is changed, the computer program will notify appropriate clinic personnel in two ways. The first notification method is a pop-up desktop notification, and the second is a mobile device notification. Combined, the flow manager, and notification systems will maximize clinic efficiency.

The next novel component of the flow manager is making the 'quick' consult model practical and functional. A healthcare provider will be able to select an exam room where they would like a colleague's consultation. Once the room is selected, a specific provider can be chosen for consultation. The provider chosen for consultation will then receive notification via the computer program in the form of a desktop notification and a mobile device notification. The practitioner providing the quick consult can navigate to the desired location using the 3-D rendered paths that are consistent with the flow patterns established for the clinic.

The computer program and companion mobile device application, such as illustrated in FIGS. 10-13, are essential to accomplishing the goals of the medical clinic by increasing productivity and improving patient health outcomes. The computer program and companion mobile device application work together to enhance coordination of care, increase patient involvement in care, while also providing helpful educational material, and simultaneously integrating clinic design with novel technology such as described herein and above. The problem list, medication list, educational material, appointment information and reminders will also be instrumental in increasing patient involvement, medication adherence and patient appointment compliance. These features are available to the patient through the companion mobile device application on the patient's personal mobile device. A detailed explanation of each component is found below.

Figure 10:
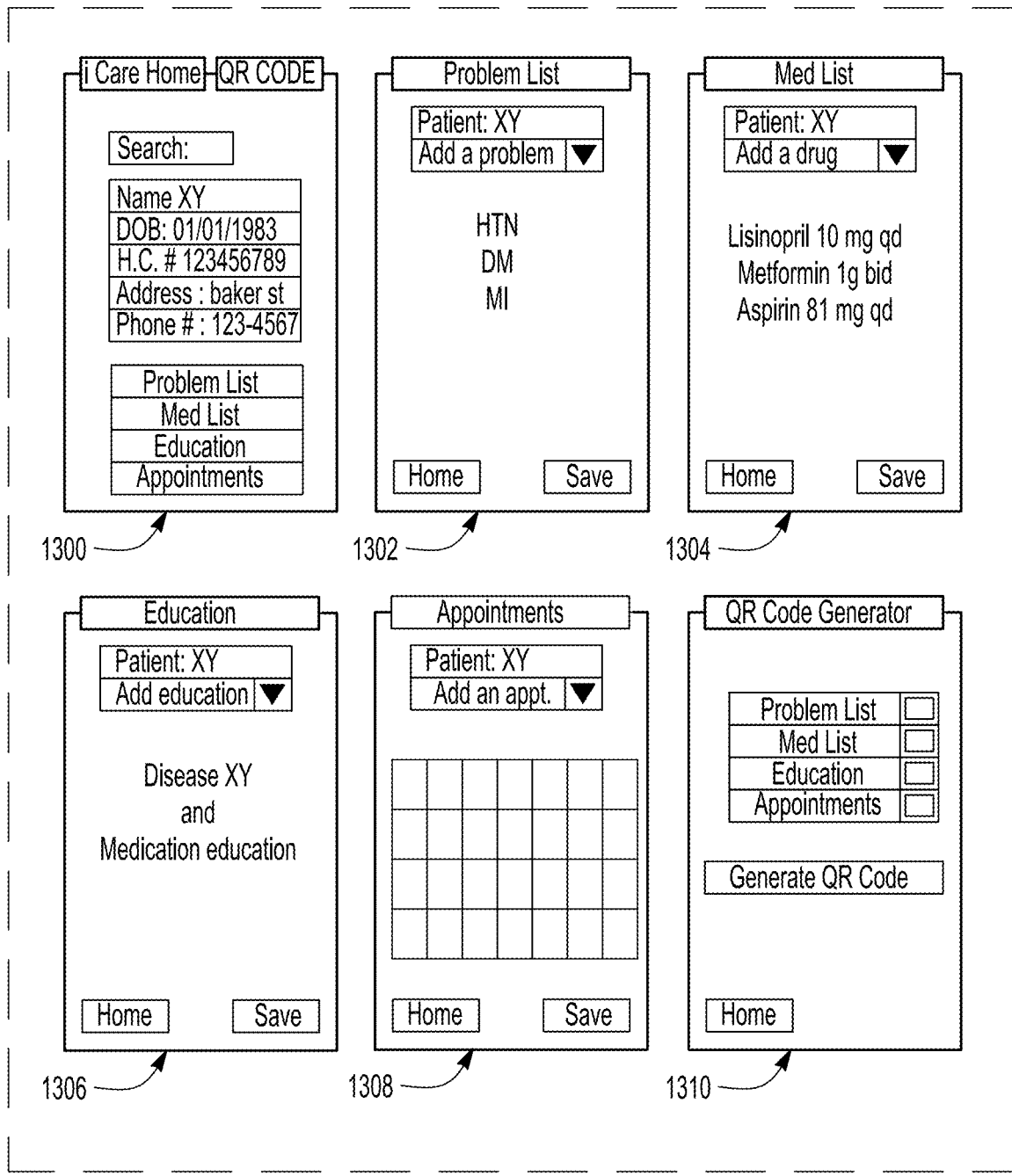
FIG. 10 depicts an exemplary screen shots of the computer program model showing information inputted by clinic personnel including patient identification information, problem list, medication list, educational material, appointments and the QR code generator according to one or more embodiments shown and described herein.

FIG. 10 illustrates the general interface of the computer program for healthcare providers and medical clinic personnel. FIG. 10 generally illustrates exemplary screen shots of the computer program. The first screen 1300 includes general biographical information such as the date of birth, address . . . etc. of the patient and accessible functions such as problem list, medication list, education, and appointments. This information is inputted by the physician or the medical clinic personnel. Screens 1302, 1304, 1306 and 1308 all illustrate areas for the healthcare team to input information such as the problem list, medication list, education and appointments, respectively. Screen 1310 illustrates the QR code 1254 generator.

FIG. 10 shows a general layout of the computer program, in which each clinic patient will have a profile with basic identification information (name, DOB, gender, address, phone number, health coverage identifiers . . . etc.). Within each profile, one of four functions can be accessed 1300. The functions include the problem list 1302, medication list 1304, education 1306, and appointments 1308. As described below, within each of these four categories, information can be selected/inputted by the health care team that is specifically suited to each patient. Once the information is inputted by the appropriate personnel, the information is saved to the patient's profile allowing a QR code to be generated and scanned by the patient via the companion mobile device application on the patient's personal mobile device. Once scanned the patient will have access to information and reminders that will increase patient involvement and improve health outcomes.

Figure 11:
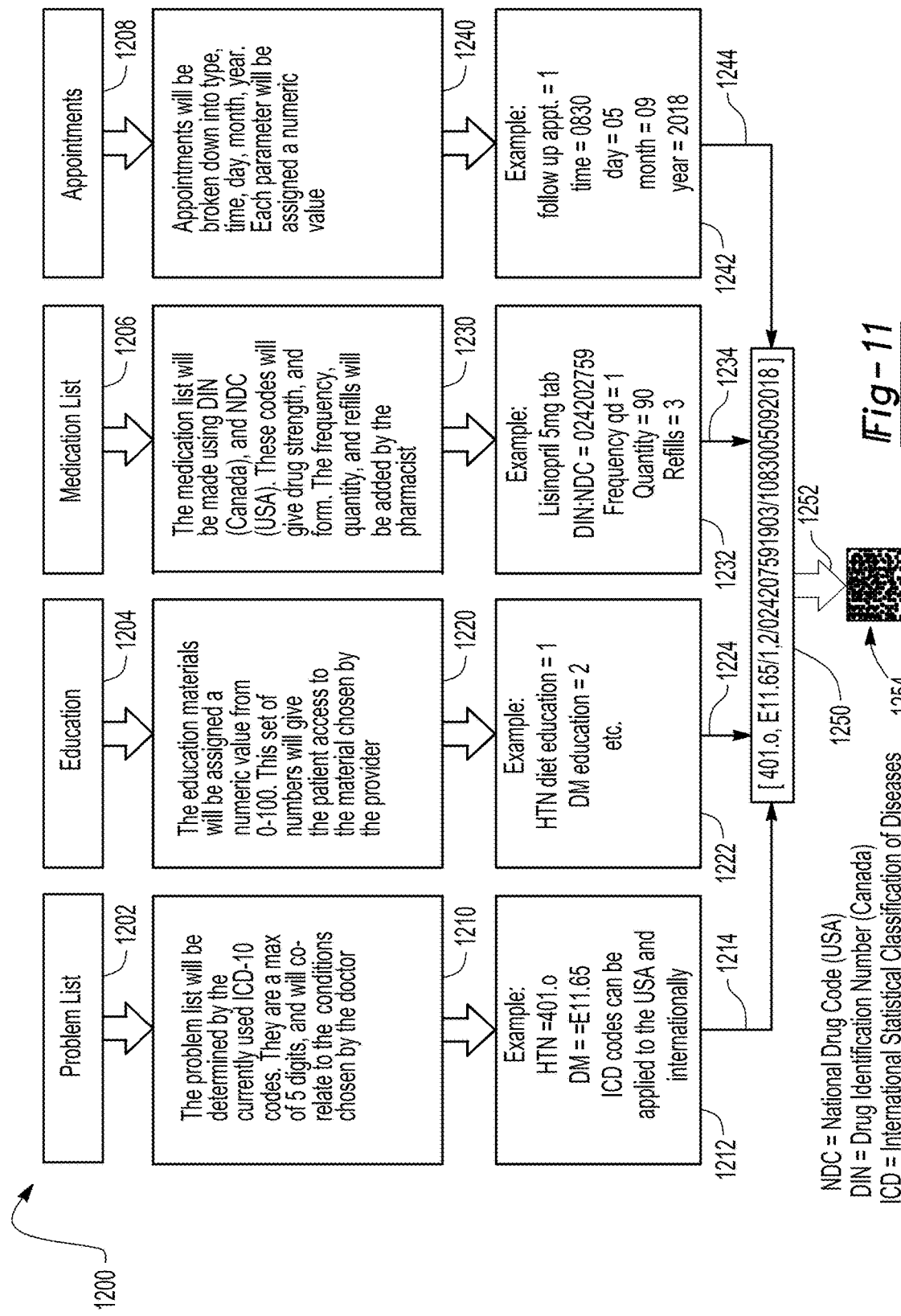
FIG. 11 depicts an exemplary flow chart of the computer program process of QR code synthesis according to one or more embodiments shown and described herein.

FIG. 11 illustrates a general process in accordance with the computer program QR code synthesis 1200. The problem list 1202 is inputted by the provider to grant the patient a current, inclusive problem list available to the patient on their personal mobile device via the companion mobile device application. The provider inputted problem list will computationally be translated to the appropriate, currently used ICD-10 (International Classification of Diseases) codes. This process is illustrated beginning at reference numeral 1202. An example of ICD-10 codes are provided in the flow chart of FIG. 11 at reference numeral 1212. The selected problems are inputted and converted to ICD-10 codes, then they are combined 1214 (as illustrated by the directional arrow) into the numerical code 1250. This numerical code 1250 is generated 252 into a QR code 1254, such as shown.

FIG. 11 further illustrates the education 1204 selected by the physician granting the patient access to the corresponding educational material on their personal mobile device via the companion mobile device application. The educational material is selected by the physician specifically suited to each patient. All distinct educational material will have an assigned numeric value as shown in reference numeral 1220. Reference numeral 1222 illustrates an example of these assigned numeric values. The provider selected educational material are computationally translated to their numeric value and combined 1224 (as illustrated by the directional arrow) into the numerical code 250. This numerical code 1250 is generated 1252 into a QR code 1254, such as shown.

A medication list 1206 is further provided as inputted by the pharmacist, granting the patient access to their medication list and compliance reminders on their personal mobile device via the companion mobile device application. As illustrated by reference numeral 1230, the medication list is formulated using DIN (Drug Identification Number—Canada) and NDC (National Drug Code—USA). These codes give the drug, strength and form. The quantity, dosing frequency, route of administration and refills may also be added to this information. An exemplary set of codes is provided at reference numeral 1232 showing an exemplary drug, strength, form, quantity, frequency, and refills . . . etc. The pharmacist will input the medication list which will be computationally converted into a unique numeric code and combined 1234 (as illustrated by the directional arrow) into the numerical code 1250. This numerical code 1250 is generated 1252 into a QR code 1254, such as shown.

FIG. 11 further illustrates the appointments 1208 are inputted by the physician or support staff and viewable by the patient on their mobile device via the mobile application. As illustrated at reference numeral 1240, appointments are broken down into type, time, day, month and year. To generate the QR code 1254, each parameter of the appointment is computationally assigned a numeric value. An exemplary set of numeric values is illustrated at reference numeral 1242. The appointments are inputted and computationally converted into a unique code and combined 1244 (as illustrated by the directional arrow) into the numerical code 1250 This numerical code 1250 is generated 1252 into a QR code 1254, such as shown.

Collection of data as outlined above and as outlined in FIG. 10 and FIG. 11 allows the computer program to generate the QR code 1254 that is readable by the companion mobile device application. The QR codes 1254 are made available to the patient in the exam room, at reception, or in the pharmacy, electronically or in any way deemed effective and efficient.

Figure 12:
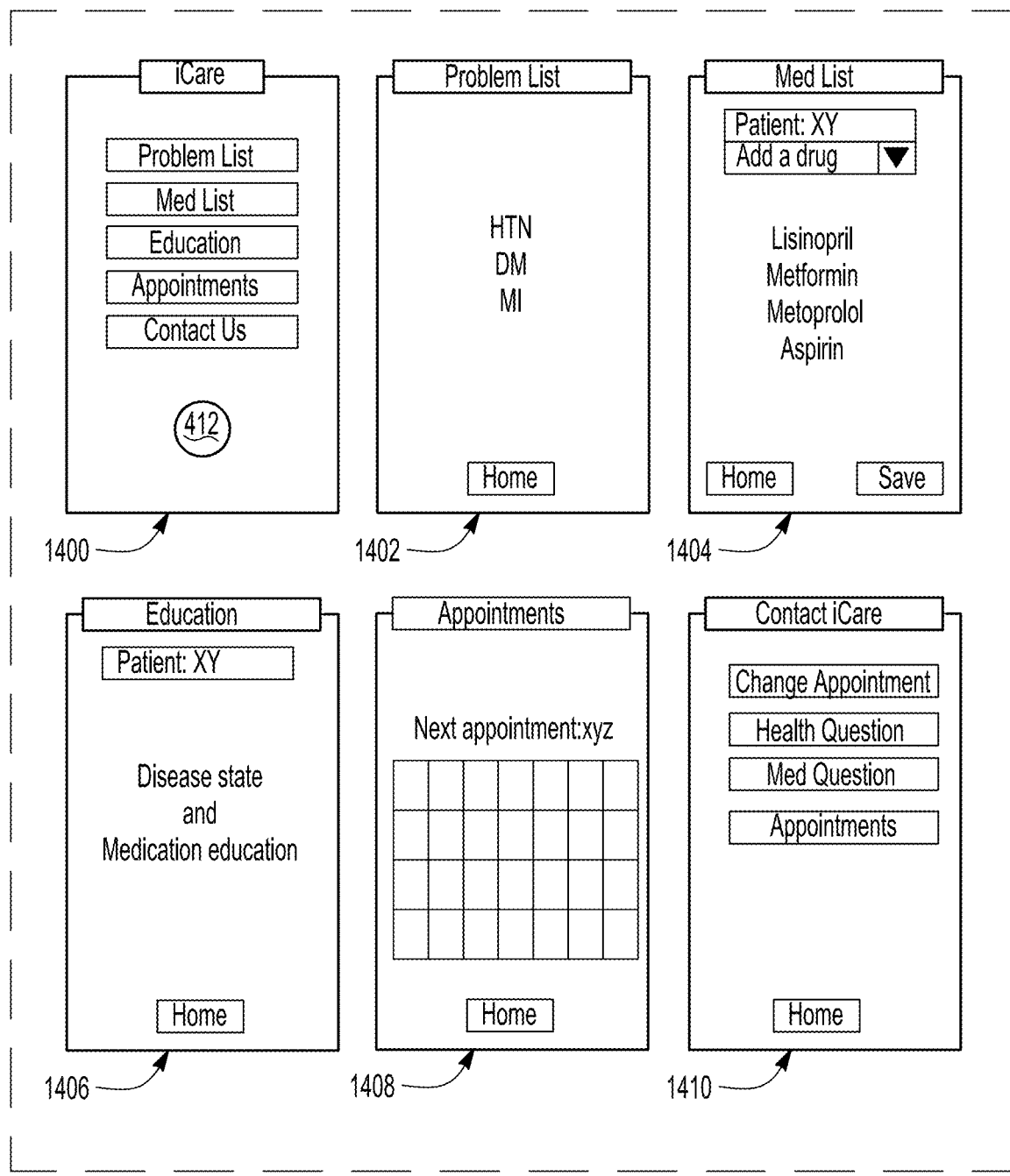
FIG. 12 depicts an exemplary screen shots of the companion mobile device application model including information accessible to the patient such as, but not limited to, problem list, medication list, educational material, and appointment information according to one or more embodiments shown and described herein.
Figure 13:
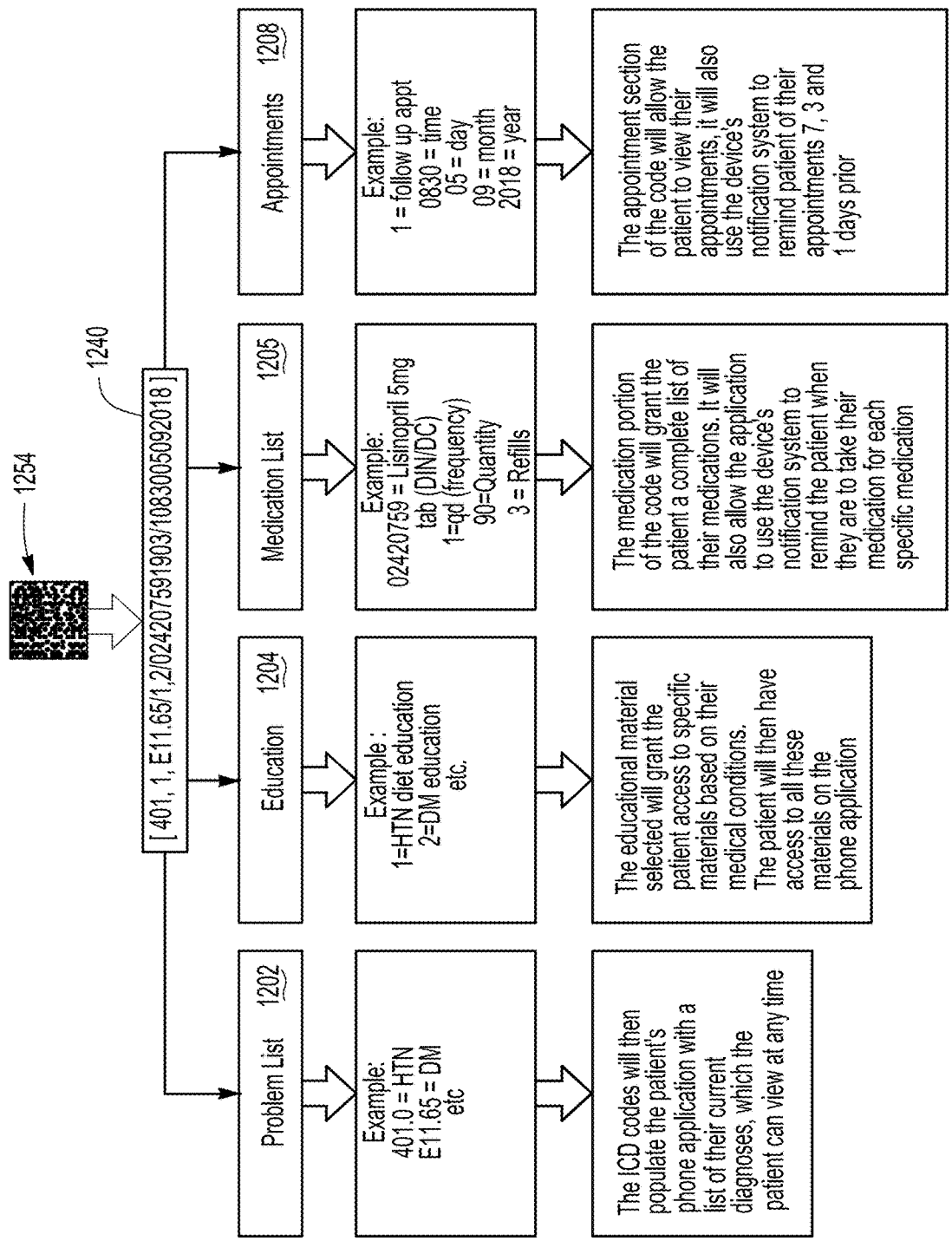
FIG. 13 depicts an exemplary flow chart of the process of decoding of a synthesized QR code by the companion mobile device according to one or more embodiments shown and described herein.

FIG. 12 illustrates the general user interface of the companion mobile device application. Screen 1400 having the button 1412 (to enable the camera to capture the QR code). Screen 1400 also enumerates the selectable options of problem list, medication list, education, appointments or contact us. Screen 1402 illustrates the problems list, screen 404 illustrates the medication list 1404, screen 1406 illustrates the educational material available to the patient, screen 1408 depicts upcoming appointments and screen 1404 shows contact options.

The companion mobile device application utilizes the camera function 412 in virtually all mobile devices to read the QR code 1254. Upon downloading the companion mobile device application, the patient will be able to scan the QR code 1254 provided to them by clinic personnel. The companion mobile device application will open with the camera function enabled. The user can tap the circle 1412 while the camera is in view of the QR code 1254 to allow for QR code decoding. The companion mobile device application will automatically populate with the information (problem list, medication list, educational material, and appointments) attached to that unique QR code. The information previously translated into the QR code 1254 will be accessible to the patient within the companion mobile device application. The companion mobile device application will subsequently provide helpful reminders for medication adherence, medication refills, and appointments. The companion mobile device application will access the devices' notification system and remind patients of upcoming appointments 7 days, 3 days, and 1 day prior to their appointment. This allows for more efficient use of office staff time by eliminating the need to make appointment reminder calls, while enhancing appointment attendance. The application will also provide medication adherence reminders. The reminders will be specific to the drugs and medication schedule that the patient is prescribed. This will improve adherence to therapies known to improve patient health outcomes. Furthermore, the companion mobile device application will have a function allowing the patient to contact the clinic via email 410. This function will be stratified, allowing the patient to select the general purpose of their inquiry. Each selection will open a template email and allow the patient to send their comment/question/concern to a generalized email account(s) and include their phone number for correspondence. Emails will be sorted by importance and urgency, and promptly responded to accordingly. The companion mobile device application will eventually be developed to allow the patient to track their home health information, such as blood pressure, blood sugar readings, etc. and pertinent clinical laboratory parameters. That same patient-specific QR code For that visit, will allow access for the patient to the physical plant at the parking gate and allow touchless entrance Into elevators, interior and exterior entrance doors and Clinic 3-D navigation systems. For any visit, the generated QR code will allow access for the patient to the physical plant at the parking gate and allow touch less entrance Into elevators, interior and exterior entrance doors and Clinic 3-D navigation systems.

Score Generation and Objective Scheduling

Referring now to FIGS. 16-26, score generation and calculation is described in detail. A comorbidity score is generated as a first step in the present system. A processor generates a comorbidity (COM) score based on a number of different inter-related systems that add to a patient's overall morbidity in either additive or exponential fashion. An example in the cardiovascular system would be the combination of problems such as those known to contribute to cardiovascular disease burden. The presence of multiple involved systems (cardiac, renal, neurological, vascular, medical and metabolic and pulmonary) that are listed in their standardized problem list that is used for all patients across all specialties, are used to generate a COM score.

At the time of each assessment or review of status by the most responsible practitioner in each field (for both primary care and specialty care), a specialty acuity score is generated (by practitioners in each field involved in the patient's care) from 1 to 6 based on their likelihood of needing to use the emergency room or requiring a hospital admission. This specialty acuity score is based on having zero or more of the multiple clinical features in each specialty selected from a standardized checklist for each specialty most predictive of a poor prognosis reflective of a higher likelihood of requiring emergency room assessment or hospital admission. A Specialty Acuity (SPA) Score is then generated (as illustrated in FIGS. 16 and 16A).

Figure 16:
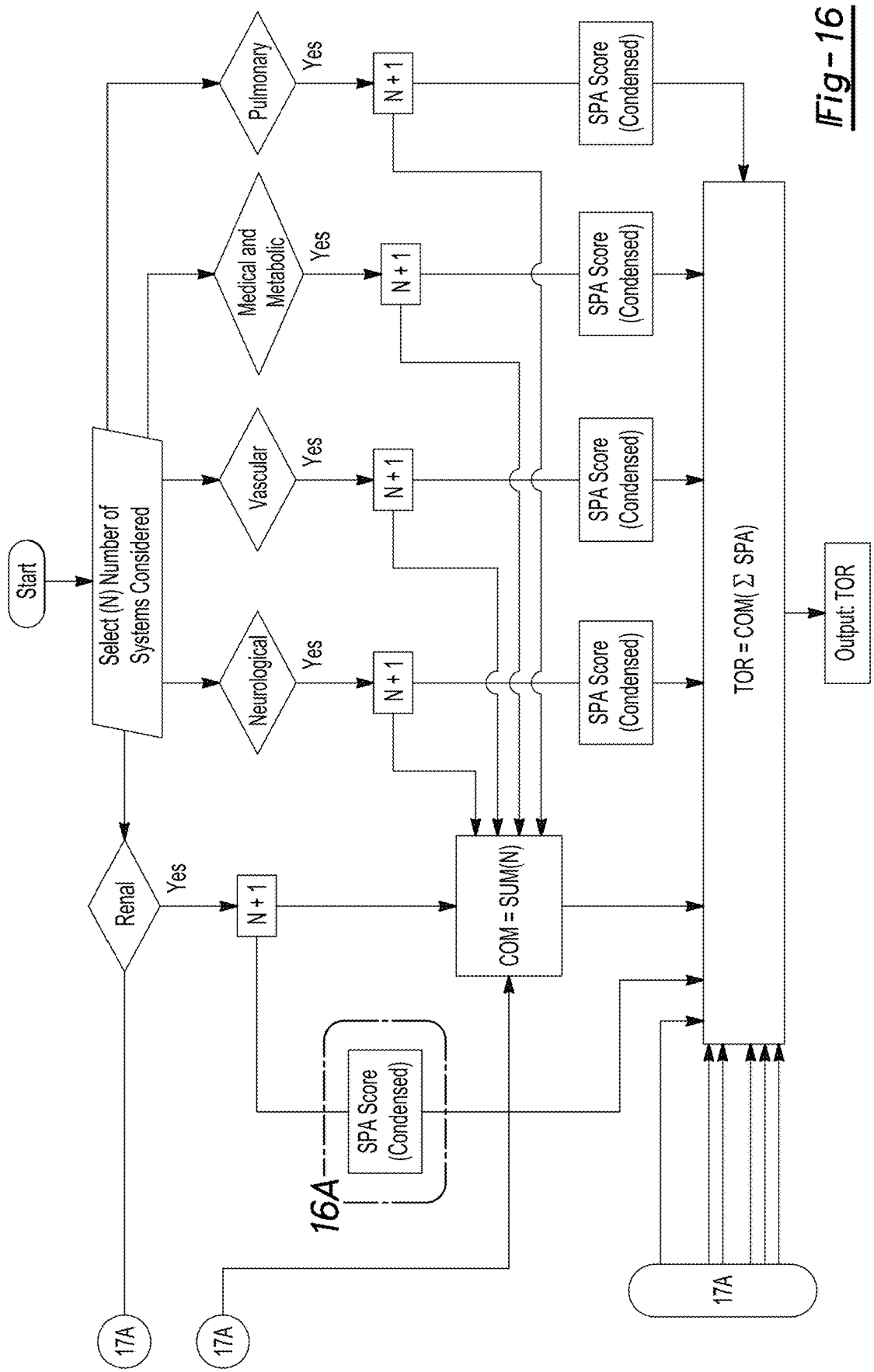
FIG. 16 depicts a flow diagram for determining a SPA score according to one or more embodiments shown and described herein.
Figure 16A:
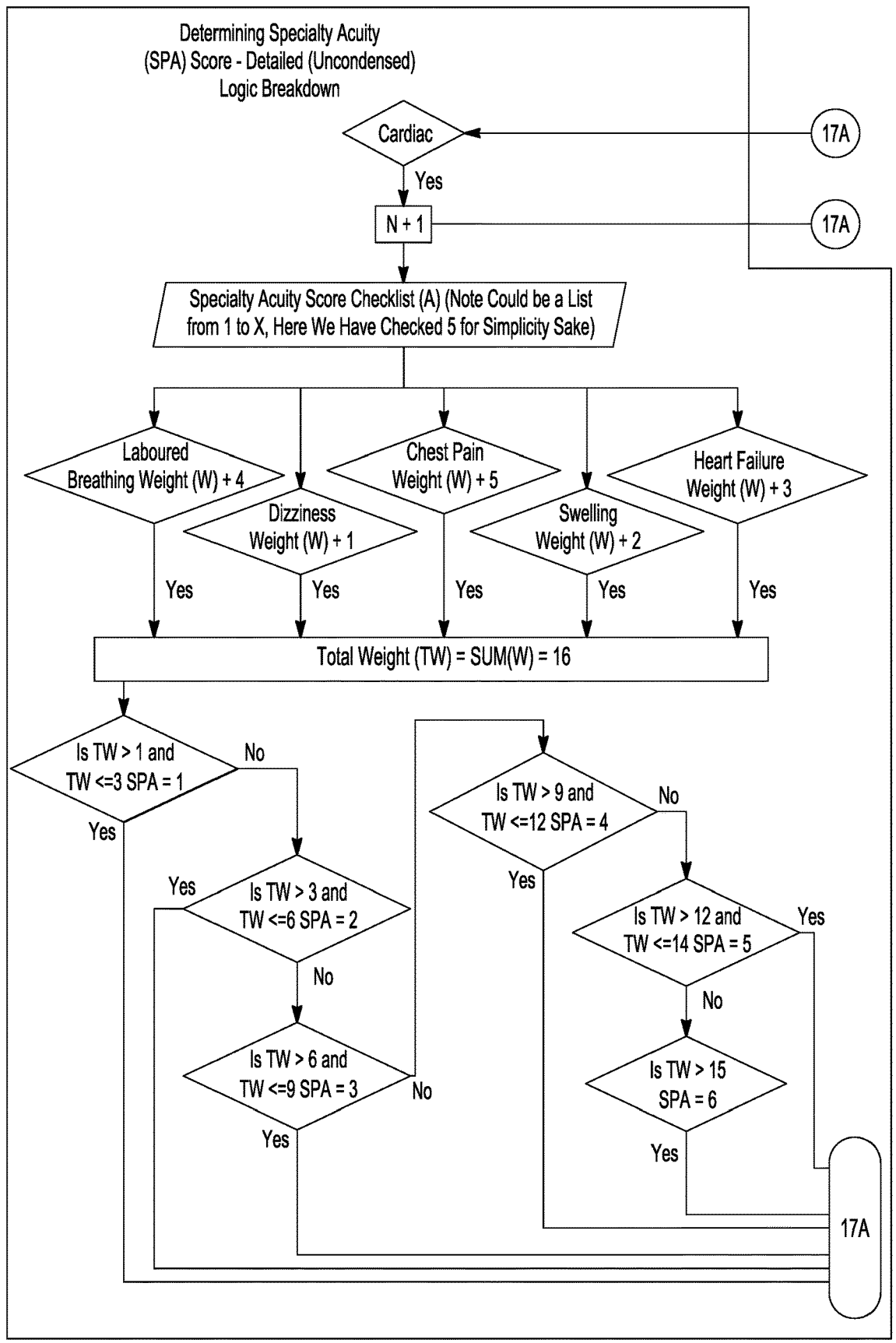
FIG. 16A depicts a continuation of the flow diagram as shown in FIG. 16 for determining a SPA score according to one or more embodiments shown and described herein.

Referring now to FIGS. 16 and 16A, a process of determining a SPA score, a COM score and a TOR score is herein described. As shown in FIGS. 16 and 16A, the process starts by entering data including neurological, vascular, medical or metabolic, renal, cardiac or pulmonary. By way of example, we look to the process for cardiac SPA score determination. Based on data input into the system, in the format of a checklist, the total weight is determined. in the embodiment as illustrated in FIG. 16A, the total weight for this individual is 16. The system then proceeds to compare the total weight with a predetermined factor to determine the SPA score. Once the SPA score is determined, the comorbidity score can then be determined. It should be noted that the term comorbidity is abbreviated in this specification COM. The Tor score is then generated by multiplying COM score by the sum of the SPA scores. This TOR score can be used to determine scheduling and overall health or urgency of a patients visit.

The SPA score used by each most responsible primary care and specialty practitioner involved in the patient's care will be standardized. It is based on the presence or absence of the most predictive signs or symptoms of poor prognosis and the potential need for emergency room use or hospitalization within a few days to up 6 months (or more). These prognostic features will be weighted for impact and will be based on the most up to date data and clinician consensus within that field and can be adjusted as new data becomes available. This some of the weighted prognostic features will factor into determining the SPA score category for that patient as illustrated below.

The SPA score for a predetermined field is used to determine a standardized scheduling frequency in the clinic for stable patients to see their primary care and specialist practitioners at regular overlapping intervals. The computer program will then create quick consult appointments for those specialties as mandatory for any specialty with a SPA of > or =5 as well as to meet the standard predetermined requirements described above. At any visit, based on clinical judgment, a quick consult can be obtained by request to any other area of specialty. The program will differentiate whether the quick consult is due to high acuity score or required routine follow up or by a clinical judgment request.

The comorbidity (COM) score is multiplied by the sum of the specialty acuity (SPA) scores to calculate a total overall risk (TOR) score.

$$TOR=COM(\Sigma SPA)$$

The TOR score will be utilized in a standardized fashion to facilitate nurse practitioner and allied health care assessments for high risk patients as well as a SPA score multiplier for medical practitioner assessments to reflect the priority of more complex patients with multiple medical problems co-existing.

The higher the TOR score, the earlier follow-up will be booked in a standardized fashion with allied health care and priority specialties based the highest SPA scores to give priority to those patients needing care faster in an objective manner. For any given specialty there will be regularly scheduled follow-up based on the specialty acuity (SPA) score. Based on priority, the most immediate follow up is objectively booked by the specialty who has the highest SPA score. If more than one specialty has the same SPA score for the patient, they are booked with the specialty who has the highest weighted score from the standardized checklist factoring into the SPA score. The patient will be given 3 options for booking with their MRP specialist with the highest SPA score who is available at the patient's preferred booking time and the other specialist(s) will be automatically quick consulted. Any acuity score of 5 or clinical judgement, generates an automatic quick consult to any other specialty. Clinicians can override and ask for a quick consult at any point in time regardless of risk score if there is a concern.

The Program and Role of Each Most Responsible Practitioner (MRP)

Most patients prefer to maintain oversight of their care with their most responsible practitioner (hereinafter referred to as "MRP"). The scheduling method and system of the present specification will search each MRP's schedule to try and book each follow up by priority assignment with that specific MRP and try and match the highest acuity scores to ensure as many MRP's that are present in the clinic at their suggested booking times based on their highest acuity scores. If at that time the patient needs an assessment by a specialist physician that is not their MRP, this can be done by a covering practitioner but the MRP would be responsible for approving any changes. All investigations or orders on any patient of are always sent to their MRP for review and approval if they are available. If urgent or the MRP is unavailable, the covering practitioner in that specialty will approve the investigations/orders.

In some embodiments, a patient can book with any practitioner with the same priority SPA score that is available at the time they are able to return. This process gives complicated patients multiple options for rebooking. The computer system and method coordinates these bookings based on searching the schedules of their most responsible practitioners. If none of their highest SPA score practitioners are available, they can book with the next available practitioner in that specialty, but all information must be reviewed and approved by their MRP. All changes made by any practitioner who sees them by quick consultation who is not their MRP must be approved by their MRP in that area and the computer program coordinates this. This allows shared care but accountability directly to the patient by their own family doctor and their own specialist practitioners.

EMR Program Laboratory/Investigations Coordination

The system and method of some embodiments organizes both stat lab/investigation and routine lab/investigation scheduling to avoid duplication of tests and multiple visits to the lab or imaging facilities. The frequency of visits based on the TOR/SPA scores and clinical judgment will be at 1 day, 2 days, 4 days, 8 days, 2 weeks, 4 weeks, 8 weeks, 16 weeks, 32 weeks, 64 weeks. The system and method of some embodiments will generate a single lab/investigation list based on the requests of all practitioners for that patient and the time intervals for each practitioner's routine follow up frequency (also determined by the program based on that specialty's SPA scores) and generate a single set of tests to be done before each visit with copies to go to all practitioners involved in the patient's care for review. The verification of routine investigations is required by all most responsible practitioners involved in the patient's care. Any STAT labs/investigations can be entered at any time based on the needs of the patient and are copied to all practitioner's involved in the care of the patient. The responsibility for verifying STAT labs is with the ordering practitioner. The program will differentiate between STAT investigations and routine investigations when sent to a patient's practitioners.

The above is combined with lab/investigation appointment and scheduling into the same system and method.

Patients investigations done at the single-site multi-specialty clinic are done the same day/visit. The program (EMR) coordinates the scheduling to provide the same day clinic visit with investigations performed in the lab and imaging facilities on the same day prior to the scheduled visit.

The specialty with highest priority SPA score gets the primary booking with other specialties available that may or may not be their MRP in these areas, but their MRP must approve any changes.

This program can be used across sites and can determine the need for video conferencing from remote sites for specialty or primary care bookings at different locations as long as the program (EMR) is shared across these locations.

Multi-Disciplinary Allied Health Care Booking

In most outpatient clinical settings, the use of allied healthcare professionals such as dietitians, pharmacists, social workers, etc., are not used on a priority basis and funding formulas for their use do not take into account patient care needs in a standardized fashion, nor are they shared across clinical specialties in a multi-specialty clinic.

Figure 17:
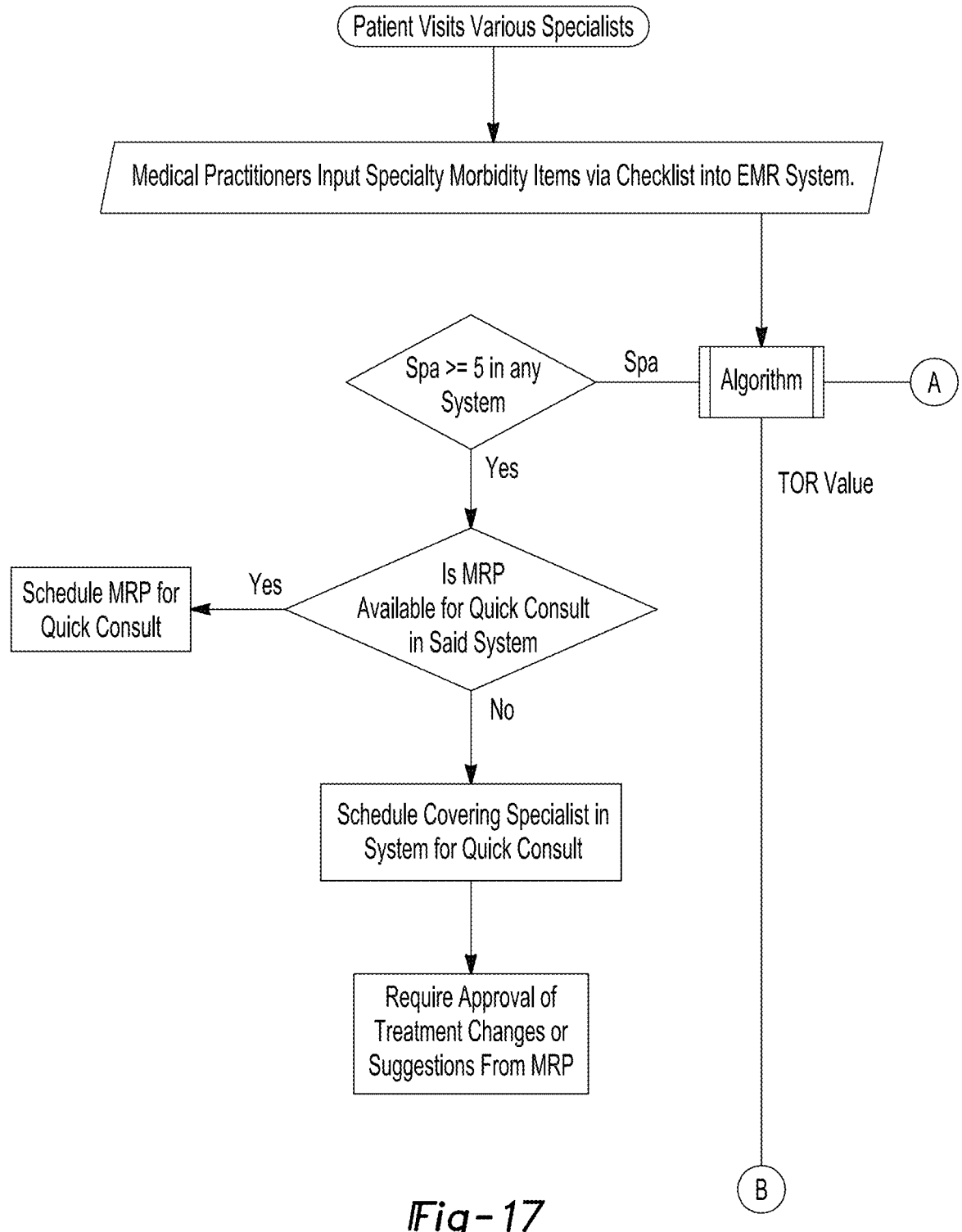
FIG. 17 depicts a flow diagram for determining scheduling based on a SPA score according to one or more embodiments shown and described herein.
Figure 17A:
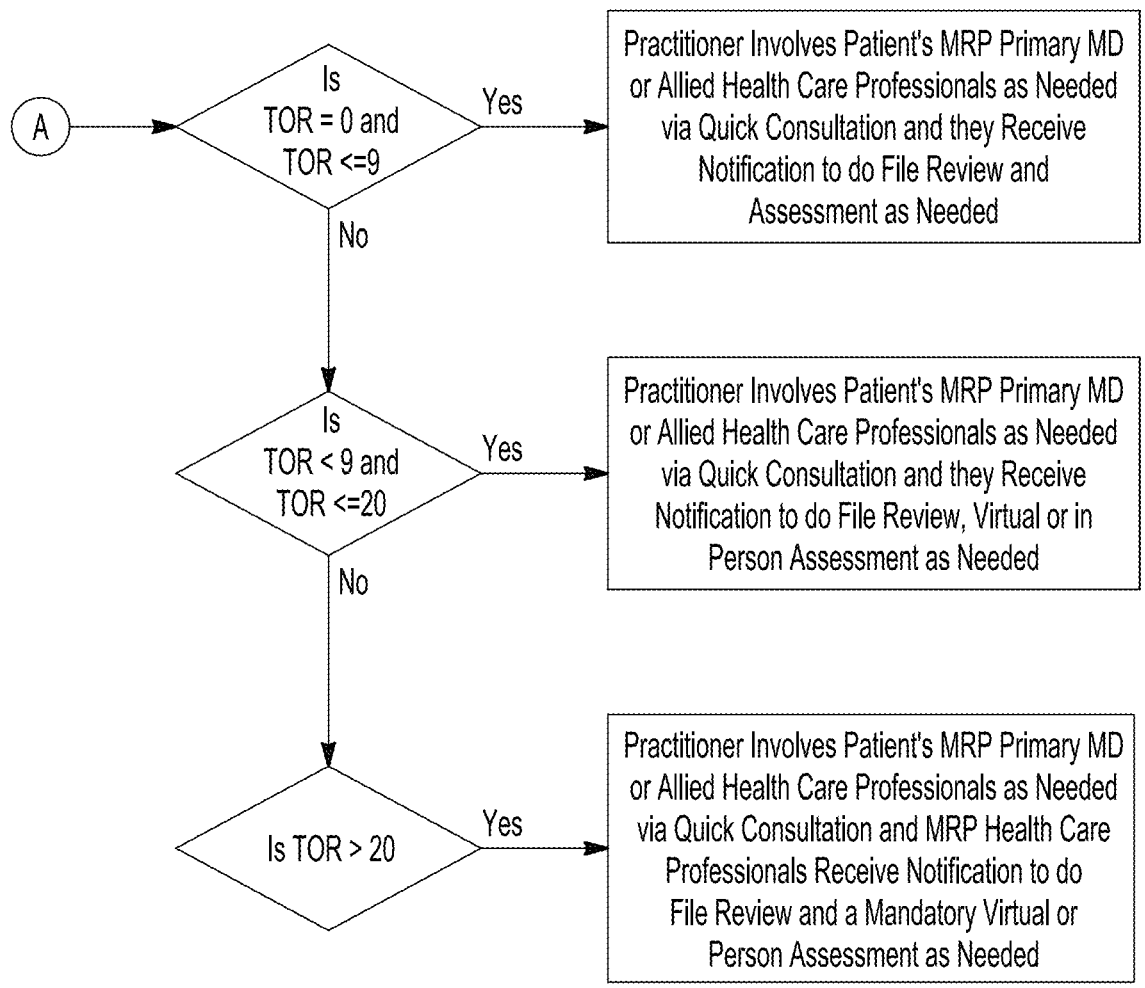
FIG. 17A depicts a continuation of a flow diagram for determining scheduling based on a TOR score which is derived using the SPA and COM score according to one or more embodiments shown and described herein.
Figure 17B:
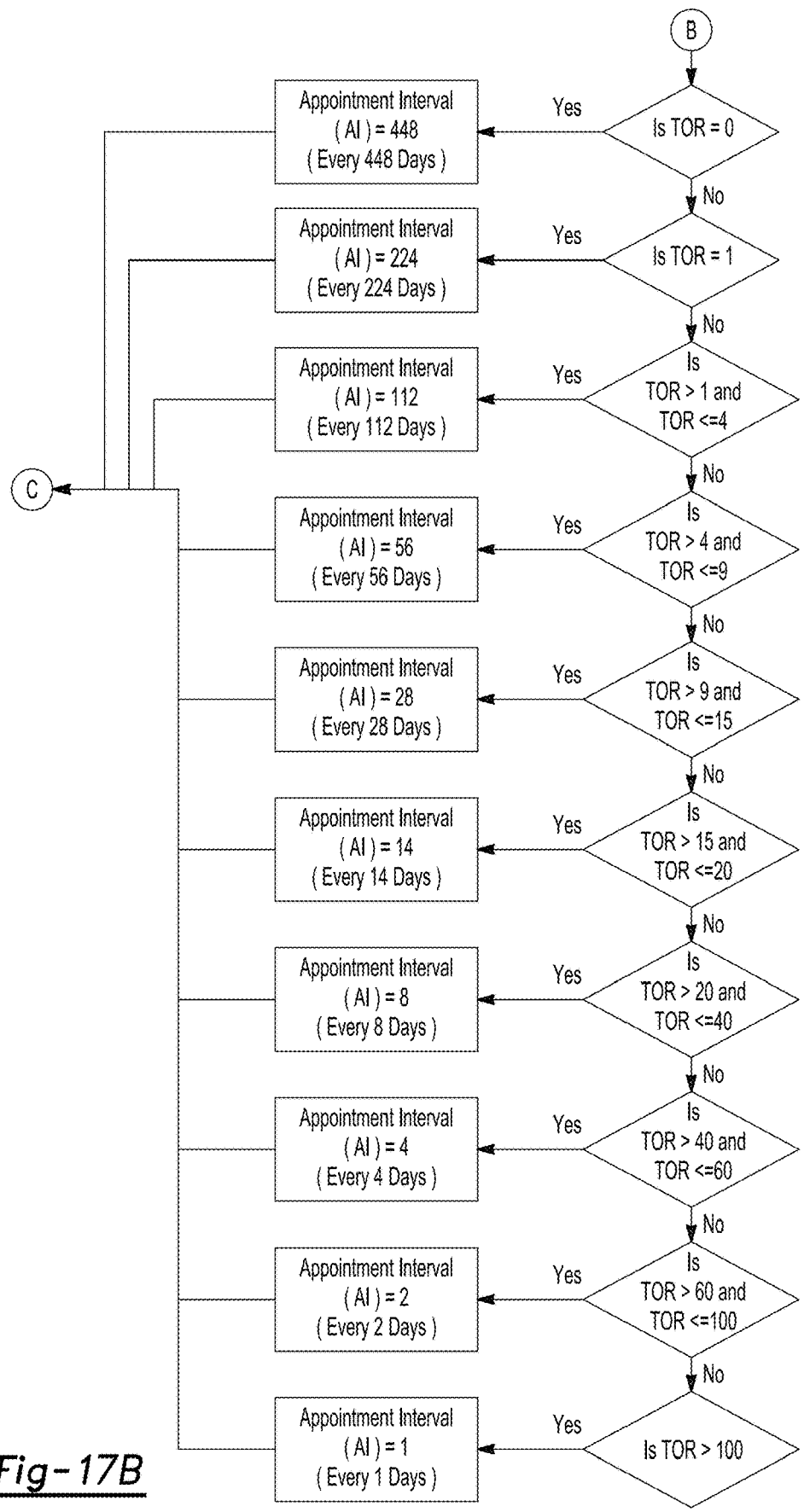
FIG. 17B depicts another continuation of a flow diagram for determining scheduling based on a TOR score which is derived using the SPA and COM score according to one or more embodiments shown and described herein.
Figure 17C:
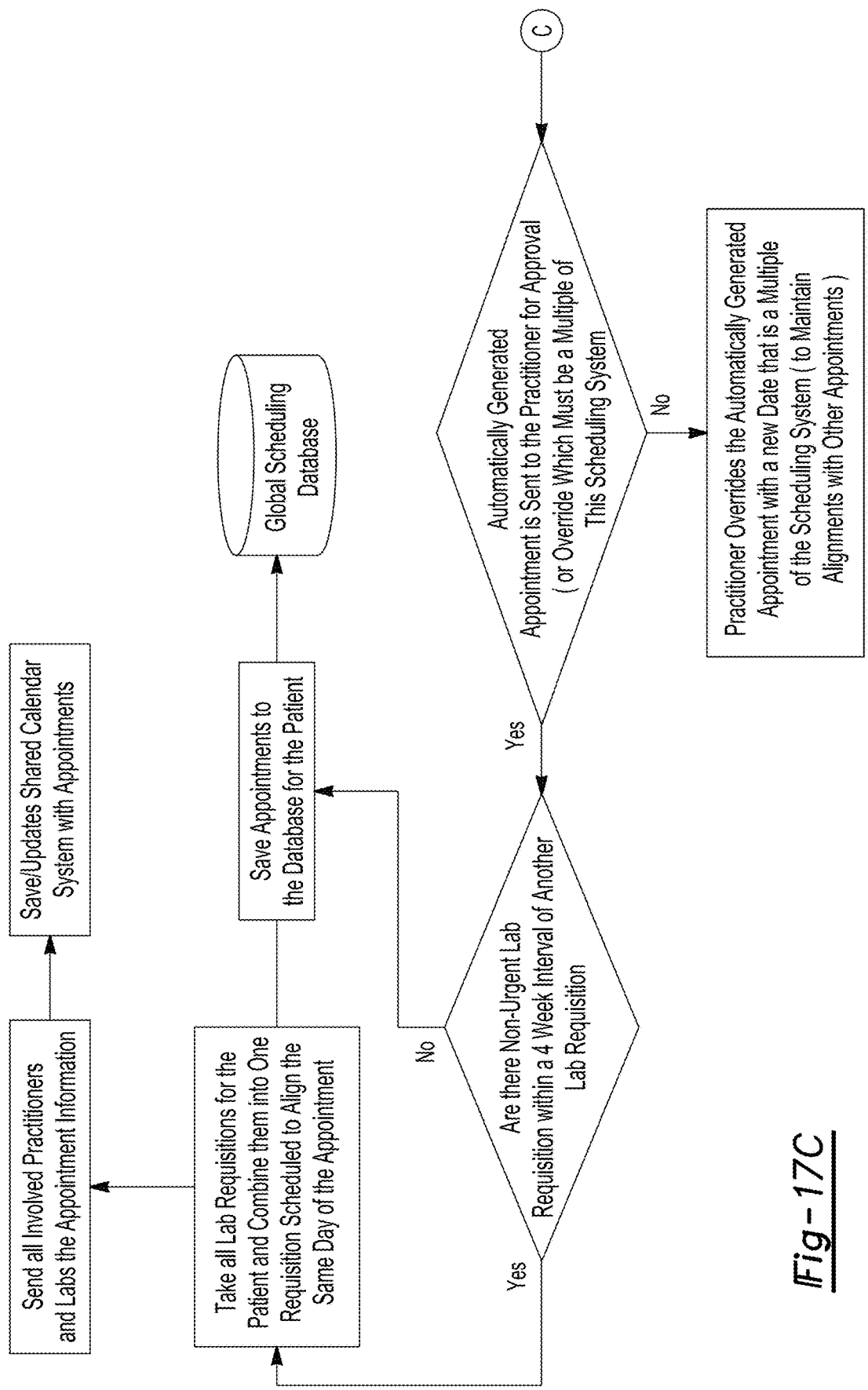
FIG. 17C depicts yet another continuation of a flow diagram for determining scheduling based on a SPA score according to one or more embodiments shown and described herein.

FIGS. 17-17C Depict a flow chart for scheduling based on the TOR and SPA scores determined in the aforementioned. FIG. 17 depicts scheduling after medical practitioners input specialty morbidity items via a checklist into the EMR system. If in SPA is score is greater than or equal to 5 for any system, a quick consult may then be scheduled. Looking now too FIG. 17A, if the TOR score is between 0 and 9, by way of example, the practitioner then involves the patient's MRP primary MD or allied health care professional as needed via quick consultation and said patient receives notification to review and assess as needed. Referring now to FIG. 17B, the appointment frequency for nurse practitioner and allied health practitioners is determined based on the TOR score. As illustrated, the higher the patients TOR score, the more frequently a regular appointment will be scheduled. As illustrated, the higher the patients TOR score, the more frequently a regular appointment will be scheduled.

Figure 18:
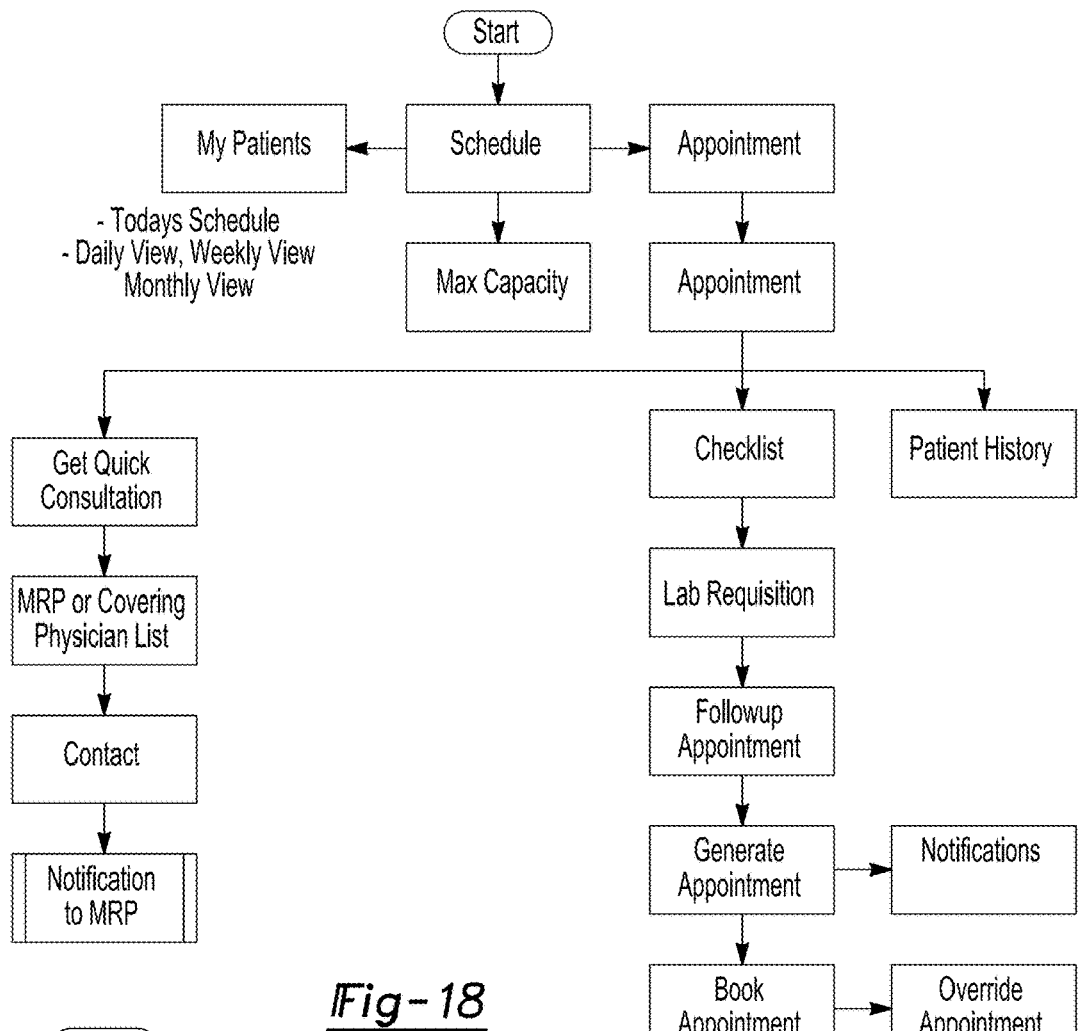
FIG. 18 depicts a flow diagram of the access and data collection seen by a physician using the program according to one or more embodiments shown and described herein.

Referring now to FIG. 18, the physician is a user type that has the ability to view patients, view all patients registered in the system, view patient details, history and medical notes. The physician also has the ability to view schedules by daily weekly or monthly arrangements, and view appointments and appointment details to confirm checklists schedule follow up appointments override follow up appointments and get quick consultations. The physician may also be notified if the patient has been served by the covering physician.

Figure 19:
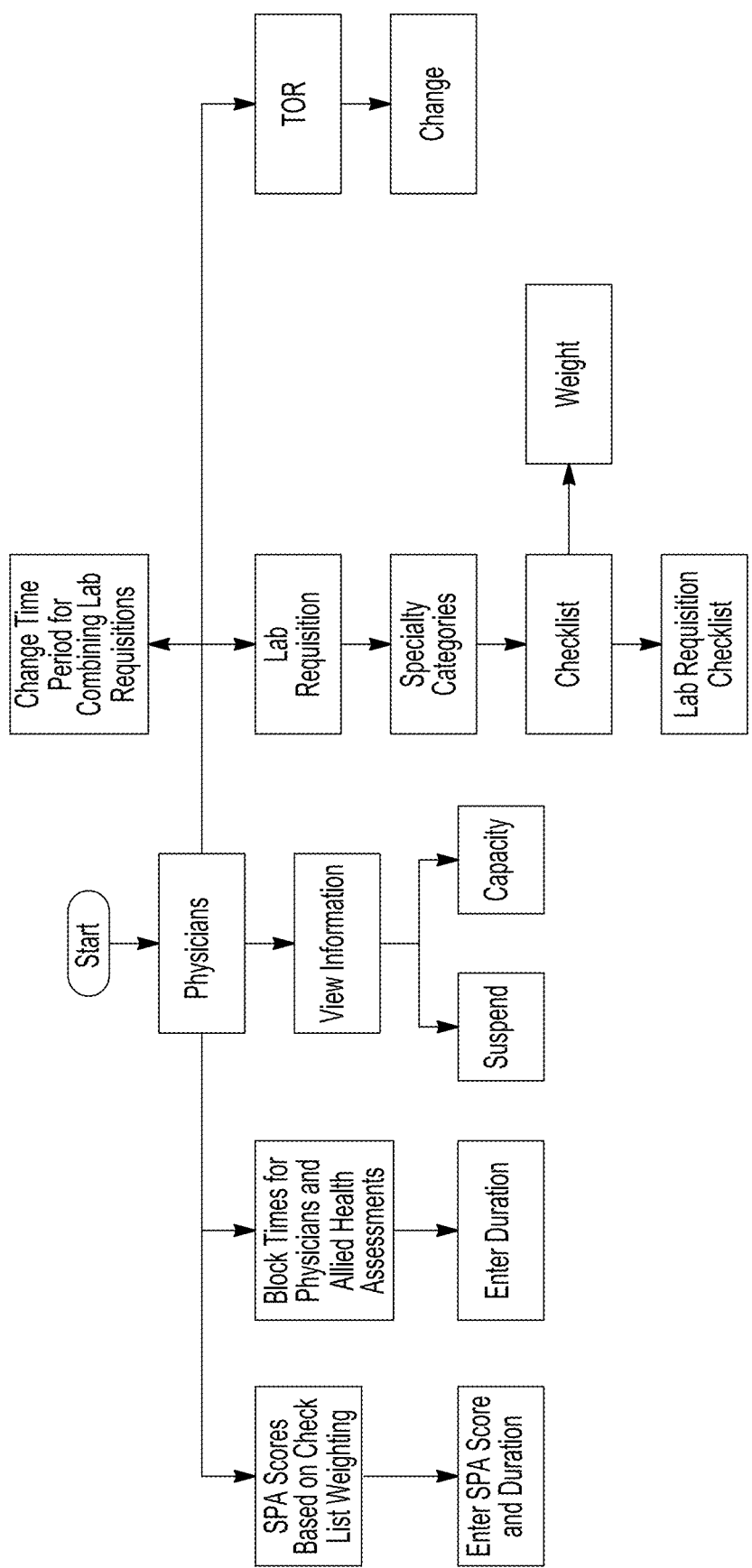
FIG. 19 depicts a flow diagram illustrating the administrative access and data input according to one or more embodiments shown and described herein.

FIG. 19 Depicts the administrative panel for input and checking information. The admin is a user type that has administrative features such as: view all physicians, view physician details, schedules, patients, view all patients including their information, view MRP appointment details, change SPA duration, Change TOR values configure checklists and add weights and configure lab requisition.

Figure 20:
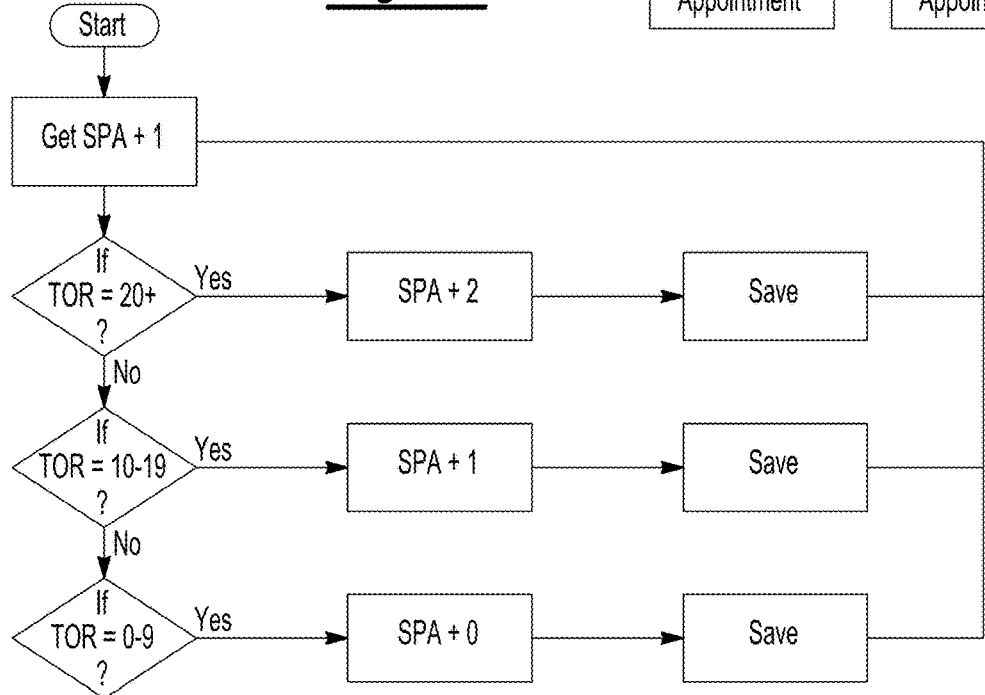
FIG. 20 depicts a flow diagram the process of fetching all SPA scores and applying a TOR score to get the actual SPA score according to one or more embodiments shown and described herein.

FIG. 20 depicts application of the TOR score. The Tor determines the overall risk of the patient. This is calculated by factoring in all individual risks from all specialties. the higher the TOR score, the quicker a patient may need to see a specialist.

FIG. 22 depicts appointment scheduling. The objective of this process is to determine the best week that the appointments can mesh together if multiple appointments are required, and to generate options for the patient/provider to choose from. The process checks by the highest priority SPA score as all other appointments are a multiple of the highest requirement. The system then automatically schedules an appointment of the highest priority appointment. The other appointments will all then fit into the highest priority appointment time slot. FIG. 22 depicts potential override by the physician. In the case the physician needs to override an appointment, they will have to select the appointment time from the standardized TOR and SPA booking options. This will allow the other appointment to be stacked with the appointment.

Figure 23:
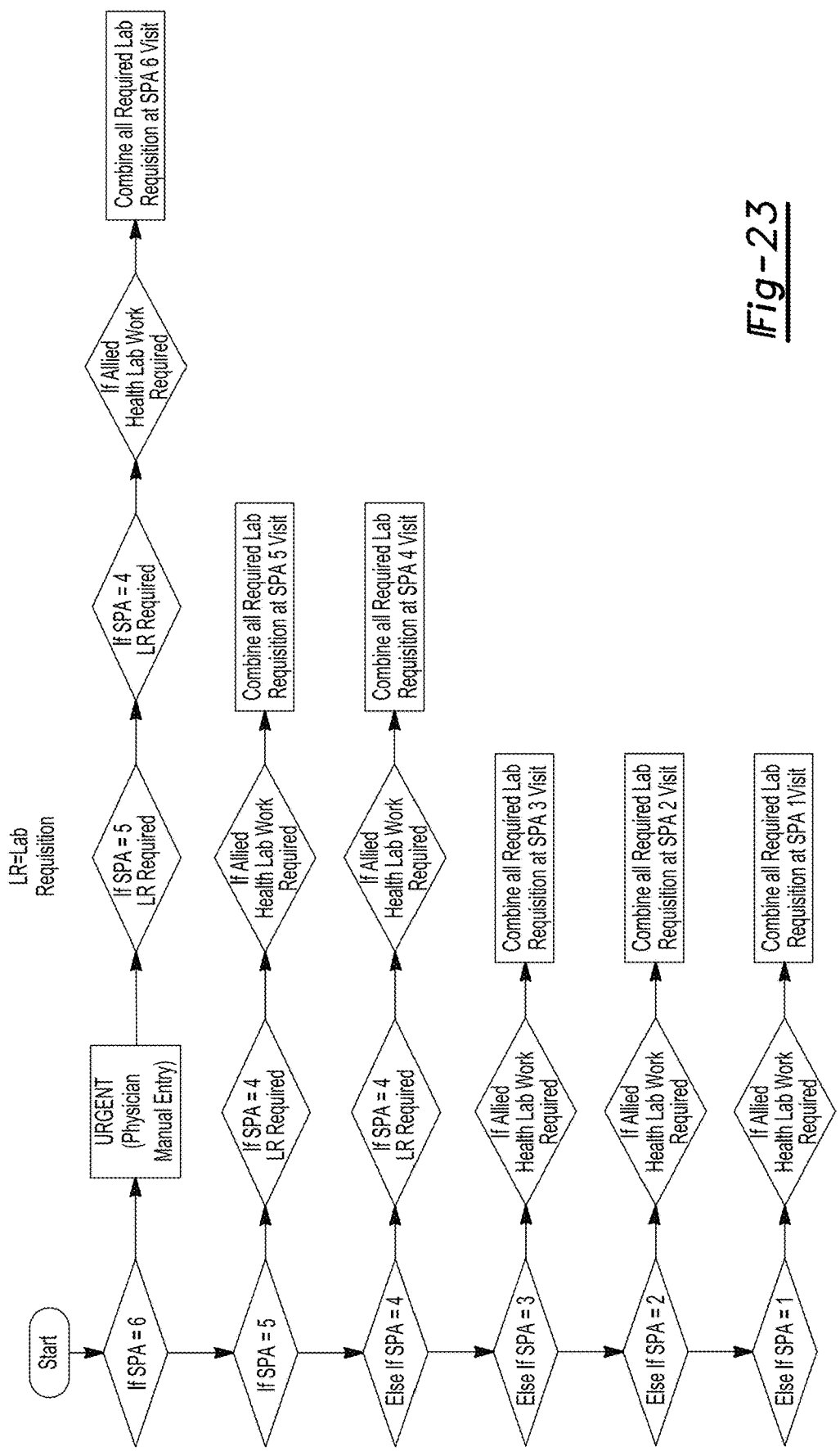
FIG. 23 depicts a flow diagram illustrating the lab requisition schedule creator according to one or more embodiments shown and described herein.

FIG. 23 depicts the lab requisition schedule. The objective is to schedule all lab requisition appointments together wherever to minimize blood drawing and duplication of tests. The objective is to get all non urgent lab requisitions within a defined period, such as within four weeks, of the most urgent appointment to be drawn at the same time. As illustrated by the series of steps, if the patient has in SPA score of five, all SPA 4 lab work is combined to the required lab requisition at SPA 5 visit.

Figure 24:
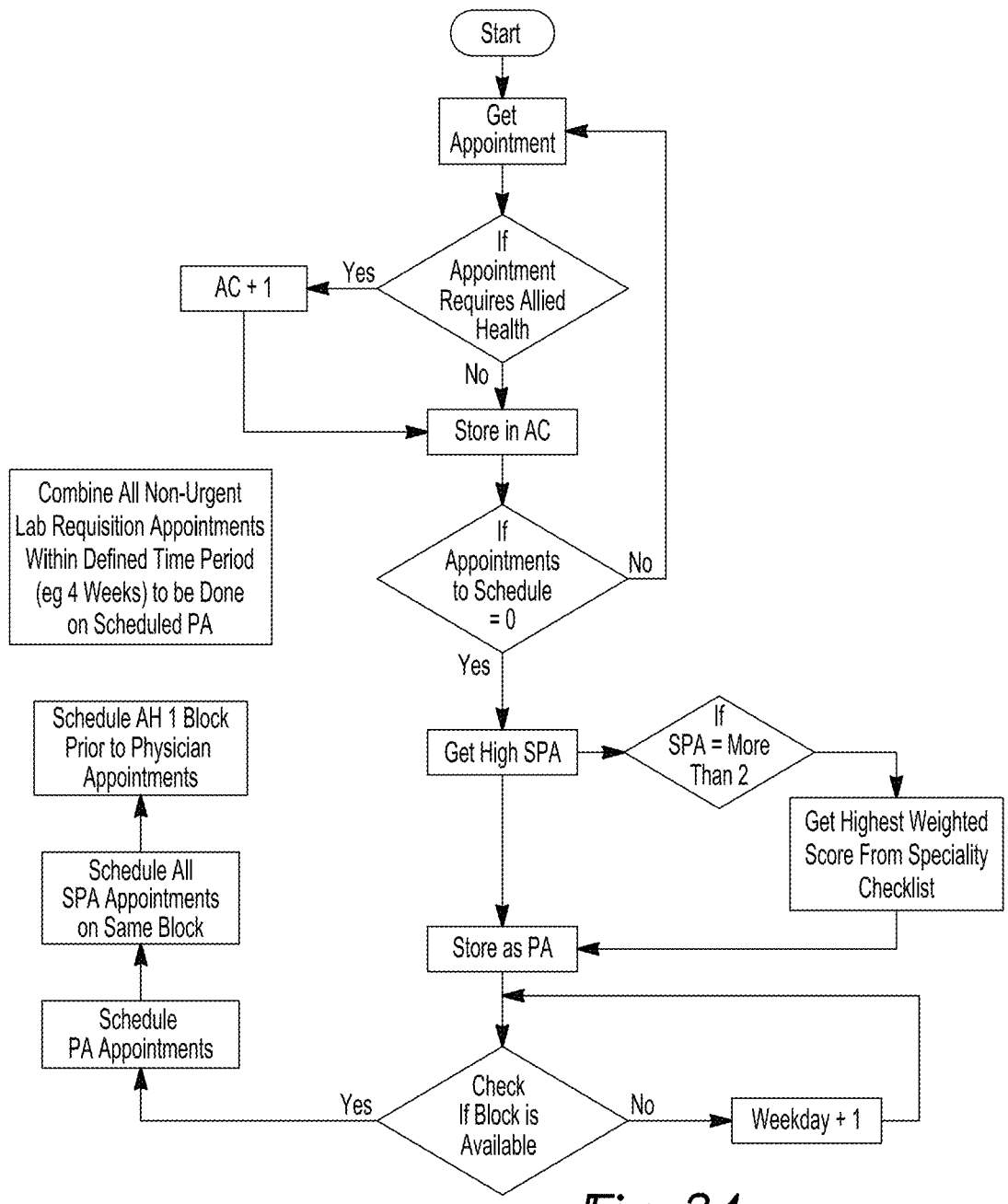
FIG. 24 depicts a flow diagram illustrating an appointment scheduler according to one or more embodiments shown and described herein.

FIG. 24 Depicts additional scheduling. Once the preferred week is determined, the system will mesh the appointments together according to the weekday and availability of physicians. The system will check for the total number of appointments to be scheduled for that day according to TOR based nurse practitioner led allied health assessments. The system then views the highest priority appointment by the SPA score and start viewing to see if an assessment block is available on the physicians calendar. If more than one SPA score is the highest, it will evaluate weights as applied to the SPA score and consider the highest weighted sum as the priority specialty to book with. Once the highest priority SPA appointment is booked, the others will be automatically scheduled within the same block slot. If this system determines that a TOR based Nurse Practitioner led Allied health care assessment is also required, It will automatically be booked in the time slot immediately preceding the SPA based physician appointment. The system then will perform the same steps for two other appointment blocks in the same week to show alternative appointment options to the patient.

Figure 25:
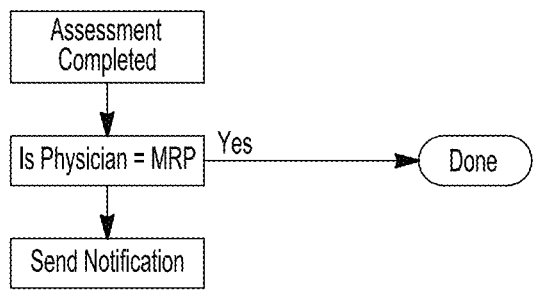
FIG. 25 depicts a flow diagram to determine the MRP in each specialty category according to one or more embodiments shown and described herein.
Figure 26:
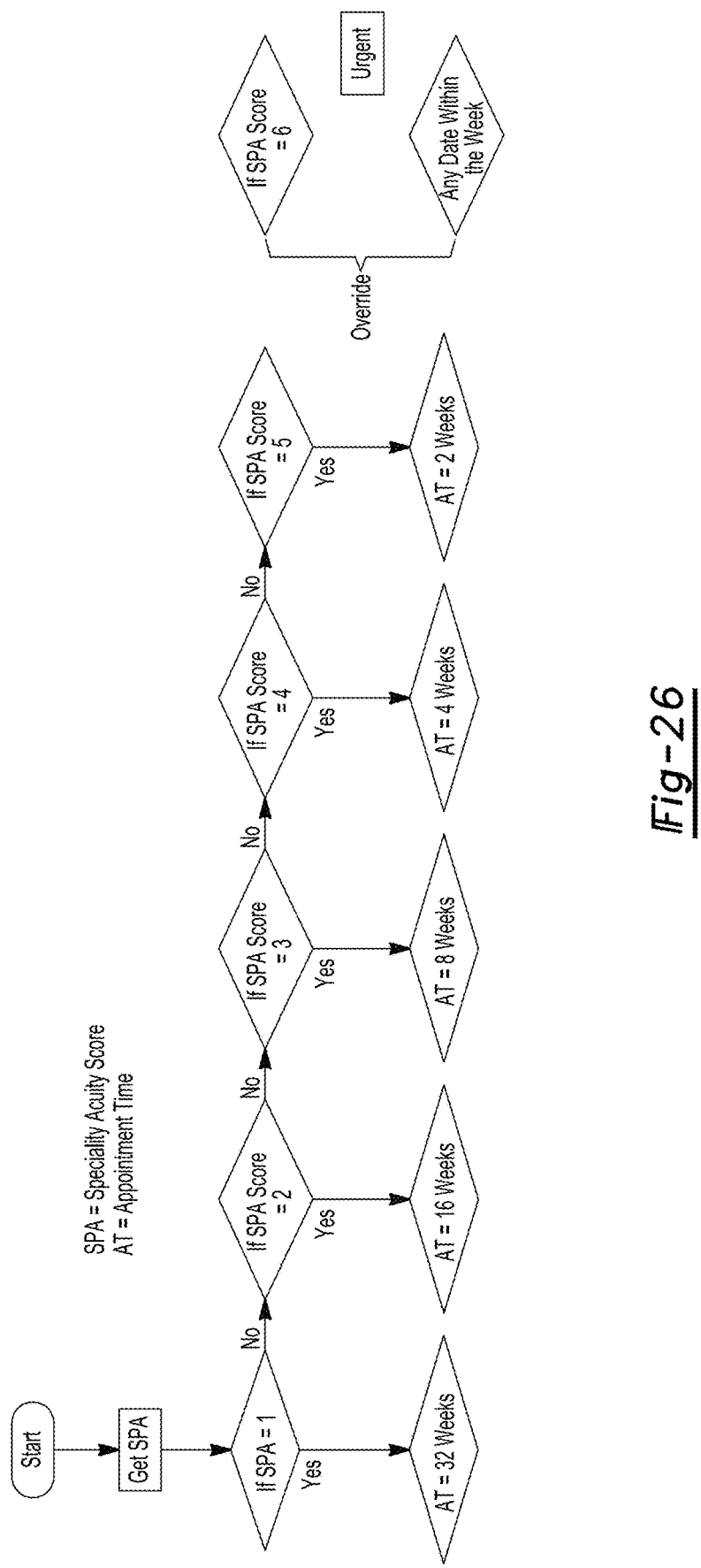
FIG. 26 depicts a flow diagram illustrating the process to determine the frequency of appointments according to one or more embodiments shown and described herein.
Figure 27:
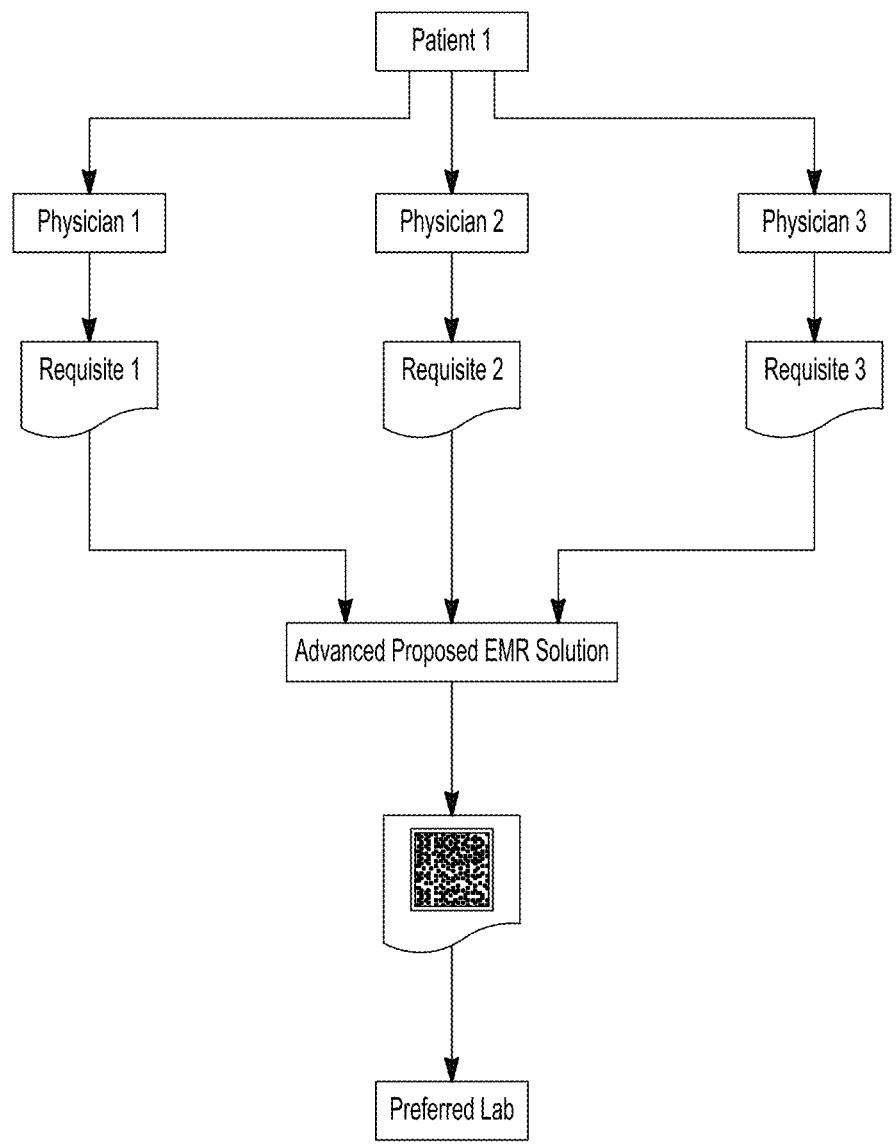
FIG. 27 depicts a flow diagram for generation of a QR code according to one or more embodiments shown and described herein.
Figure 28:
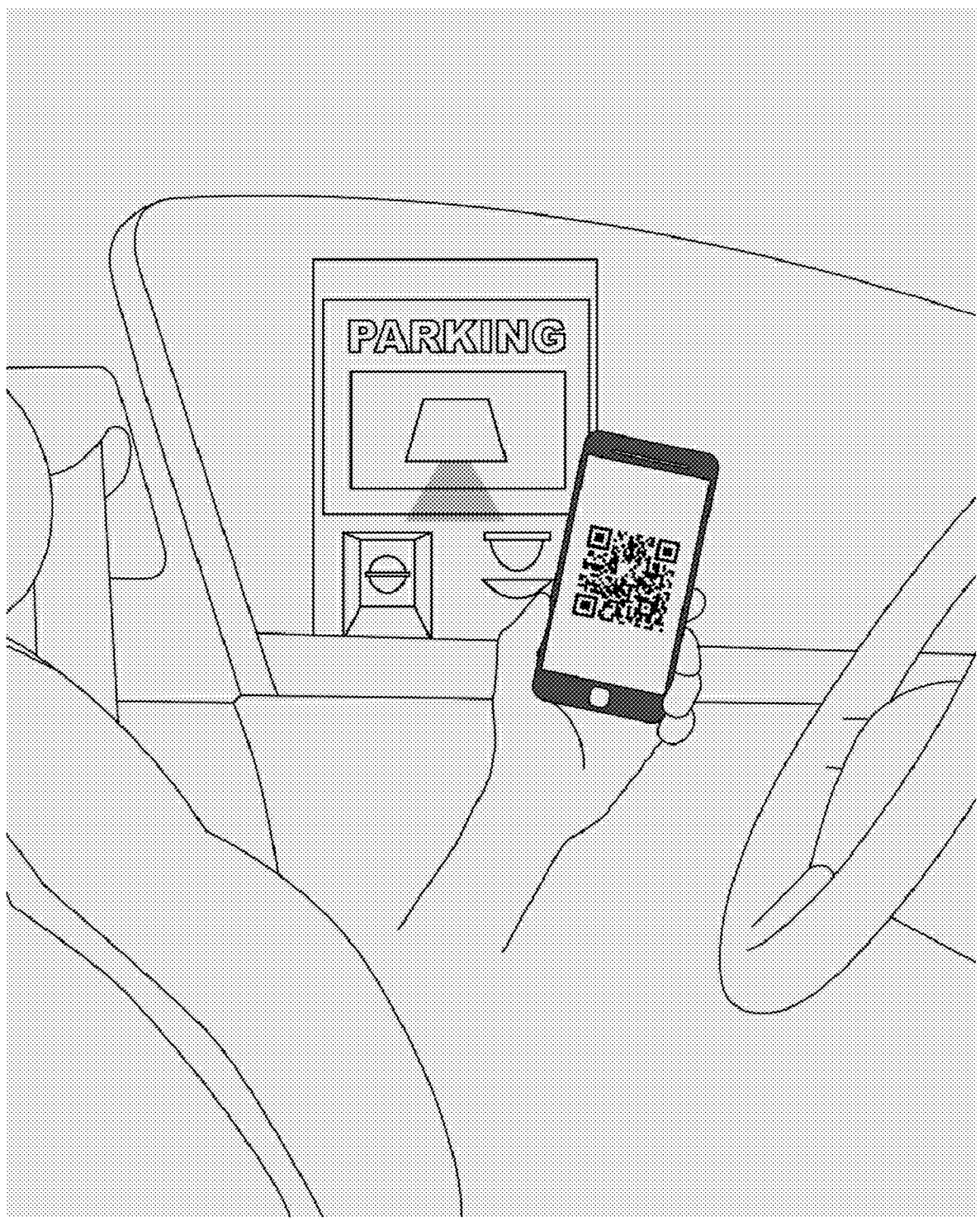
FIG. 28 depicts a perspective view embodiment of a patient using a QR code upon arrival to access parking on the requisite floor of the parking garage and the corresponding scanner to scan their corresponding QR code according to one or more embodiments shown and described herein.
Figure 29:
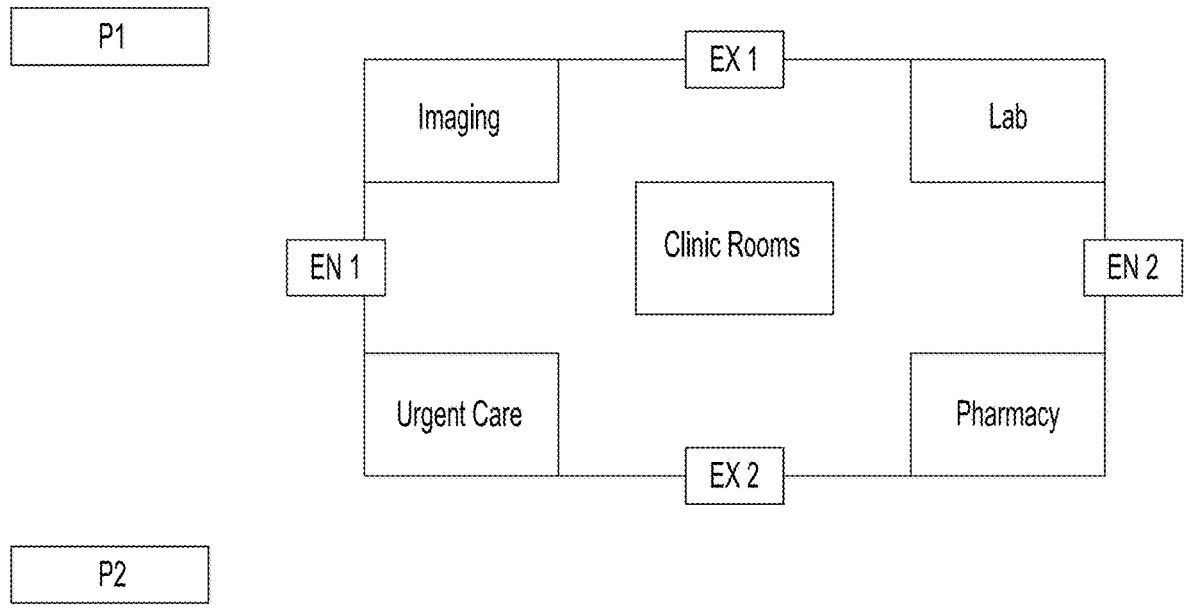
FIG. 29 depicts an exemplary layout according to one or more embodiments shown and described herein.
Figure 30:
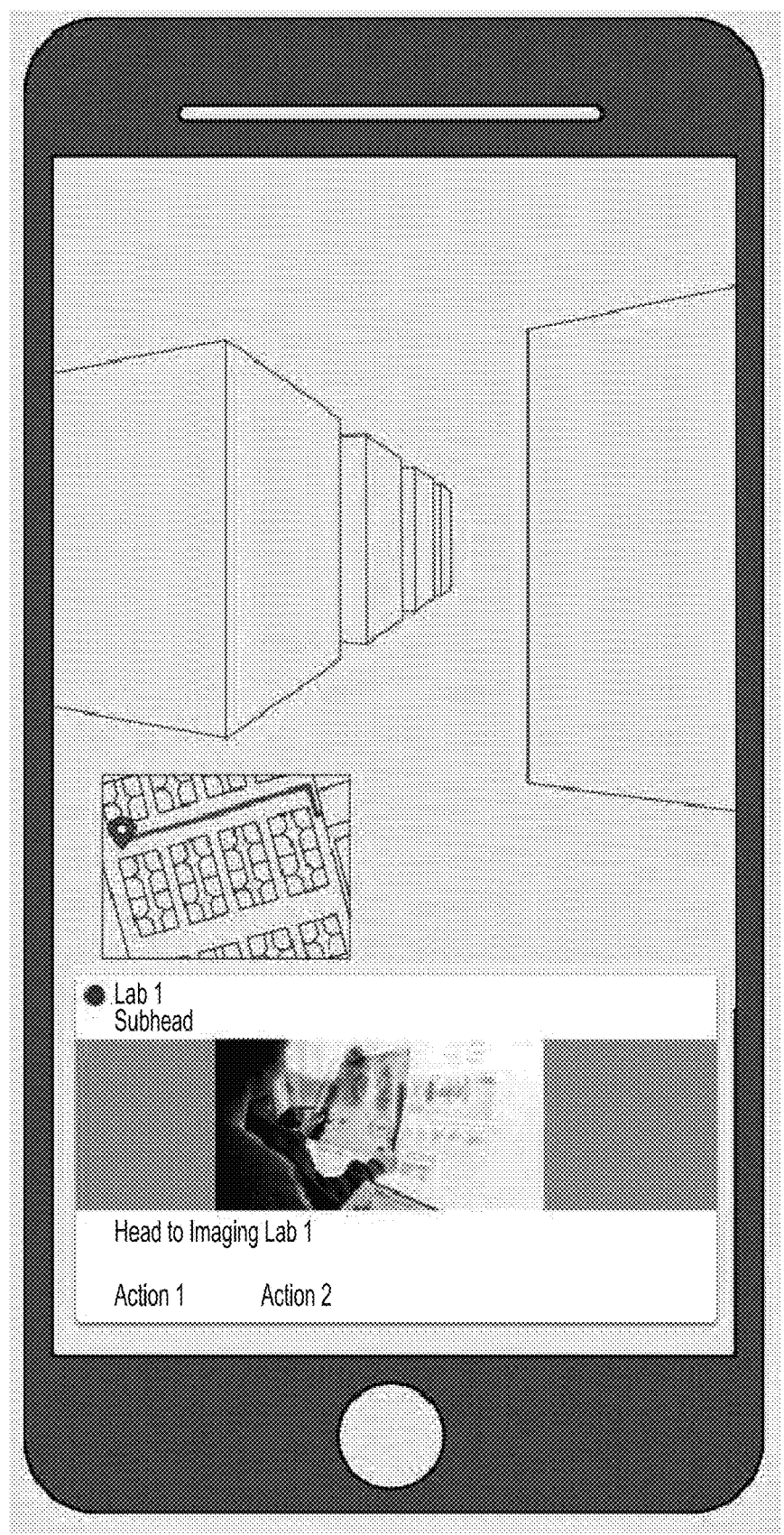
FIG. 30 depicts an exemplary screen shot showing an image of the facility to show a patient where to go according to one or more embodiments shown and described herein.
Figure 31:
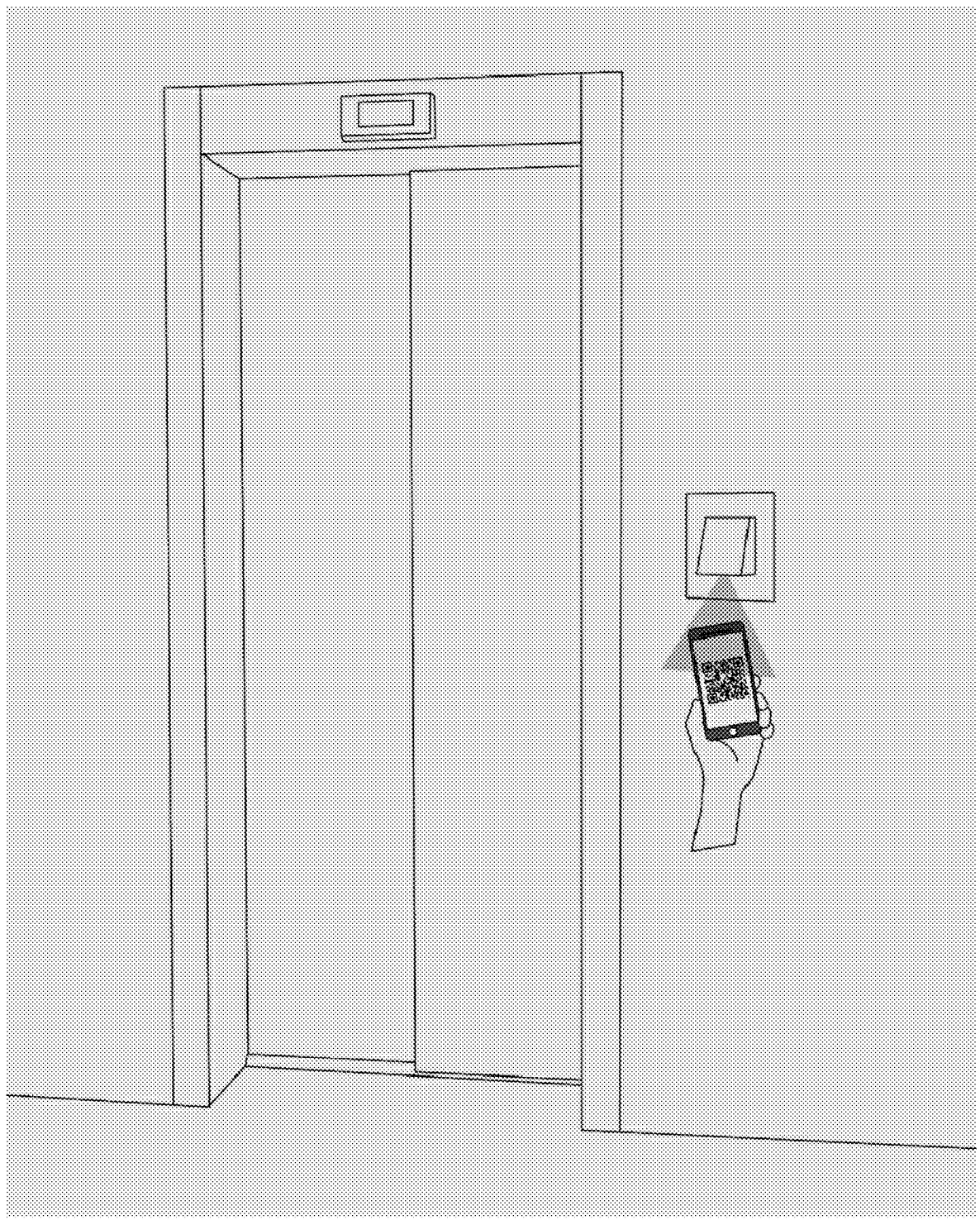
FIG. 31 depicts an exemplary perspective view of a user scanning a QR code to gain access to an elevator to take them to their appointment according to one or more embodiments shown and described herein.
Figure 32:
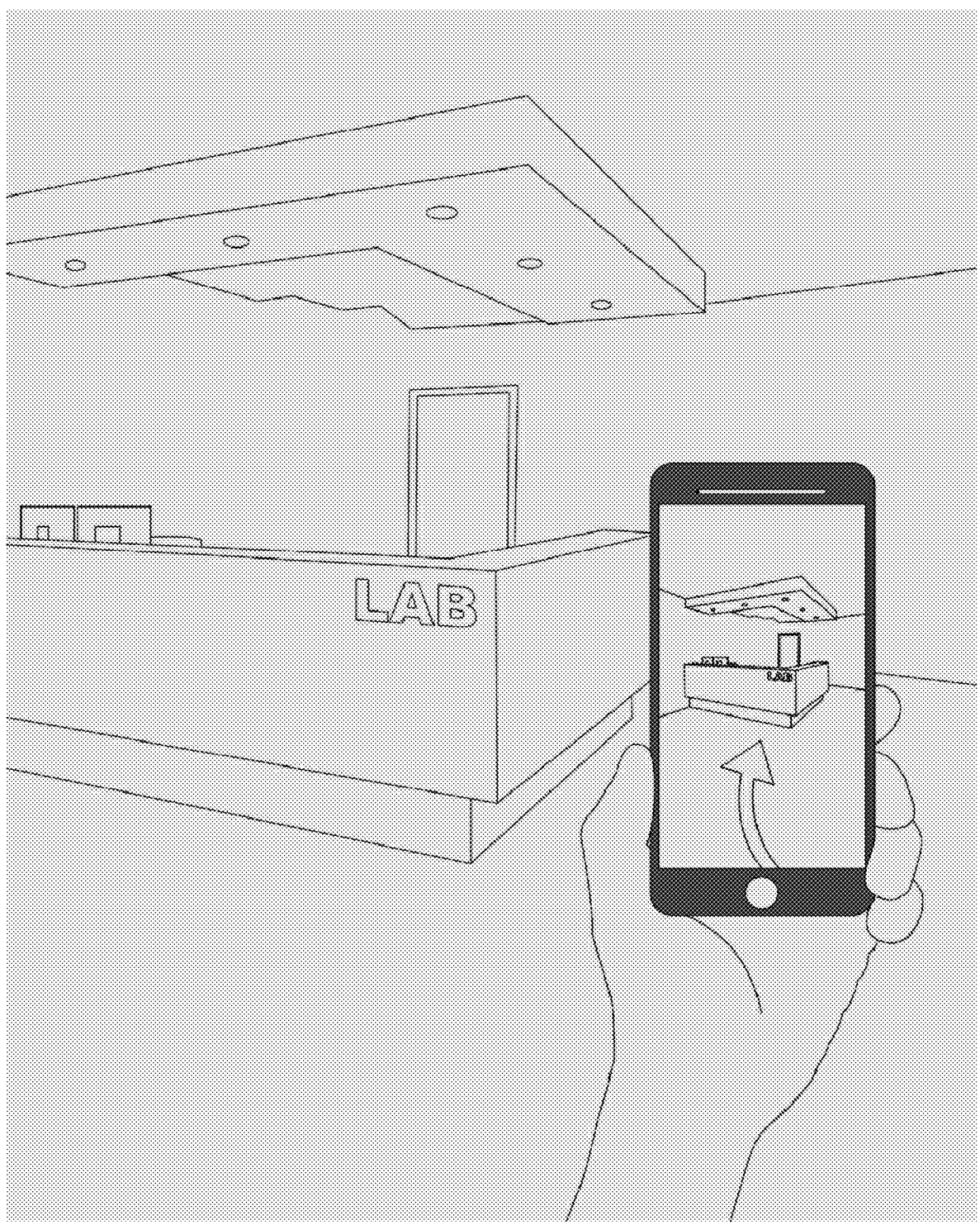
FIG. 32 depicts an exemplary screen shot showing instruction to the user using a mobile device on where to walk according to one or more embodiments shown and described herein.
Figure 33:
FIG. 33 depicts a screen shot of instructions provided to the user according to one or more embodiments shown and described herein.
Figure 34:
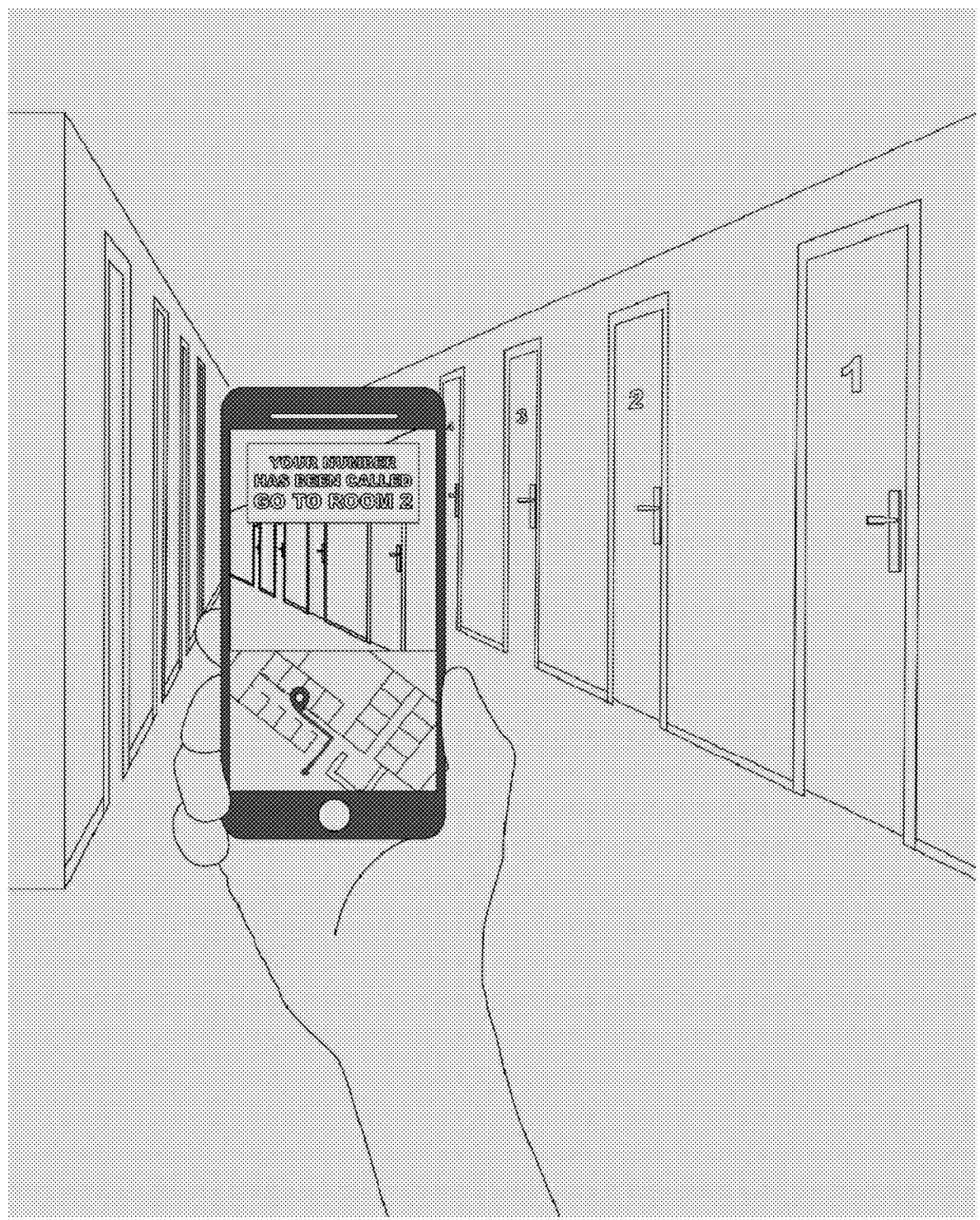
FIG. 34 depicts a screen shot of instructions provided to the user according to one or more embodiments shown and described herein.
Figure 35:
FIG. 35 depicts a perspective view of a user using the QR code to access the patient room according to one or more embodiments shown and described herein.
Figure 36:
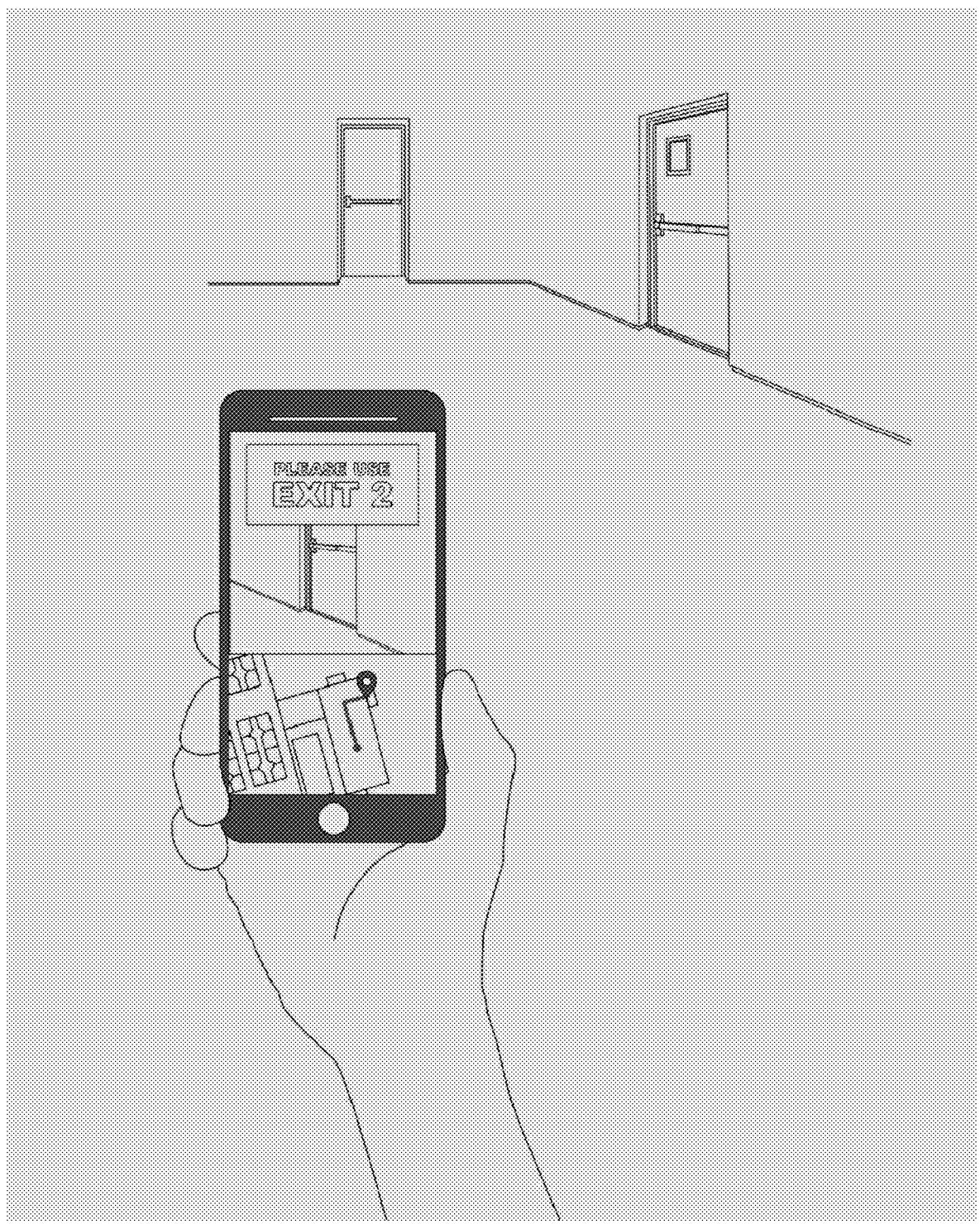
FIG. 36 depicts a screen shot of instructions provided to the user according to one or more embodiments shown and described herein.
Figure 37:
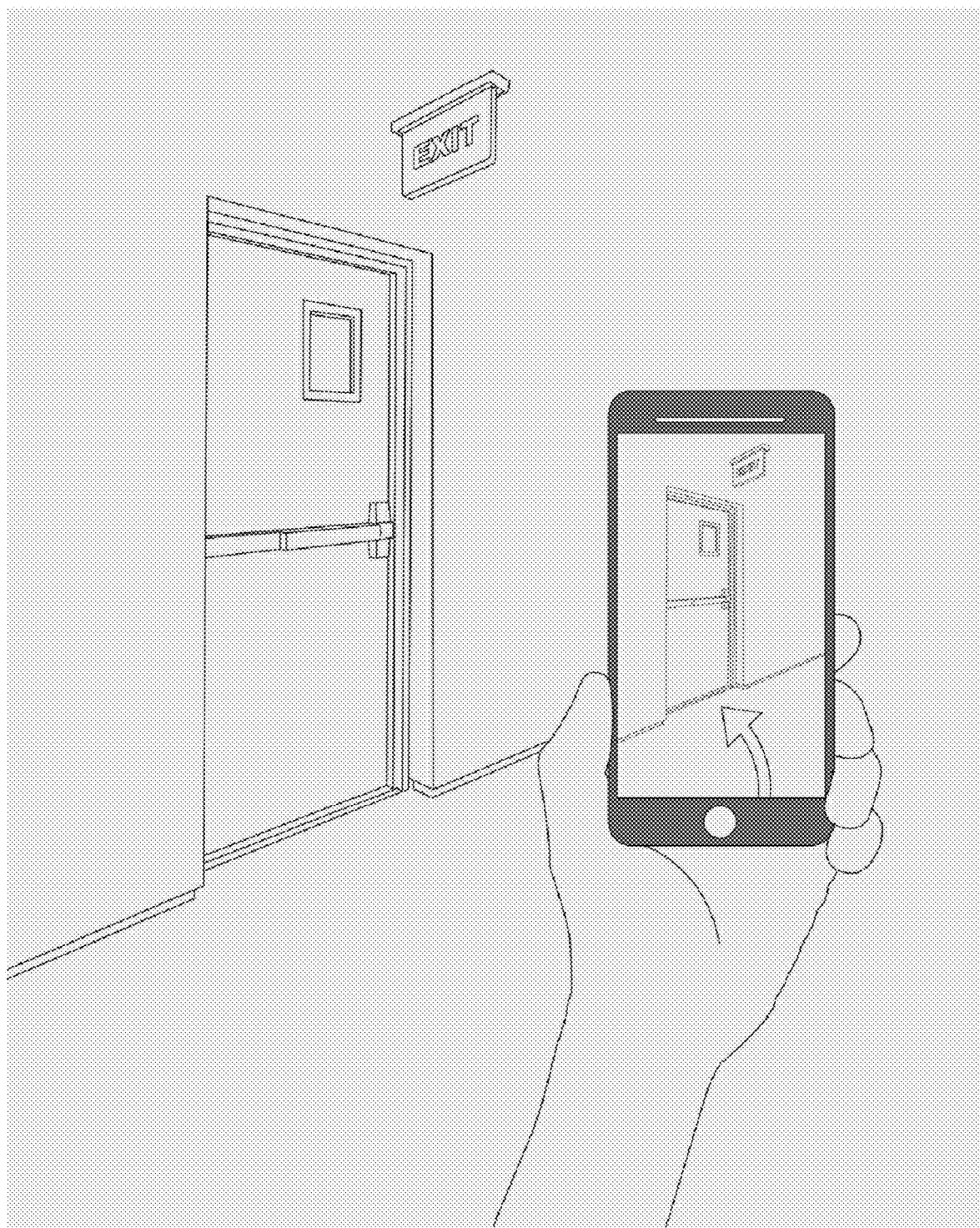
FIG. 37 depicts a screen shot of instructions provided to the user according to one or more embodiments shown and described herein.

FIG. 25 depicts the determination of the MRP in each specialty category. After every assessment a script will run to determine if the physician is the MRP. If the physician is not the MRP, the MRP will receive an automated notification that their patient has been addressed. Each patient at the facility has a MRP nurse practitioner and allied health as well as physicians and each of these categories have covering practitioners for the same time they are away. However, all assessments done by back up must be approved by the MRP. Further, each patient has a consistent MRP nurse practitioner and allied health practitioners that coordinate with the primary care physician at all times to avoid siloed multiple allied health care assessments from individual specialties. There is consistent nurse practitioners allied health care team across covering the primary care practices. This system provides for a true integrated collaborative community based care that is not siloed with regards to nurse practitioners and allied health care nor physician multi care specialty care and allows for in person or virtual assessments.

Current practice employees allied health care disciplines within individual practices and are not shared by multiple practitioners at a single site. Therefore, patients may see multiple dietitians, pharmacist or allied healthcare professionals depending on which specialist or primary care practitioners they are visiting. In addition, current models are not standardized or efficient to match patient care needs in a priority fashion.

The system and method of some embodiments can be used as well for priority booking with allied healthcare professionals in a multidisciplinary setting with the same MRP (most responsible practitioner) model, TOR scores and procedures as outlined above to prioritize assessments and provide consistent and efficient care and optimal utilization of shared resources, while still being coordinated with medical appointments as well.

With regards to TOR scoring for allied healthcare, the higher the TOR score, the greater the need to allied healthcare support, led by a nurse practitioner, who tailors other allied healthcare involvement to the needs of the patient and can quick consult other allied healthcare practitioners, and reviews these assessments with the primary care doctor for that patient. Through this process, the primary care SPA score can be adjusted or quick consultation with any other specialty can be obtained also.

One of the main clinical advantages of this program (EMR) is that it forces the practitioner at each clinical interaction to focus on the acuity and priority needs of each individual patient while at the same time ensuring that their chronic ongoing comprehensive care is also looked after in a standardized fashion. We believe that comparative research done in this regard compared to standard care will show an improvement an emergency room utilization and hospital admission rates.

This program features described are intended to be used as the framework for a multispecialty and multidisciplinary integrated clinic EMR system that can be used separately or tailored to be compatible and complimentary to existing EMR systems. An independent EMR system can be developed with the above-mentioned program, or components of this program can be used to compliment and integrate with existing EMR systems already in use.

The system described herein is intended to be a one-stop-shop for all programs used by medical facilities also incorporating the physical layout of a medical building. Just as the clinic design is a one stop shop for multiple disciplines and specialties, the electronic operating system of the clinic should also be a one stop shop. Traditional clinics have an electronic medical record that is limited in function to predominately house patient and scheduling information. This system will not only be an electronic medical record, but will be an operational support system for the entire function of the clinic to be accessed through a single program.

An EMR application will be provided on a mobile device. The EMR application will be a 1) Quick Consult (quick consult) tool; 2) locating and paging system; 3) Ride request tool; and 4) Scheduling reminder tool.

The present system houses patient information and features a completely unique integrated scheduling program across multiple disciplines and specialties but will also incorporate a complete operational support system as well. As an operational support system, this system will act as a locating system for contacting or finding the location of any professional staff member or patient within the clinic. This will replace the need for separate paging systems.

Figure 15:
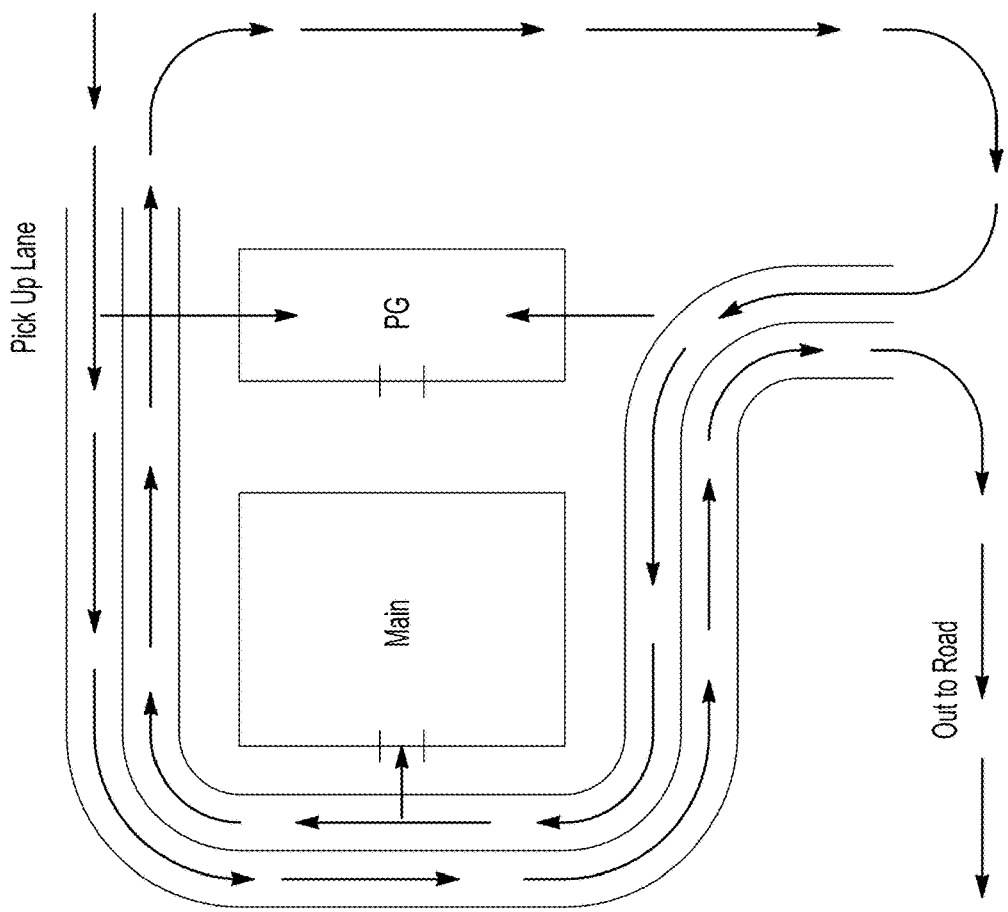
FIG. 15 depicts an exemplary building and parking garage layout according to one or more embodiments shown and described herein.
Figure 14:
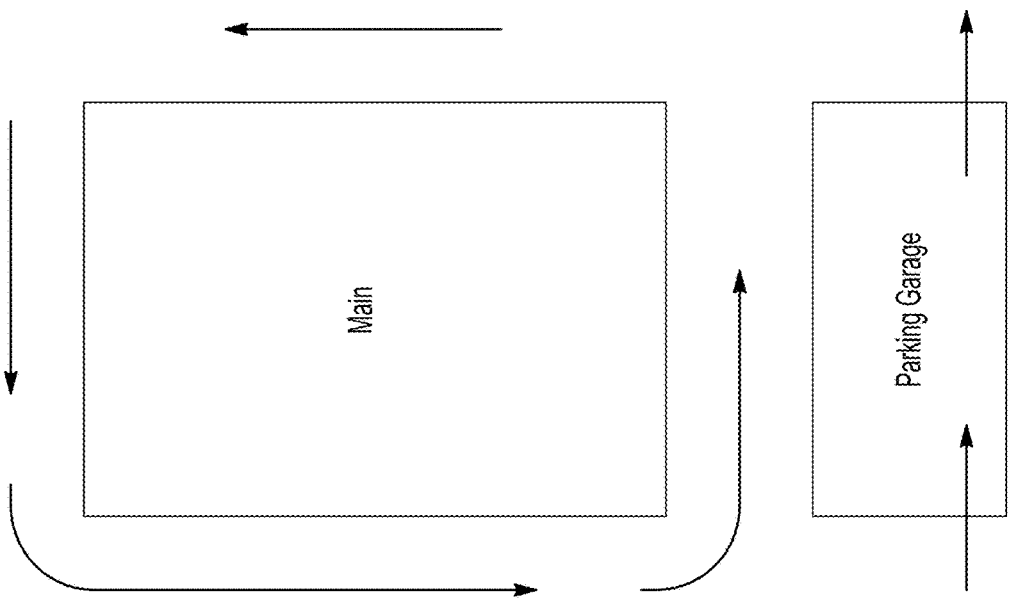
FIG. 14 depicts an exemplary building and parking garage layout according to one or more embodiments shown and described herein.

This system will have a built-in capability to connect autonomous electric vehicles to allow pick up and drop off for patients from their homes as well as for staff members to be brought to the clinic and to their home. There will be a confirmation mechanism to notify clients just prior to pick up connected through their smartphones. The system will connect to autonomous electric vehicles to allow pick-up from home and drop off at the most appropriate entrance and subsequent pick up and exit. This is utilized for both staff and patients. A path may follow a circular path around the building. Various advantages include: 1) a "green" and environmentally friendly solution; 2) eliminates parking needs; 3) eliminates transportation issues; 4) immediate pick-up and drop-off; and 5) provides for wheelchair accessible cars. The parking garage may be used to access the various floors, such as shown in FIGS. 14-15.

The physical layout of the building and the surrounding internal road as well as the set-up of the parking garage allows for pick up and drop off at designated entrances and exits. All entrances are from the north and south and all exits are from the east and west to allow a coordinated system for pick up and drop off at the building.

The ground floor map of the physical plant layout surrounding the building illustrates the flow pattern of vehicles around the building. The multilevel parking garage with entrances at the south end will allow for easy drop off for autonomous vehicles.

The use of autonomous vehicles coordinated with the clinics multi-functional electronic medical record and operational support system will allow for transportation to and from the nearest emergency room for patients who need to attend the hospital but do not require an ambulance with Appropriate protocols in place The system as described herein may also track outcome data. The system will calculate target indicators for quality based outcomes and assigns a score to each MRP involved in care for incentive bonuses for quality care. This data is tracked and assigned in the program itself.

Overall, the system includes:
Payroll
Billing and Expense Calculation
Transportation (to/from)
EMR
Scheduling
Location & Paging
Quick Consultation
Target Outcome Data for Quality Care Incentives
Satisfaction surveys
Radiology booking
Pharmacy (order entry/counseling)
Lab (direct information)
UC (visits, scheduling)

The system as described herein is particularly advantageous in that it is a green solution in the face of an increasing climate crisis, eliminates parking and the physical design of the building allows for parking garage space to be converted to clinical space, eliminates transportation issues that plague patients both socially and financially, immediate pick up and drop off increase compliance with patient visits which would improve outcomes, wheelchair assessable autonomous vehicles will be available with assistance where needed Safety given extended hours of operation.

Within this electronic medical record will be the ability of each individual discipline or specialty to input appropriate quality target indicators and have these measured for each individual most responsible physician or discipline involved in the care of patients to calculate quality of care indices to be tracked and used in a way to continually assess for quality improvement.

The design as shown herein improves patient flow to prevent the spread of infectious disease. The parking garage, as illustrated in FIGS. 14 and 15, aligns with multiple flows housing multiple services to reduce the need of elevator use. Further, North and South elevator locations allows designation of the south side for entrance for all floors above the first floor and the north side elevator to be used to exit to main floor avoiding waiting rooms with immediate east-west exit after reaching first floor. Direct access to each floor from the parking garage allows isolation of vulnerable populations and staff to single floors.

Figure 53:
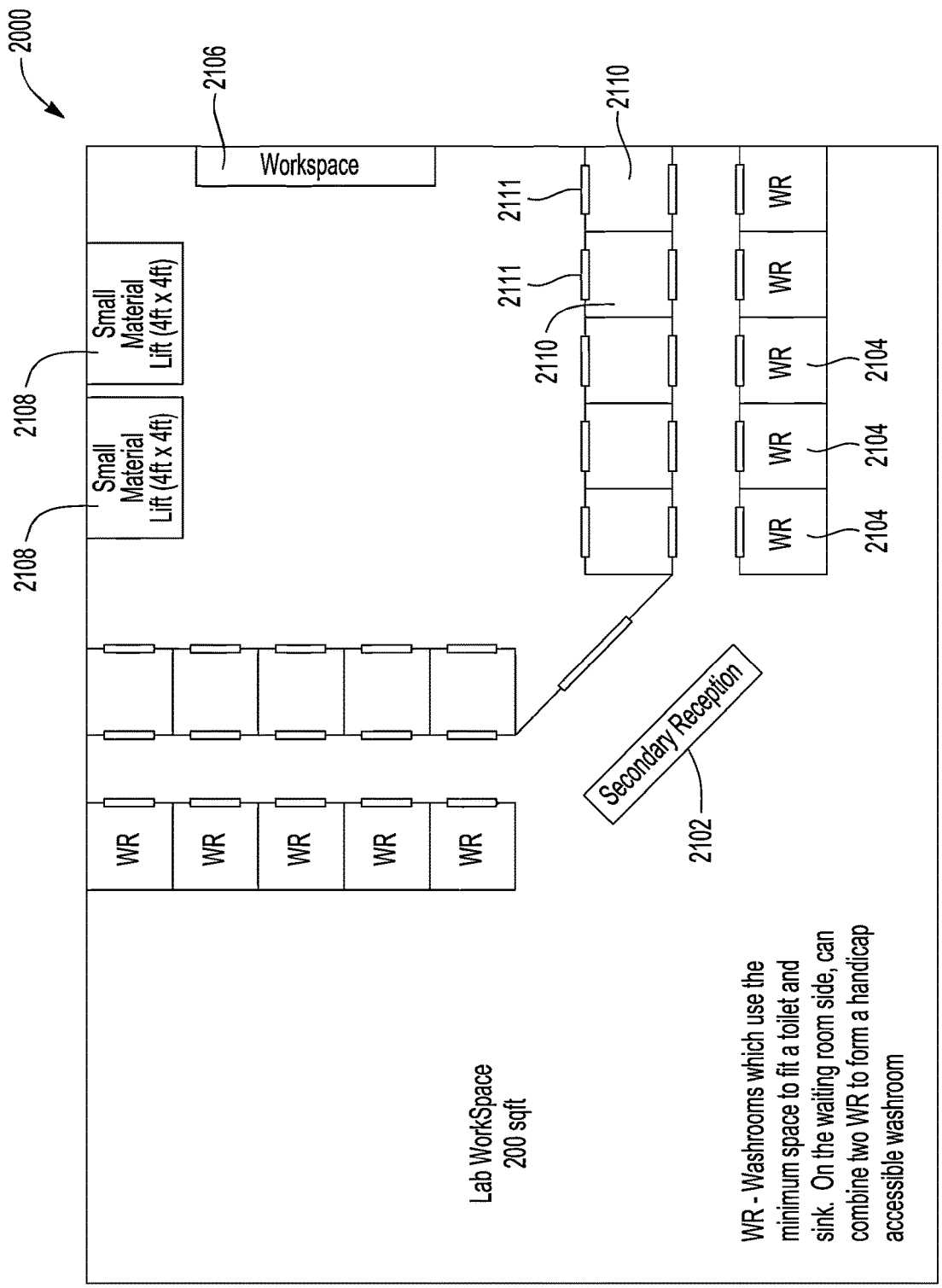
FIG. 53 depicts a layout of a lab according to one or more embodiments shown and described herein.
Figure 54:
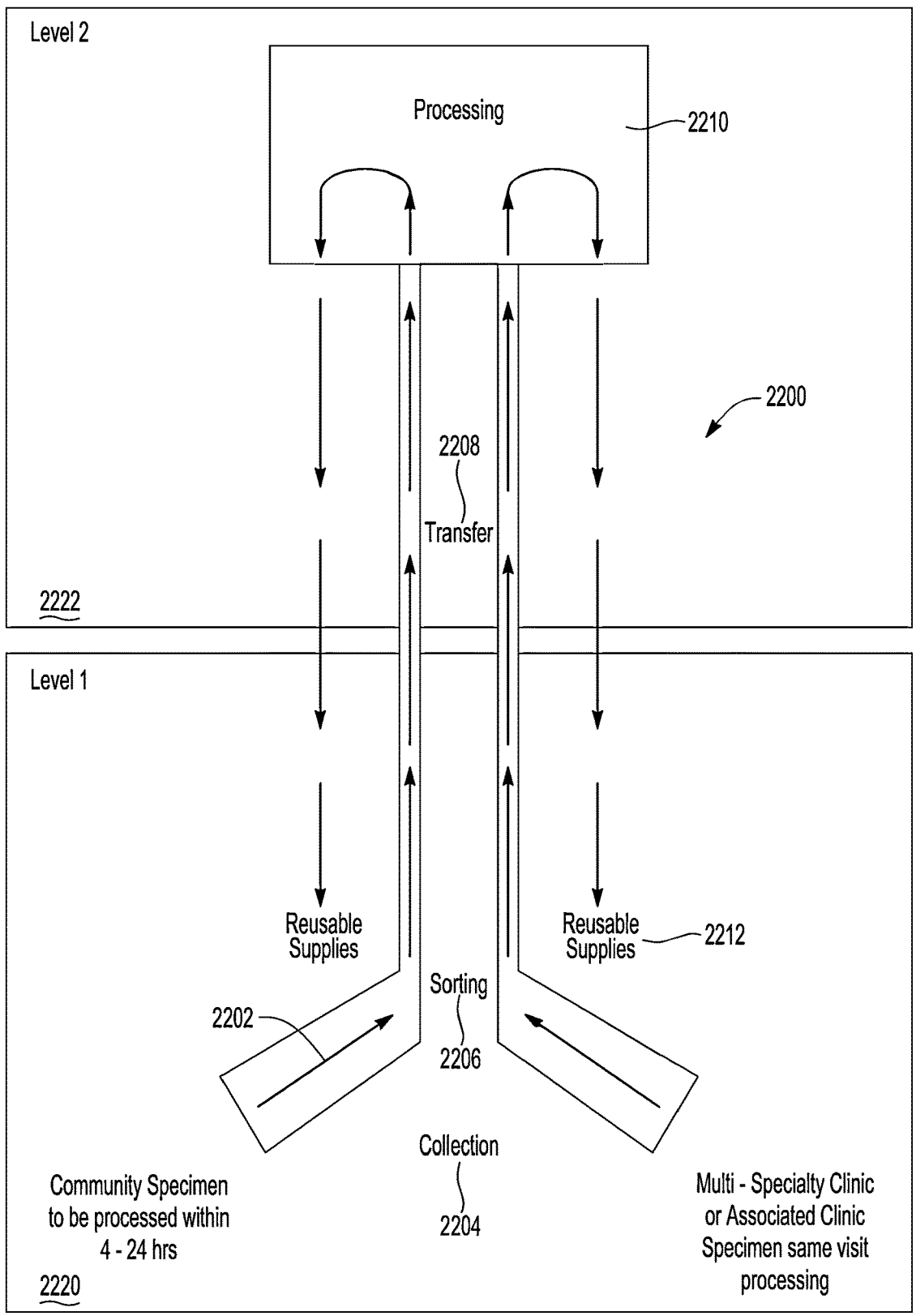
FIG. 54 depicts a multi-level physical layout of a building wherein level 1 includes collection and sorting and level 2 includes transfer and processing according to one or more embodiments shown and described herein.
Figure 55:
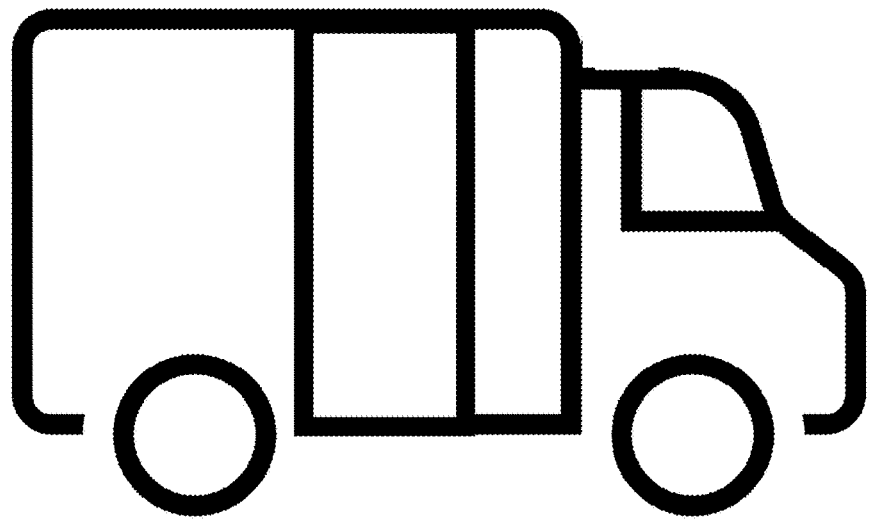
FIG. 55 depicts a side view of the autonomous vehicle having a large door opening enabling a user to walk through according to one or more embodiments shown and described herein.
Figure 56:
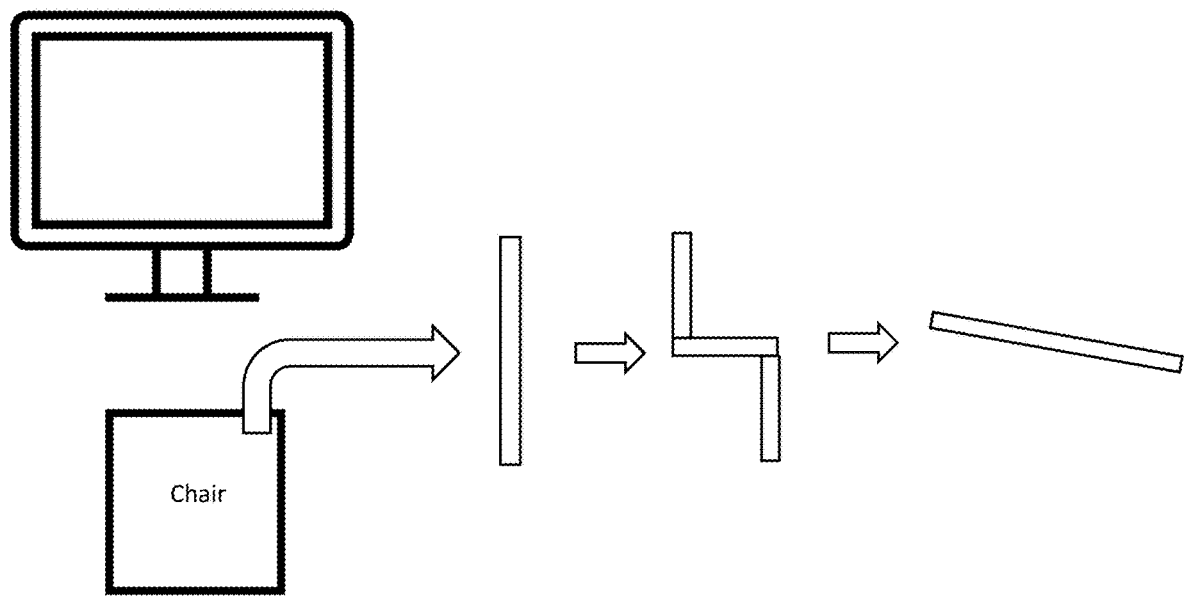
FIG. 56 depicts a screen enabling communication with a patient and chair movable from a standing to sitting to generally vertical portion according to one or more embodiments shown and described herein
Figure 57:
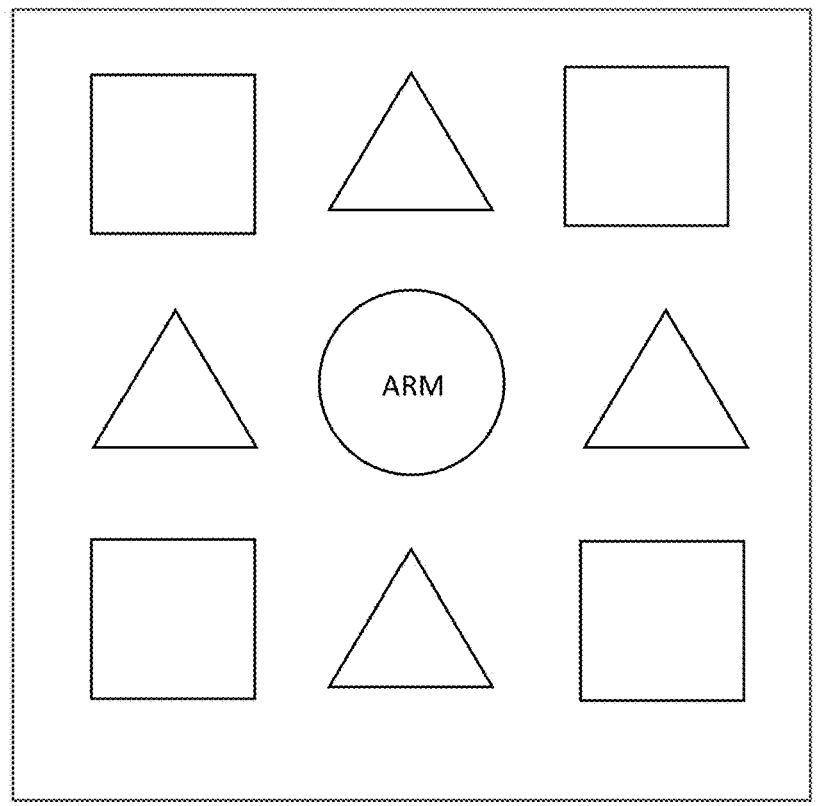
FIG. 57 depicts an exemplary view of side interior panels/back interior panels with a robotically controlled arm, robotically controlled instruments that extend to desired position through the aid of cameras and sensors (rectangles), and supplies that can be accesses by the robotic arm (triangles) according to one or more embodiments shown and described herein.
Figure 58:
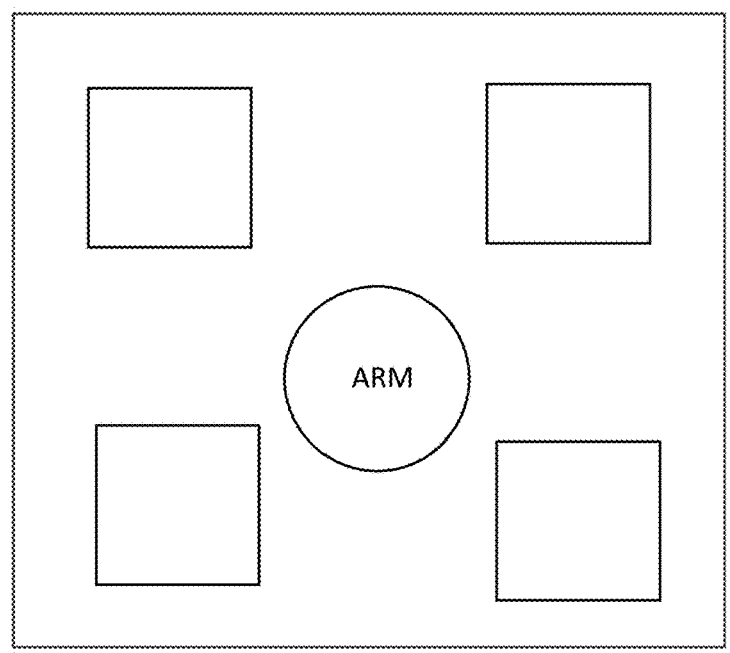
FIG. 58 depicts an exemplary view of side interior panels/back interior panels with a robotically controlled arm and robotically controlled instruments that extend to desired position through the aid of cameras and sensors (rectangles) according to one or more embodiments shown and described herein.
Figure 59:
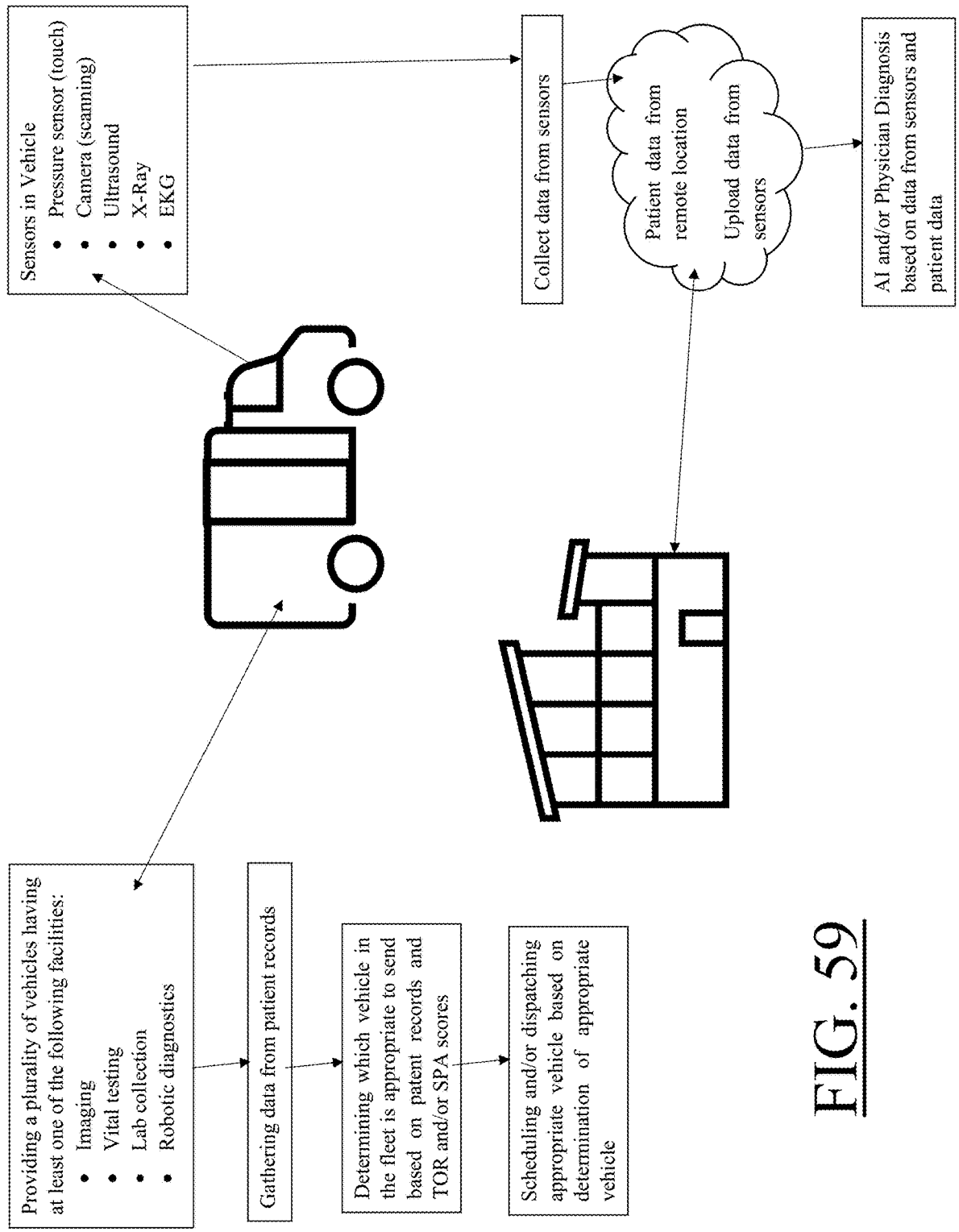
FIG. 59 depicts a flow chart of the system and vehicle apparatus according to one or more embodiments shown and described herein.
Figure 60:
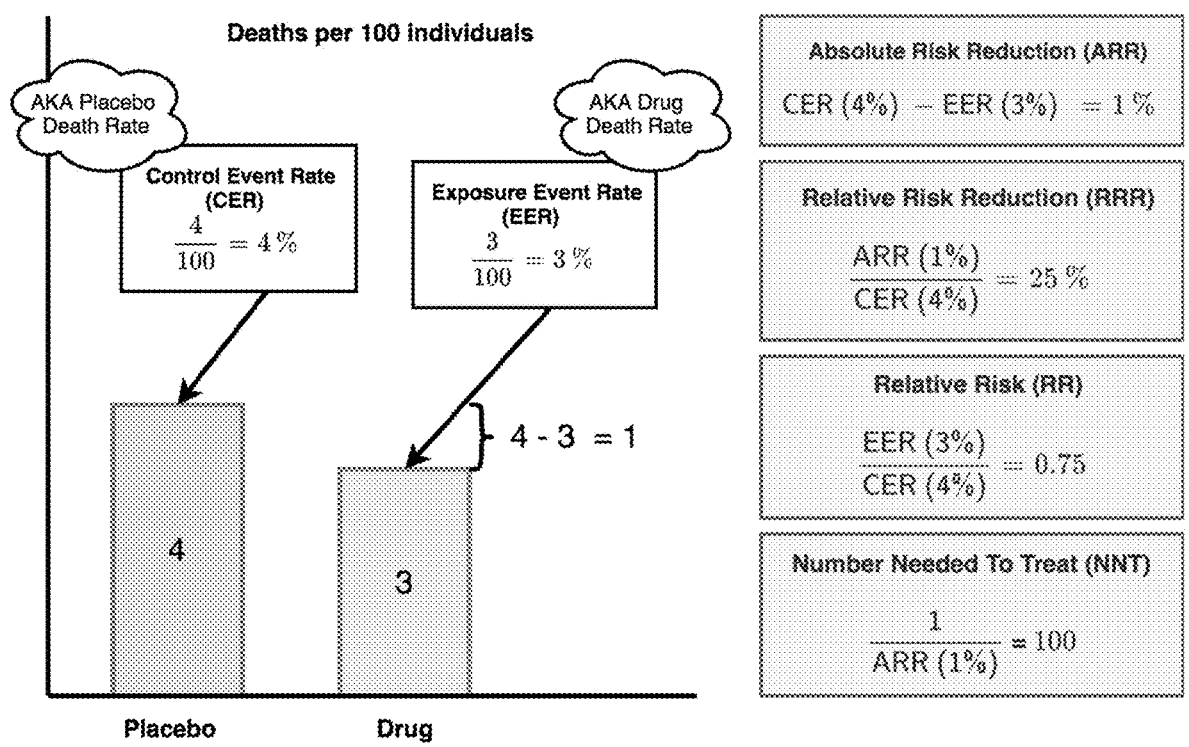
FIG. 60 depicts a graphical depiction of the measures of treatment effect according to one or more embodiments shown and described herein.

Now referring to both FIGS. 52 and 53, the present system solution initially includes a physical arrangement 2000 of the bloodletting stations and sorting of specimens including a first level 2220 and a second level 2222. This is on the first floor of the clinic immediately below the larger full laboratory (level 2) where specimens are processed. On level 1 (2220), such as shown in FIG. 52, each phlebotomist has their own room 2110 for bloodletting and immediate transfer of specimen to the sorting area. A plurality of washrooms 2104 are used for urine collection specimens are immediately across from the bloodletting rooms 2110 used for that particular patient. The phlebotomist on collecting the desired specimens transfers them to the sorting area directly without having to leave their room through the window 2111 identified in FIG. 52. As further illustrated in FIG. 52, the layout includes a secondary receptionist 2102 to greets patients and to direct patients to the proper areas. The work space in the layout 2000 further includes a workspace 2106 and at least one lift or other elevators 2108 configured to move material to Level 2.

FIG. 53 illustrates a unidirectional flow 2202 (as evidenced by the arrow 2202) of the specimen from the time of bloodletting etc. to sorting to transfer up a lift system directly upwards to the full laboratory on the floor immediately above the specimen collection site. The specimen moves from Level 1 2220 from collection 2204, to sorting 2206 up though the transfer 2208 as illustrated by the unidirectional arrow 2202. The specimen then moves up to level 2 2222 up to processing 2210. On level 2 2222 of the full laboratory, the specimen is processed within 10 minutes for patients who are attending clinic on the same day so the results are immediately available for their assessments. The reusable supplies are then transferred back down to level 1 2220 where any reusable supplies 2212 are transferred back. The transfer occurs on a lift or other similar transportation system configured to transport the physical specimens.

This physical set up and procedure for laboratory specimens collection and processing has the potential to reduce emergency room utilization as when labs are done 1-2 weeks prior to the clinic visit, patients are often directed to the emergency room to deal with issues on their laboratory investigations because clinical assessment is not immediate at the time of the testing. In this model, because the testing is the same day as the clinic visit, patients will be assessed and issues dealt with identified on their lab work on the same day.

This also enables clinicians to react to real-time immediate results in their clinical assessments. It reduces the need for repeat lab work due to data that is not most current. The present 2 level (or otherwise multi-level) system is advantageous because if the lab was next to the clinic on the same floor, it would not be as efficient a process with collection, processing and transfer back and forth of specimens and supplies. The 2 level arrangement allows samples to be transferred up to maximize floor space to mitigate the need of transfer carts, people . . . etc. to physically move the samples across a building. Moving specimens vertically and mechanically is significantly more efficient.

It allows for increased utilization of more cost effective real-time immediate community-based clinical assessments and less reliance on emergency room departments and hospitals to be able to do real time immediate laboratory investigations and assessments.

The design of the present specification is configured to eliminate the fundamental problems, as previously described, with the current healthcare model. Patients will have access to their primary care physician, a select group of vascular health specialists, including cardiology, nephrology, endocrinology, neurology, and vascular surgery (available on-demand for 'quick' problem specific consultation), a medical laboratory, imaging, diagnostics, and pharmacy services, all at the same location, and in the same visit.

By implementing the below described design and utilizing the corresponding computer program and companion mobile device application (as described in the parent), healthcare providers will be able to increase the efficiency and quality of healthcare delivery, facilitate and simplify coordination of care, enhance patient involvement in healthcare decisions and measure and improve health outcomes in patients with vascular disease through clinical evidence-based strategies. By implementing this complete design, a new gold standard of healthcare will be achieved.

The present specification includes both an Electronic Operating System (EOS) for the clinic and autonomous vehicle management system and for the Electric Autonomous Vehicle itself.

Electronic Operating System (EOS)—Clinic and Autonomous Vehicle Management System The EOS as herein described is the operating system of the vehicle and the entire clinic. Not only does the EOS allow navigation through the clinic etc. (such as previously described and herein incorporated by reference) but it is actually the vehicle operations system as well which controls mechanical autonomous functions and mechanical remote operational technology and artificial intelligence systems.

The same automation occurs in exam rooms at the clinic so the staff never has to go into the room. With the screens facing the patient the camera system and the EOS program, the assessor doesn't even have to physically be in the building or even in the city to assess the patient.

Further, the EOS provides for the ability to incorporate artificial intelligence in making diagnoses and suggesting treatments. For example, the ability to scan a skin rash and compare it to a database. An advantage is the ability to make a diagnosis and prescribe therapy immediately.

Eventually, the physical building is a command center with rooms and workspaces. Nurses and staff video will conference into the vehicle and asks the patient questions to prepare for a visit so in the transition phase, your assessment starts the minute the patient leaves their home and makes the entire visit more efficient. This can be done through a command center that is exclusively focused on this, once the volume for the service increases.

After transitioning to completely virtual assessments, physical examination, lab work and imaging internal assessments can be done through the electronic operating system using remotely controlled robotic apparatus. This will combine x-ray technology, ultrasound, Imaging sensor technology and camera technology both attached to individual equipment and in the outer and interior frame of the vehicle. The vehicle itself will have equipment within the frame of the vehicle, both on the outer and inner aspect that will facilitate autonomous operation and clinical assessment.

If labs have already done by mobile lab draw, the clinic visit can been performed virtually from a patient's driveway with clinical assessment and imaging data taken in the vehicle and video conference information from the command center.

The same vehicles can transport people to and from the emergency room in non-life-threatening situations for assessment from the clinic and then to their homes also, with communication of their electronic medical record and medical history with that emergency room department. During any assessment, continuous monitoring of vitals and parameters and particularly on transport to the emergency room can allow the recognition of concerning heart rhythms and one of the devices the vehicle will be equipped with is an automated external defibrillator that will positioned and used if a shockable rhythm is detected.

In terms of the artificial intelligence used with the equipment, equipment can learn to recognize landmarks while scanning a patient's body to determine the direction of probes such as ultrasound probes required to complete a full examination. This is true for the placement of blood pressure cuffs sensors, EKG sensors, Carotid Doppler sensors and any other imaging.

The cab component of the vehicle and functions can be duplicated for at home use once the technology costs decline over time. Using the technology remotely will be controlled by the natural movement of your hands that is detected by the Artificial intelligence programming and virtual space mapping.

In the interior compartment, a centrally positioned is present that can swivel and lock in place can initially be healthcare personnel and transition to being used by a caregiver that assists patient from the same household with virtual assistance.

The coordination and professionals doing the virtual care can be based from the research facility—but doesn't have to be. This allows for the patient to have care delivered by the physicians and allied healthcare professionals of their choice regardless of location. The coordination can occur through the Research facility in command Center at the main base. This is where the virtual technology specialists will be stationed that can control the equipment with precision. They will be the ones who are controlling the vehicle Equipment from the command center and have specialized training in that particular technology.

The EOS will control the path and scheduling and destinations of the fleet of autonomous vehicles. EOS will be integrated with the hardware and control the hardware within the autonomous vehicle. The EOS will also be the portal through which control of the hardware within the vehicles is allowed through strict permissions. It will also serve as the portal for controlling hardware devices remotely.

The EOS system coordinates activity in the fleet of vehicles as well as activity in the physical plant structure.

The EOS coordinates the notifications to both practitioners and patients and the distance to the next scheduled patient and the type of care needed at what time—when the next car becomes available that is suitable for that specific visit.

The EOS Keeps digital video records of physical examination for comparison. No more writing down what you saw—now you can actually see data and measure specifically things like Edema, rashes, jvp, record heart sounds, assess appearance, lymph nodes, ascites, x-ray images, ultrasound findings within a single record and compare to previous images etc.

Electric Autonomous Vehicle

The Vehicles of the present specification are electric autonomous vehicle capable of holding 2-3 passengers and is wheelchair accessible. The back windows are tinted dark for privacy. One body for all different types of vehicles. The only difference is the technology placed in each vehicle. The advantage to this as a vehicle made with minimal technology, for example the pharmacy car can be easily retrofitted to be any other type of car. In this configuration, the car is modular as well. The back compartment is tall enough for a patient to stand, sit and completely recline. This large space will help in the ability due to diagnostics—such as x-ray and ultrasound imaging. However, the cab will be still short enough to go through any overpass and even park in your garage. The doors open up and have no handles. The doors can be opened and closed through the command center only when the vehicle is in park.

The inside of the vehicle is adapted to include all necessary components for patent evaluation and diagnosis. Every piece of equipment is built into the vehicle system and comes out of the vehicle itself. For example, blood pressure, EKG lead and other diagnostic equipment arise from the interior side walls, floor or roof of the vehicle and through camera systems at the exact spots needed.

In some examples, the mobile lab draw with lab tech in front, plexiglass screen separating lab tech from patient in place just put an arm and can go around to do lab draws if needed to avoid clinic visits in a pandemic. The lab draws will transition to ultrasound guided vein mapping remote phlebotomy using robotics to exactly insert the needle into veins with direct ultrasound visualization which will minimize trauma to the patient.

Evolution to robotics where everything is touchless is incorporated into the present autonomous vehicle. The entire exam is done by controlling the apparatus and equipment either through a manipulation of the control system or eventually by hand motion and can be done remotely from command center. Procedures such as examining a patient's throat or ears or nasal cavity, or performing a full ultrasound of the abdomen and or a chest x-ray are examples of how remote robotics and technology will be used in the system to facilitate clinical assessments. By way of another example, of the robotic control of a stethoscope with audio recording and transmission to the control center can allow a clinician to remotely listen to a patient's heart and lungs. As another example, the use of the robotic arm with a simulated hand attached can allow the clinician to examine the patient as if being present in the vehicle.

Viewer and screen for family or caregivers who are given appropriate permissions to join in on the visit and can do so from any location. This allows family members and caregivers to be present without undue inconvenience.

As a transitional phase from in person to completely remote clinical assessments, a divider can be placed such as plexiglass between the posterior and anterior components with appropriate carrots to allow safe assessment a patient brought to the physical plant in assessment bays that are open air as in the physical plant design.

Both the anterior and posterior compartment of the vehicle will have independent negative pressure ventilation systems built-in to minimize the risk of infectious transmission.

Both the anterior and posterior compartments will have self-disinfecting systems. Touch sensors and scanners and cameras will provide an automated identification of priority areas for disinfection and there will be a generalized aerosol disinfecting system built into the interior of the vehicle. The system detects everything that each occupant touches to focus areas of disinfection and disinfectant evaporates within minutes. Disinfection occurs in transport between locations and there is generalized aerosolized disinfection of the compartment as well for droplets.

The patient seat is electronically controlled for positioning by assessor.

Further, different models of the vehicle can be produced and even easily retrofitted to transition from one model to another if needed. By way of example, different Models includes:

Model A—examination and questionnaire
Model B—lab draw
Model C—imaging
Model D—pharmacy pick up and drop off with counseling
Model E—combine all The panels of the vehicle contains strategically placed instruments that can robotically be extended to the desired site use and positioned appropriately. Cameras and sensors allow appropriate visualization and clinical data collection. Robotic arms are strategically placed throughout the posterior compartment and will have access to strategically placed supplies all of which can be controlled from within the anterior compartment or remotely.

In some embodiments, the scheduling system allows for scheduling multiple specialists and allied healthcare professionals to assess the patient at the same visit. The scheduling process not only sends out the autonomous vehicle for pick up but also is able to generate preassessment questionnaires for each health care. A specialist seeing the patient that day. These can be displayed in the vehicle on the drive to the clinic and the questions can be asked of the patient by automated voice over and using voice recognition they can submit their answers while they're being driven over.

The virtual healthcare provider can review the answers given by the patient and can then talk to the patient to clarify any of their answers.

Using Risk and Benefit Based Calculations to Prioritize uptake of Therapy

The uptake of proven therapies to reduce an individual patient's risk of adverse events remains poor, and in some studies as low as 40-50% of therapies or actually prescribed and consistently taken by patients. This leads to elevated risk profiles for patients for adverse outcomes, as well as having impacts on community public health measures and hospital based services. Strategies are needed to optimize uptake and compliance to medical therapies proven to improve outcomes. (1,2). There is often therapeutic inertia on the part of the patient and the physician as well as health equity factors that prevent the optimal uptake of proven therapies and these strategies are designed to address this phenomenon.

In the present embodiment, a TOR greater than 10 triggers PTI (Priority Treatment Index) calculations. Priority Treatment Index (PTI) is a measure of the percentage and weight of the total priority evidenced based treatments implemented and individualized to all of that patient's SPA risk factors. They can be pharmaceutical or lifestyle modification. There can be up to 10 PTI risk attenuation factors per SPA risk amplification factor. Each SPA score risk amplification factor (used to calculate the overall TOR score) triggers the automatic population of the associated Priority Treatment attenuation factors associated with that SPA category (up to 10 max) (used to calculate the overall PTI score). Weights are given to all SPA amplification factors and Priority Treatment Index attenuation factors based on levels of evidence documented and accepted recommendations. The same Weights can be used for acuity and attenuation factors.

Recommendation: relative weights

A—1.5

B—1.3

C—1.1

D—1.0

(assigned to SPA Amplification/PTI Attenuation Factor)

Medications and Therapies are tagged to SPA factors with priority recommendations options given to health care provider with references to studies also provided. Priority:

1. drug specific effects tags and dosing.
2. class effect tags and options with dosing.

Non—Pharmaceutical Therapies also are recommended based on SPA factors in the same fashion with therapy and dosage. Prior to and at each visit, the app will generate the top 2 treatments according to recommendation rank in the systems with the highest spa scores to address at that interaction for both the patient and MD to be aware of and address—as either contraindicated, implemented, or deferred. If the patient and physician work hard on the patients PTI, and adjust the TOR score the incentive is the patient will have better care with fewer visits. There's also a greater incentive to focus on intensive outpatient chronic disease management. In addition to socio-physiologic COM/SPA systems in the app there will be a Health Equity and Access system, measurements of:

1) number of "missed" visits calculated based on risk TOR scheduling either due to patient or system factors will be tallied as SPA risk amplification factor with greatest weights given to the systems with the highest SPA scores (1.5-1.0 weights)
2) The average Continuity of Care COC across all systems index will be continually calculated as a PTI risk attenuation factor with greatest weights being given to the systems with the highest SPA scores (1.5-1.0. weights)

The app will display TOR, PTI and adjusted TOR. The adjusted TOR (a predicted estimation) can then be used to modify scheduling frequency. As statistical analysis proceeds within the data collected within the application, the adjusted TOR can move from a predicted estimation to a calculation based on absolute risk reductions associated with each priority attenuation factor quantified in clinical studies.

The initial TOR score of generated will be the untreated TOR score ("uTOR"). After the priority, therapeutic index is calculated, a modifiable TOR ("mTOR") score is generated according to the below formula:

$$mTOR = uTOR/\Sigma(SPA \text{ risk being treated} \times SPA \text{ associated } PTI \text{ factor weight})$$

This mTOR score can be used to adjust scheduling to reduce frequency of visits inversely proportional to the value of the mTOR score.

Practitioner Service Intensity (PSI). It has thus far been very difficult within health systems to measure practitioner service intensity (PSI) as a reflection of patient complexity. Complex patients require increased time and resources for their care, and this is often not reflected in most practitioner renumeration formulas. This creates many challenges within healthcare systems, particularly with respect to workload measurement accuracy. The application measures practitioner service intensity for any given patient through the following formula:

$$PSI = TOR + \Sigma TPA$$

Health care professionals realize that not all patients require the same intensity of care and measures of such are necessary for understanding the needs for patients and the level of service being provided by the practitioner. The higher the PSI the increased priority given to a patient by a practitioner. Using the PSI to determine a preference, priority, or other level to schedule an appointment for a patient.

Each TPA factor will be assigned an evidence-based weight to indicate its relative importance as a risk attenuation factor. In any given system, the sum of all these values creates a TPA score for that system.

The Priority Treatment Index (PTI) is a measure of the percentage and weight of the total non-duplicative evidenced based treatment priority attenuation (TPA) factors implemented and individualized to all of that patient's SPA factors.

$$PTI = \Sigma(TPA \text{ implemented} \times \text{assigned weight})/\Sigma(TPA \text{ total} \times \text{assigned weights})$$

The priority treatment index is an index with a scale between 0 and 1, with one being the most optimal score attainable.

Prior to and at each interaction with any system practitioner, the algorithm will trigger a mandatory review of remaining treatment priority attenuation (TPA) factors for that system that have not yet been instituted and a mandatory checklist will be prompted to be filled out by the system practitioner to ensure discussion and decision-making surrounding these priority treatments has occurred.

It is important to note that the acute systems (Acute Signs and Symptoms and Homeostatic Indicator) will be tied to specific SPA and TPA factors that increase the patient's risk in the presence of categories listed under these systems.

As statistical analysis proceeds within the data collected within the application, the adjusted TOR can move from a predicted estimation to a calculation based on absolute risk reductions associated with each priority attenuation factor quantified in clinical studies.

Acute and Homeostatic Systems

Most, if not all patients decide to visit in urgent care or emergency room based on their own interpretation of their symptoms, and how severe they are, with no background medical training or advice regarding their own personal risks in the setting of an acute illness. Often patients present to urgent cares or emergency rooms with quite severe symptoms that require hospital admission because of their late presentation.

With risk-based scheduling, this is included acute system and homeostatic system categories for scheduling into the urgent care at the facility.

By way of example, if a patient developed a fever or other acute symptoms at home, they enter it into their app—the program then checks their existing SPA and TPA factors to see if any of their specific medical conditions or treatments elevates their risk in the setting of having a fever. This then generates a SPA score for the acute system category and transiently elevates their TOR score until this issue is resolved. The elevated SPA score (for the acute system) can then trigger scheduling into the urgent care. The patient is notified through the messaging system in the application that their risk is elevated in the setting of that acute system given their existing medical profile. It then can also recommend visiting the urgent care center to avoid further deterioration and the need for an emergency room visit.

The Homeostatic system include SPA risk factors such as a recent hospital, admission, or a recent change in medication, etc. that would alter a patient's homeostasis from their baseline.

It is noted that the terms "substantially" and "about" may be utilized herein to represent the inherent degree of uncertainty that may be attributed to any quantitative comparison, value, measurement, or other representation.

These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter.

Moreover, although various aspects of the claimed subject matter have been described herein, such aspects need not be utilized in combination.

It is therefore intended that the appended claims cover all such changes and modifications that are within the scope of the claimed subject matter.

We claim:

1. A method of automated medical scheduling comprising:
   receiving user specified data on a processor via a checklist, said data being a plurality of predetermined physical conditions of a patient, each of the plurality of predetermined physical conditions having a predetermined assigned weight based on level of severity;
   generating a summation of the total weight for each predetermined physical condition;
   generating a predetermined specialty acuity ("SPA") score by comparing the corresponding range of the total weight;
   an Total Overall Risk ("TOR") score is generated by multiplying the summation of each system by the total SPA scores, generating a report of the TOR score;
   if the TOR is greater than 10, a Priority Treatment Index ("PTI") is generated;
   assigning a Treatment Priority Acuity ("TPA") score, the TPS score calculating a Practitioner Service Intensity ("PSI") by multiplying the TOR by the summation of the TPA;
   using the PSI is used to predict required practitioner service intensity; and
   using the above PSI to schedule at least one appointment for said patient in a system schedule.

2. The method of automated medical scheduling of claim 1 wherein a SPA score is generated for each system affected, the systems including Cardiac, Renal, Neurological, Vascular, Medical/Metabolic and Pulmonary, each assigned a value of 1.

3. The method of automated medical scheduling of claim 2 wherein a comorbidity score is generated by the summation of each system.

4. The method of automated medical scheduling of claim 3 to determine frequency of appointment scheduling, comparing the TOR score to a set of predetermined ranges, assigning an appointment interval corresponding with the TOR score value.

5. The method of automated scheduling of claim 4 wherein an appointment interval is assigned for ancillary care assessments corresponding to the TOR score value.

6. The method of automated scheduling of claim 4 wherein the TOR score is used to determine visit frequency as an amplifier for SPA score passed on physician visits.

* * * * *